US010123828B2

(12) United States Patent
Matityahu et al.

(10) Patent No.: US 10,123,828 B2
(45) Date of Patent: Nov. 13, 2018

(54) IMPLANTABLE DEVICE WITH PIVOTABLE FASTENER AND SELF-ADJUSTING SET SCREW

(71) Applicant: EPIX Orthopaedics, Inc, Los Altos, CA (US)

(72) Inventors: Amir M. Matityahu, Los Altos, CA (US); Benjamin Clawson, Santa Cruz, CA (US)

(73) Assignee: Epix Orthopaedics, Inc., Los Altos, CA (US)

( * ) Notice: Subject to any disclaimer, the term of this patent is extended or adjusted under 35 U.S.C. 154(b) by 0 days.

(21) Appl. No.: 14/213,222

(22) Filed: Mar. 14, 2014

(65) Prior Publication Data

US 2014/0330274 A1    Nov. 6, 2014

Related U.S. Application Data

(60) Provisional application No. 61/800,921, filed on Mar. 15, 2013.

(51) Int. Cl.
*A61B 17/72* (2006.01)
*A61B 17/74* (2006.01)

(52) U.S. Cl.
CPC .......... *A61B 17/748* (2013.01); *A61B 17/744* (2013.01)

(58) Field of Classification Search
CPC ...................................... A61B 17/70–17/7291
See application file for complete search history.

(56) References Cited

U.S. PATENT DOCUMENTS

| 3,783,860 A | 1/1974 | Burstein et al. |
| 4,519,100 A | 5/1985 | Wills et al. |
| 4,622,959 A | 11/1986 | Marcus |
| 4,653,487 A | 3/1987 | Maale |

(Continued)

FOREIGN PATENT DOCUMENTS

| DE | 102008013699 A1 | 9/2009 |
| EP | 0696441 A2 | 2/1996 |

(Continued)

OTHER PUBLICATIONS

Advisory Action and Response After Final dated Nov. 9, 2011 for U.S. Appl. No. 12/143,798, filed Jun. 22, 2008, pp. 1-4.

(Continued)

*Primary Examiner* — Jan Christopher Merene
*Assistant Examiner* — Steven Cotroneo
(74) *Attorney, Agent, or Firm* — Intellectual Innovations Legal Advisors

(57) ABSTRACT

An intramedullary device to repair a bone in a mammalian body and comprising an elongate nail having a stem and a head. The head is provided with a transverse aperture adapted to receive a fastener. An adjustment mechanism is carried by the head for pivoting the fastener from a first angled position relative to the head to a second angled position relative to the head. A set screw is carried by the head. The distal end of the set screw is movable relative to the proximal end of the set screw from a first position for lockably engaging the fastener in the first angled position and a second position for lockably engaging the fastener in the second angled position. A sealing cap and an apparatus having a cap and a set screw are additionally provided.

22 Claims, 37 Drawing Sheets

(56) References Cited

U.S. PATENT DOCUMENTS

| | | | |
|---|---|---|---|
| 4,657,001 A | 4/1987 | Fixel | |
| 4,733,654 A | 3/1988 | Marino | |
| 4,776,330 A | 10/1988 | Chapman et al. | |
| 4,827,917 A | 5/1989 | Brumfield | |
| 4,846,162 A | 7/1989 | Moehring | |
| 4,881,535 A | 11/1989 | Sohngen | |
| 5,032,125 A | 7/1991 | Durham et al. | |
| 5,041,114 A | 8/1991 | Chapman et al. | |
| 5,047,034 A | 9/1991 | Sohngen | |
| 5,127,913 A | 7/1992 | Thomas, Jr. | |
| 5,167,663 A | 12/1992 | Brumfield | |
| 5,176,681 A | 1/1993 | Lawes et al. | |
| 5,190,544 A | 3/1993 | Chapman et al. | |
| 5,248,313 A | 9/1993 | Greene et al. | |
| 5,429,640 A | 7/1995 | Shuler et al. | |
| 5,454,813 A | 10/1995 | Lawes | |
| 5,505,734 A * | 4/1996 | Caniggia | A61B 17/7225 606/63 |
| 5,514,137 A | 5/1996 | Coutts | |
| 5,562,667 A | 10/1996 | Shuler et al. | |
| 5,653,709 A * | 8/1997 | Frigg | A61B 17/72 606/62 |
| 5,772,662 A | 6/1998 | Chapman et al. | |
| 5,935,127 A | 8/1999 | Border | |
| 6,120,504 A | 9/2000 | Brumback et al. | |
| 6,123,708 A | 9/2000 | Kilpela et al. | |
| 6,126,661 A | 10/2000 | Faccioli et al. | |
| 6,221,074 B1 | 4/2001 | Cole et al. | |
| 6,235,031 B1 | 5/2001 | Hodgeman et al. | |
| 6,276,883 B1 * | 8/2001 | Unsworth | F16B 37/12 411/16 |
| 6,402,753 B1 | 6/2002 | Cole et al. | |
| 6,406,477 B1 | 6/2002 | Fujiwara | |
| 6,443,954 B1 | 9/2002 | Bramlet et al. | |
| 6,488,684 B2 | 12/2002 | Bramlet et al. | |
| 6,562,042 B2 | 5/2003 | Nelson | |
| 6,648,889 B2 | 11/2003 | Bramlet et al. | |
| 6,702,816 B2 | 3/2004 | Buhler et al. | |
| 6,783,529 B2 | 8/2004 | Severns et al. | |
| 6,860,691 B2 | 3/2005 | Unsworth et al. | |
| 6,893,443 B2 | 5/2005 | Frigg et al. | |
| 6,926,719 B2 | 8/2005 | Sohngen et al. | |
| 7,001,386 B2 | 2/2006 | Sohngen et al. | |
| 7,008,425 B2 | 3/2006 | Phillips | |
| 7,041,104 B1 | 5/2006 | Cole et al. | |
| 7,267,678 B2 | 9/2007 | Medoff | |
| 7,601,153 B2 * | 10/2009 | Shinjo | A61B 17/744 606/62 |
| 7,670,340 B2 | 3/2010 | Renzi et al. | |
| 7,771,428 B2 | 8/2010 | Siravo et al. | |
| 8,100,911 B2 | 1/2012 | Yamazaki et al. | |
| 8,790,343 B2 * | 7/2014 | McClellan | A61B 17/7241 606/64 |
| 2002/0133156 A1 | 9/2002 | Cole | |
| 2002/0151898 A1 * | 10/2002 | Sohngen | A61B 17/68 606/62 |
| 2002/0156473 A1 | 10/2002 | Bramlet et al. | |
| 2003/0036758 A1 | 2/2003 | Frigg et al. | |
| 2003/0114855 A1 * | 6/2003 | Wahl | A61B 17/7225 606/67 |
| 2004/0106922 A1 | 6/2004 | Snyder | |
| 2005/0010226 A1 | 1/2005 | Grady et al. | |
| 2005/0055023 A1 * | 3/2005 | Sohngen | A61B 17/7241 606/62 |
| 2005/0085812 A1 | 4/2005 | Sherman et al. | |
| 2005/0149025 A1 | 7/2005 | Ferrante et al. | |
| 2005/0182405 A1 | 8/2005 | Orbay et al. | |
| 2005/0182406 A1 | 8/2005 | Orbay et al. | |
| 2005/0234457 A1 | 10/2005 | James et al. | |
| 2006/0015101 A1 | 1/2006 | Warburton et al. | |
| 2006/0058887 A1 | 3/2006 | Desmet et al. | |
| 2006/0069392 A1 | 3/2006 | Renzi et al. | |
| 2006/0106398 A1 | 5/2006 | Lauryssen et al. | |
| 2006/0122600 A1 | 6/2006 | Cole et al. | |
| 2007/0049938 A1 | 3/2007 | Wallace et al. | |
| 2007/0049939 A1 | 3/2007 | Wallace et al. | |
| 2007/0049940 A1 | 3/2007 | Wallace et al. | |
| 2007/0100343 A1 | 5/2007 | Cole et al. | |
| 2007/0123873 A1 * | 5/2007 | Czartoski | A61B 17/72 606/62 |
| 2007/0123876 A1 | 5/2007 | Czartoski et al. | |
| 2007/0123878 A1 | 5/2007 | Shaver et al. | |
| 2007/0162016 A1 | 7/2007 | Matityahu | |
| 2007/0179835 A1 | 8/2007 | Ott, IV et al. | |
| 2007/0233100 A1 | 10/2007 | Metzinger | |
| 2007/0233101 A1 | 10/2007 | Metzinger | |
| 2007/0233102 A1 | 10/2007 | Metzinger | |
| 2007/0233103 A1 | 10/2007 | Metzinger | |
| 2007/0233104 A1 | 10/2007 | Metzinger | |
| 2007/0270845 A1 | 11/2007 | Watanabe et al. | |
| 2007/0270846 A1 | 11/2007 | Metzinger | |
| 2007/0276385 A1 | 11/2007 | Schlienger et al. | |
| 2008/0039845 A1 | 2/2008 | Bonutti et al. | |
| 2008/0077142 A1 | 3/2008 | James et al. | |
| 2008/0091203 A1 | 4/2008 | Warburton et al. | |
| 2008/0140077 A1 * | 6/2008 | Kebaish | A61B 17/744 606/64 |
| 2008/0147066 A1 | 6/2008 | Longsworth et al. | |
| 2008/0147067 A1 | 6/2008 | Phillips | |
| 2008/0161805 A1 | 7/2008 | Saravia et al. | |
| 2008/0287949 A1 | 11/2008 | Keith et al. | |
| 2009/0048598 A1 | 2/2009 | Ritchey et al. | |
| 2009/0048600 A1 * | 2/2009 | Matityahu | A61B 17/7241 606/62 |
| 2009/0306666 A1 | 12/2009 | Czartoski et al. | |
| 2010/0094293 A1 | 4/2010 | McClellan et al. | |
| 2010/0249781 A1 * | 9/2010 | Haidukewych | A61B 17/7241 606/62 |
| 2010/0268229 A1 | 10/2010 | Siravo et al. | |
| 2011/0295255 A1 | 12/2011 | Roberts et al. | |
| 2014/0012259 A1 * | 1/2014 | Matityahu | A61B 17/748 606/62 |
| 2014/0058392 A1 * | 2/2014 | Mueckter | A61B 17/744 606/64 |

FOREIGN PATENT DOCUMENTS

| | | |
|---|---|---|
| EP | 0845245 A2 | 6/1998 |
| EP | 1356777 A2 | 10/2003 |
| EP | 1557131 A1 | 7/2005 |
| EP | 1639953 A1 | 3/2006 |
| EP | 1839609 A1 | 10/2007 |
| GB | 2387112 A | 10/2003 |
| JP | 2005270503 A | 10/2005 |
| JP | 2007143942 A | 6/2007 |
| WO | WO-03053265 A1 | 7/2003 |
| WO | WO-2004096067 A2 | 11/2004 |
| WO | WO-2005092219 A1 | 10/2005 |
| WO | WO-2005094707 A2 | 10/2005 |
| WO | WO-2006066440 A2 | 6/2006 |
| WO | WO-2008089096 A2 | 7/2008 |

OTHER PUBLICATIONS

Advisory Action and Response after Final dated Nov. 14, 2012 for U.S. Appl. No. 12/576,210, filed Oct. 8, 2009. pp. 1-3.

Applicant Initiated Interview Summary dated Dec. 2, 2011 for U.S. Appl. No. 12/143,798, filed Jun. 22, 2008, pp. 1-3.

Applicant Initiated Interview Summary dated Jun. 24, 2014 for U.S. Appl. No. 12/143,798, filed Jun. 22, 2008, pp. 1-4.

Applicant-Initiated Interview Summary dated Feb. 25, 2014 for U.S. Appl. No. 12/576,210, filed Oct. 8, 2009, pp. 1-3.

DePuy Orthopaedics, Inc., Surgical Technique, Femoral Troch Entry Nailing System Options Made Easy, Versanail Femoral Troch Entry, Brochure, DePuy, a Johnson-Johnson Company, 2006, pp. 1-20.

EPO Communication dated Aug. 21, 2014 for European Application No. 12810498.1 requiring a response to the Written Opinion issued for the parent PCT application.

Examination Report dated Nov. 20, 2014 for European Patent Application No. 08780913.3 filed Dec. 22, 2006, pp. 1-4.

(56) References Cited

OTHER PUBLICATIONS

Examiner Initiated Interview Summary dated Jun. 2, 2011 for U.S. Appl. No. 12/143,798, filed Jun. 22, 2008, pp. 1-4.
Extended European Search Report dated Jun. 21, 2013 for European Patent Application No. 08780913.3 filed Dec. 22, 2006, pp. 1-5.
Final Office Action dated Jul. 19, 2012 for U.S. Appl. No. 12/576,210, filed Oct. 8, 2009, pp. 1-13.
Final Office Action dated Aug. 31, 2011 for U.S. Appl. No. 12/143,798, filed Jun. 22, 2008, pp. 1-29.
First Instructional Letter dated Jun. 6, 2011 in Response to Office Action dated Mar. 3, 2011 for Chinese Patent Application No. 200880025286.1, pp. 1-5.
First Patent Examination Report issued by the Australian Patent Office for Australian Patent Application Serial No. 2008268507, dated Dec. 4, 2012, pp. 1-4.
International Preliminary Report on Patentability for Application No. PCT/US2008/067818, dated Dec. 22, 2009, pp. 1-5.
International Preliminary Report on Patentability for Application No. PCT/US2009/060067, dated Apr. 12, 2011, pp. 1-6.
International Preliminary Report on Patentability for Application No. PCT/US2012/069958, dated Jun. 17, 2014, pp. 1-7.
International Search Report for Application No. PCT/US2008/067818, dated Oct. 8, 2008, pp. 1.
International Search Report for Application No. PCT/US2009/060067, dated Dec. 17, 2009, pp. 1-2.
International Search Report for Application No. PCT/US2012/069958, dated Mar. 19, 2013, pp. 1-4.
Non-Final Office Action dated Dec. 8, 2011 for U.S. Appl. No. 12/576,210, filed Oct. 8, 2009, pp. 1-18.
Non-Final Office Action dated Sep. 17, 2014 for U.S. Appl. No. 13/716,079, filed Dec. 14, 2012, pp. 1-5.
Non-Final Office Action dated Feb. 22, 2011 for U.S. Appl. No. 12/143,798, filed Jun. 22, 2008, pp. 1-17.
Non-Final Office Action dated Apr. 23, 2014 for U.S. Appl. No. 12/143,798, filed Jun. 22, 2008, pp. 1-16.
Non-Final Office Action dated Oct. 23, 2013 for U.S. Appl. No. 12/576,210, filed Oct. 8, 2009, pp. 1-17.
Notice of Allowance and Examiner-Initiated Interview Summary dated Mar. 26, 2014 for U.S. Appl. No. 12/576,210, filed Oct. 8, 2009, pp. 1-12.
Notice of Allowance dated Jul. 8, 2015 for U.S. Appl. No. 13/716,079, filed Dec. 14, 2012, pp. 1-5.
Notice of Allowance dated Jul. 31, 2014 for U.S. Appl. No. 12/143,798, filed Jun. 22, 2008, pp. 1-7.
Requirement for Restriction/Election dated Mar. 19, 2014 for U.S. Appl. No. 12/143,798, filed Jun. 22, 2008, pp. 1-9.
Response dated Jan. 3, 2014 for Extended European Search Report dated Jun. 21, 2013 for European Patent Application No. 08780913.3 filed Dec. 22, 2006, pp. 1-8.
Response dated Jun. 3, 2011 for Non-Final Office Action dated Feb. 22, 2011 for U.S. Appl. No. 12/143,798, filed Jun. 22, 2008, pp. 1-16.
Response dated Apr. 8, 2014 for Requirement for Restriction/Election dated Mar. 19, 2014 for U.S. Appl. No. 12/143,798, filed Jun. 22, 2008, pp. 1-7.
Response dated Jun. 8, 2012 for Non-Final Office Action dated Dec. 8, 2011 for U.S. Appl. No. 12/576,210, filed Oct. 8, 2009, pp. 1-14.
Response dated Mar. 14, 2015 for Non-Final Office Action dated Sep. 17, 2014 for U.S. Appl. No. 13/716,079, filed Dec. 14, 2012, pp. 1-12.
Response dated Oct. 14, 2011 for Final Office Action dated Aug. 31, 2011 for U.S. Appl. No. 12/143,798, filed Jun. 22, 2008, pp. 1-17.
Response dated Feb. 21, 2014 for Non-Final Office Action dated Oct. 23, 2013 for U.S. Appl. No. 12/576,210, filed Oct. 8, 2009, pp. 1-10.
Response dated Jun. 22, 2014 for Non-Final Office Action dated Apr. 23, 2014 for U.S. Appl. No. 12/143,798, filed Jun. 22, 2008, pp. 1-17.
Response dated Oct. 24, 2012 for Final Office Action dated Jul. 19, 2012 for U.S. Appl. No. 12/576,210, filed Oct. 8, 2009, pp. 1-10.
Response dated Feb. 25, 2015 for EPO communication dated Aug. 21, 2014 for European Application No. 12810498.1 filed Dec. 15, 2012.
Response dated Sep. 26, 2015 for Notice of Allowance dated Jul. 8, 2015 for U.S. Appl. No. 13/716,079, filed Dec. 14, 2012, pp. 1-7.
Response dated Apr. 30, 2014 for Examination Report dated Dec. 4, 2012 for Australian Patent Application No. 2008268507 filed Jun. 22, 2006, pp. 1-27.
Response dated Oct. 30, 2014 for Notice of Allowance dated Jul. 31, 2014 for U.S. Appl. No. 12/143,798, filed Jun. 22, 2008, pp. 1-3.
Response dated Jan. 3, 2014 for European office actions dated Jul. 9, 2013 and Jun. 21, 2013 for Application No. EP08780913.3 filed Jun. 22, 2008, pp. 1-9.
Second Instructional Letter mailed Jul. 5, 2011 in Response to Office Action dated Mar. 3, 2011 for Chinese Patent Application No. 200880025286.1, pp. 1-5.
Second Response dated Nov. 30, 2011 for Final Office Action dated Aug. 31, 2011 and the Advisory Action dated Nov. 9, 2011 for U.S. Appl. No. 12/143,798, filed Jun. 22, 2008, pp. 1-18.
Stryker Product, Gamma3—The Compact Version of the Gamma Nail System—Operative Technique: Hip Fracture System Trochanteric and Long Nails, Brochure, Literature No. LG3-0T Rev, 1, 10M Oct. 2004, Stryker, 2004, pp. 1-44, Retrieved from the internet: <www.stryker.com>.
Translation of Dec. 6, 2012 Office Action issued by Japanese Patent Office for corresponding Japanese patent application No. 2010513479 filed Jun. 22, 2008, pp. 1-3.
Translation of Sep. 14, 2013 Office Action issued by Japanese Patent Office for corresponding Japanese patent application No. 2010513479 filed Jun. 22, 2008, pp. 1.
Translation of Feb. 20, 2014 Office Action issued by Japanese Patent Office for corresponding Japanese patent application No. 2010513479 filed Jun. 22, 2008, pp. 1.
Translation of Office Action dated Mar. 3, 2011 for Chinese Patent Application No. 200880025286.1, pp. 1-10.
Written Opinion for Application No. PCT/US2008/067818, dated Oct. 8, 2008, pp. 1-4.
Written Opinion for Application No. PCT/US2009/060067, dated Dec. 17, 2009, pp. 1-5.
Written Opinion for Application No. PCT/US2012/069958, dated Mar. 19, 2013, pp. 1-7.

* cited by examiner

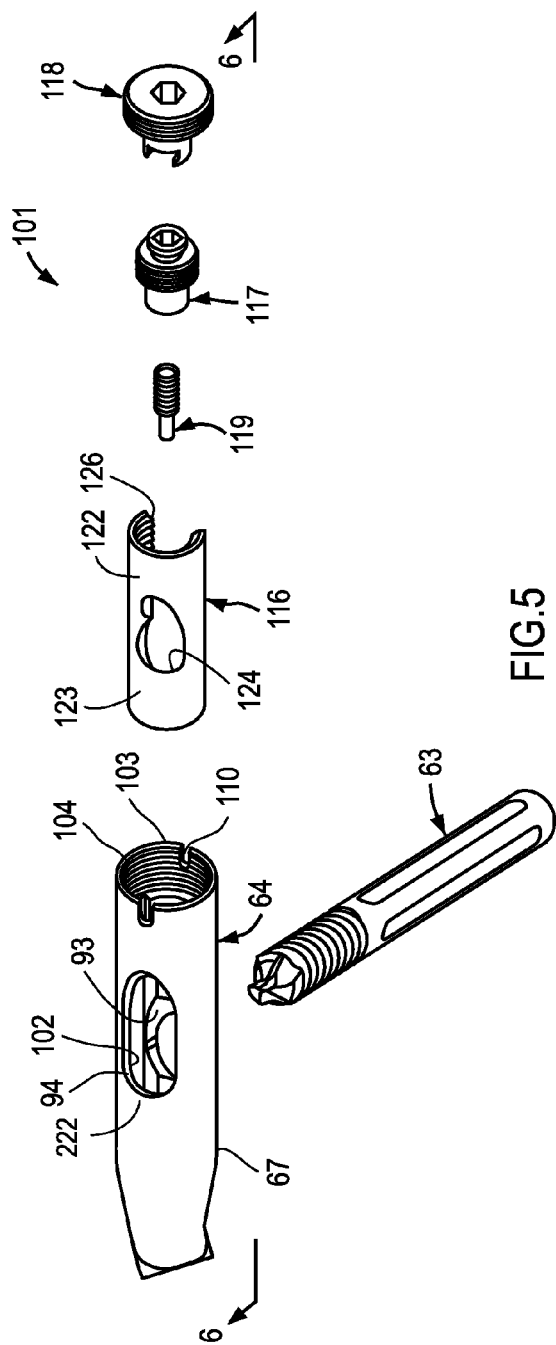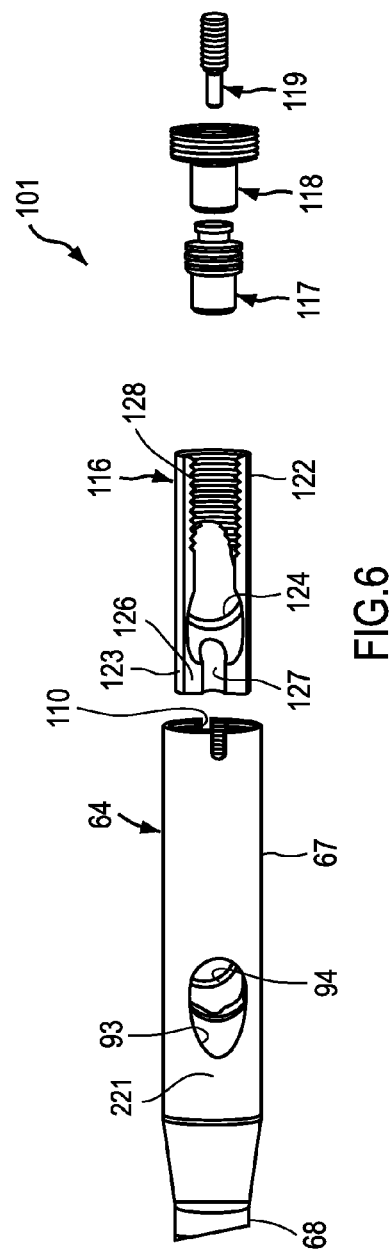

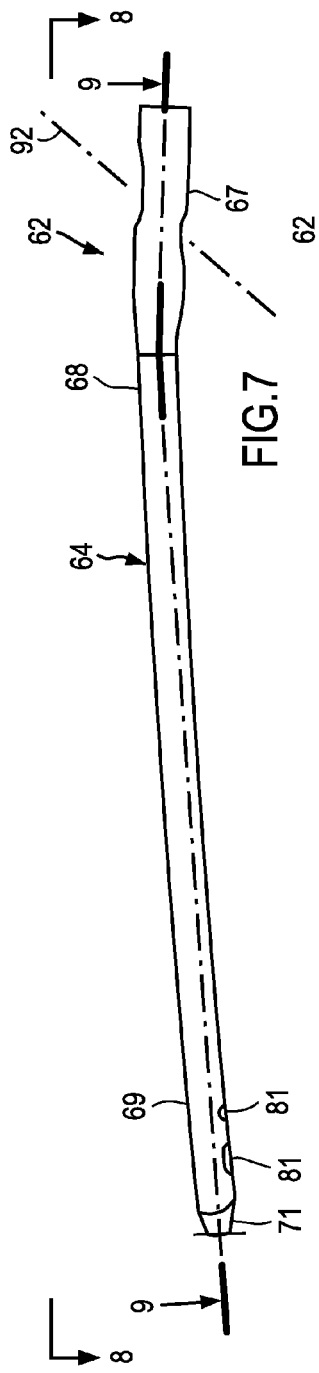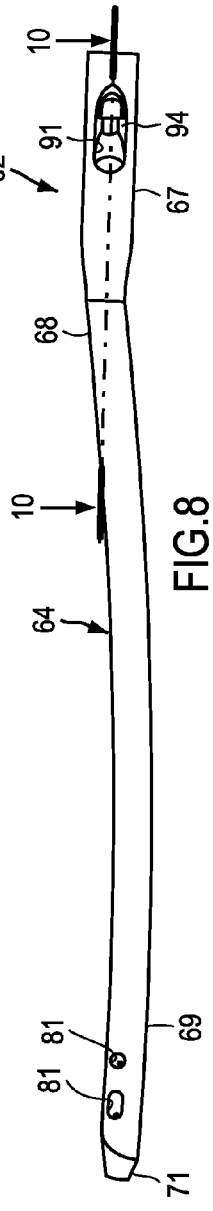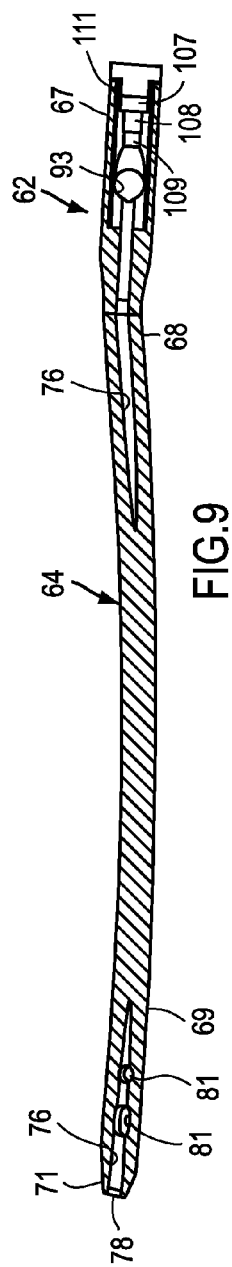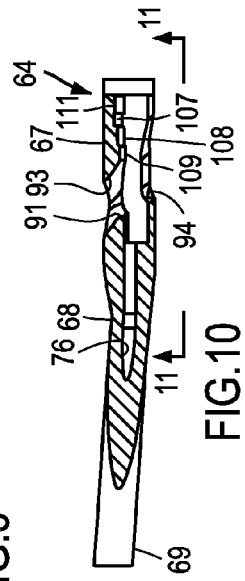

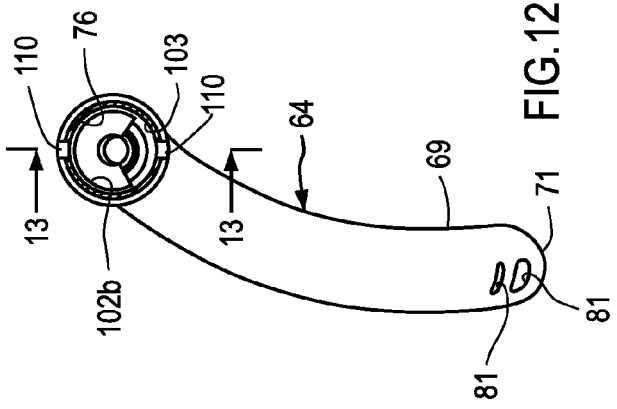
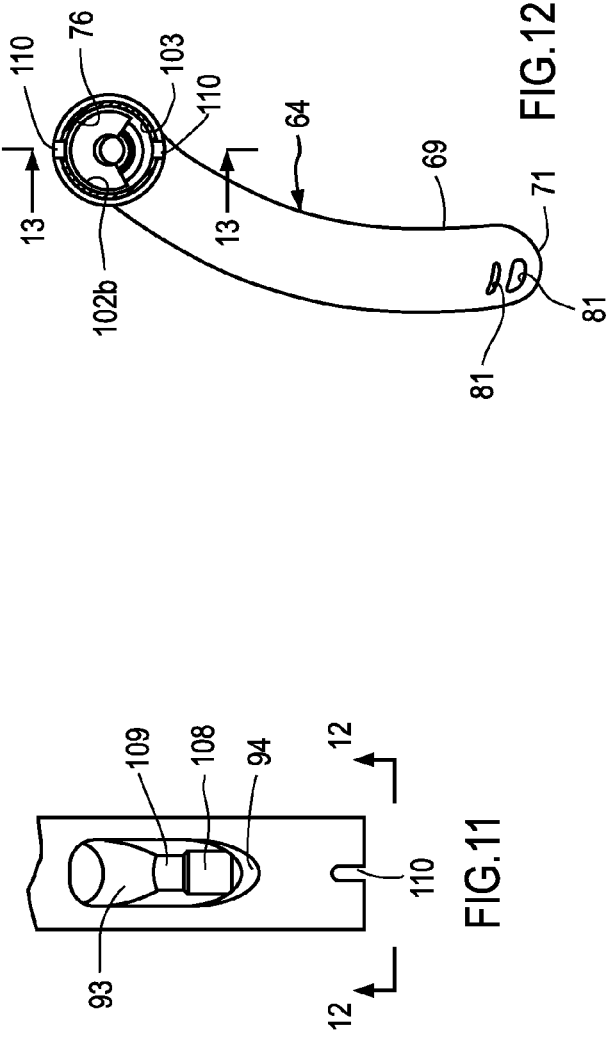
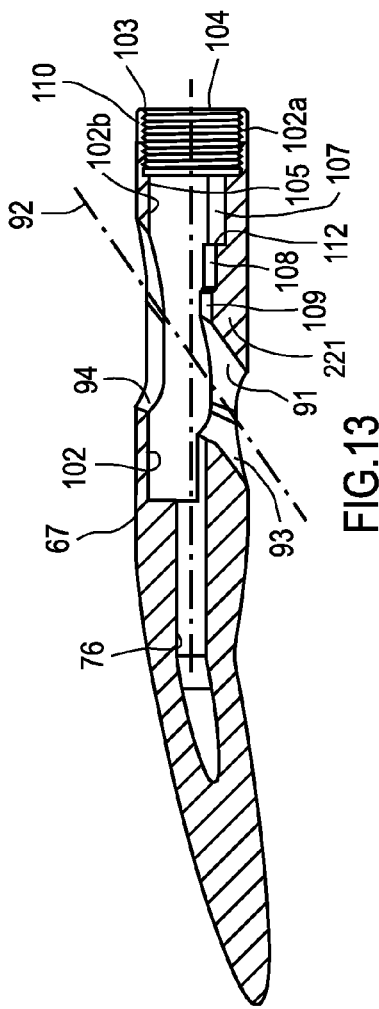

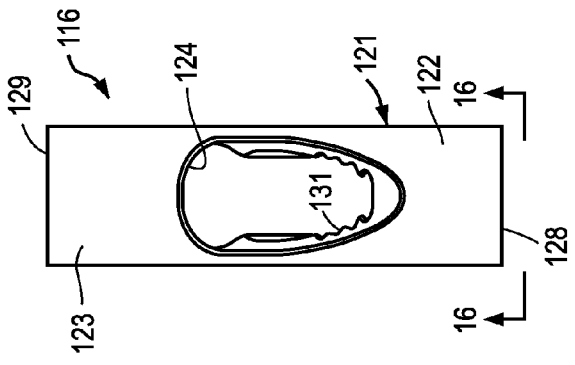
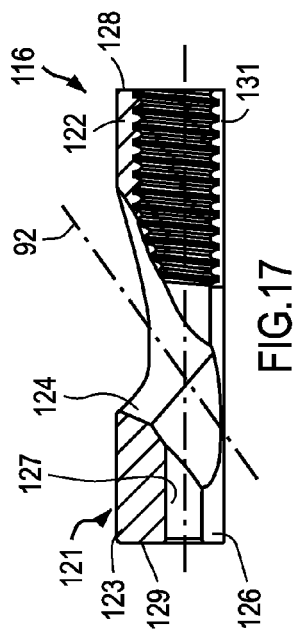
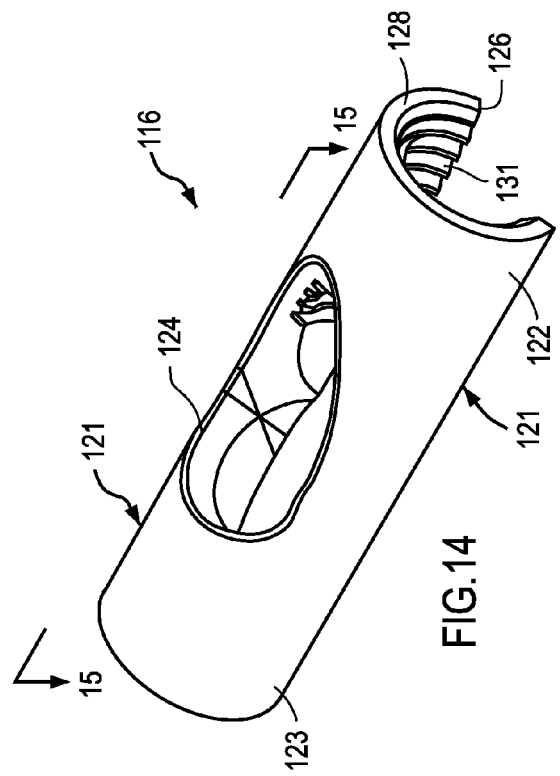
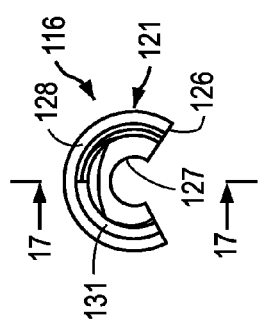

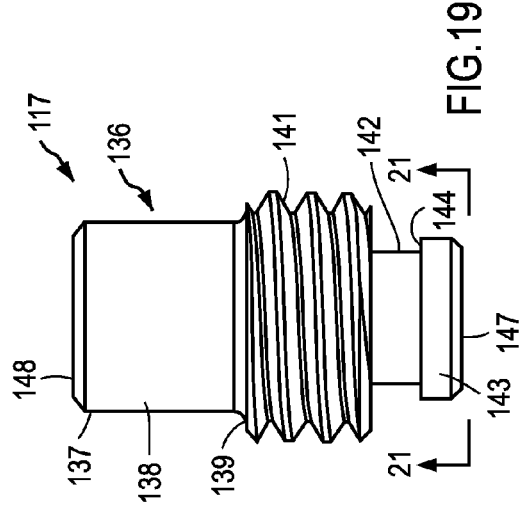
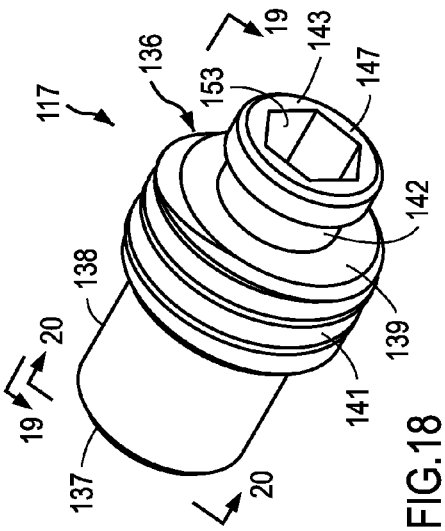
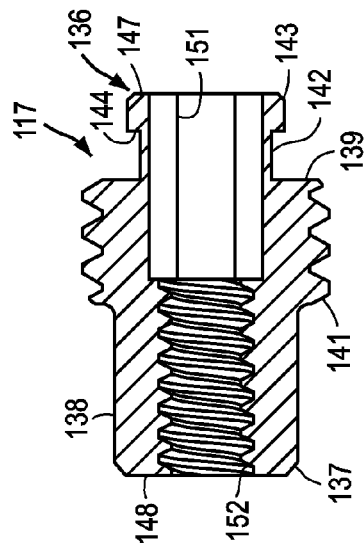
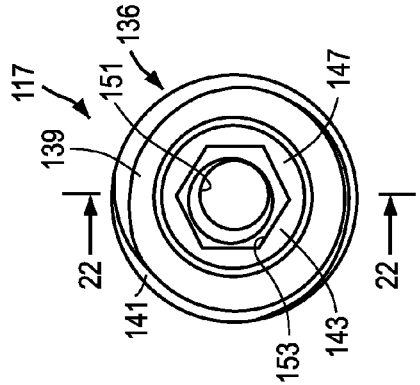
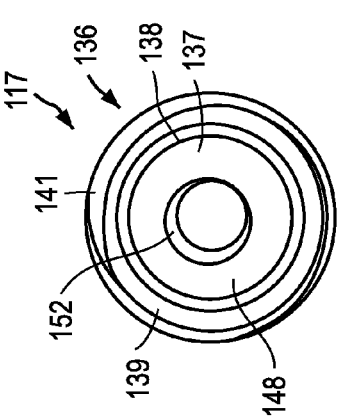

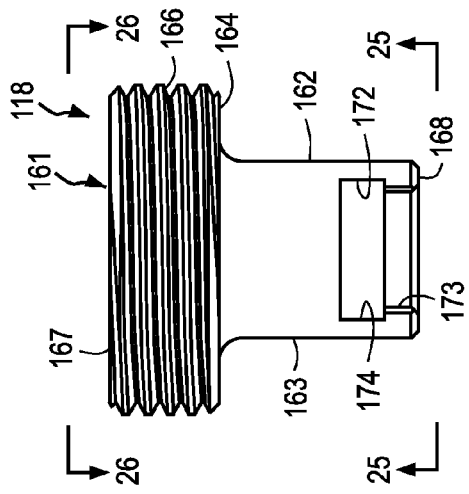
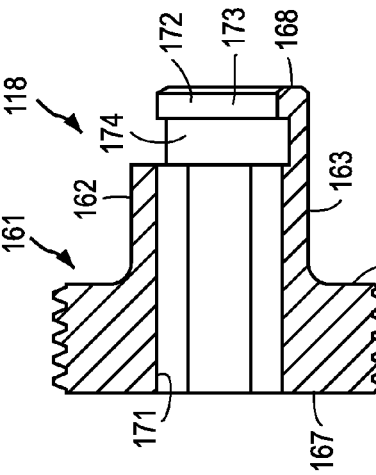
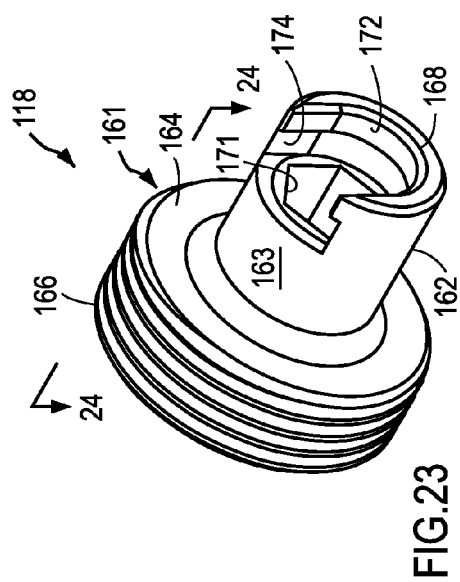
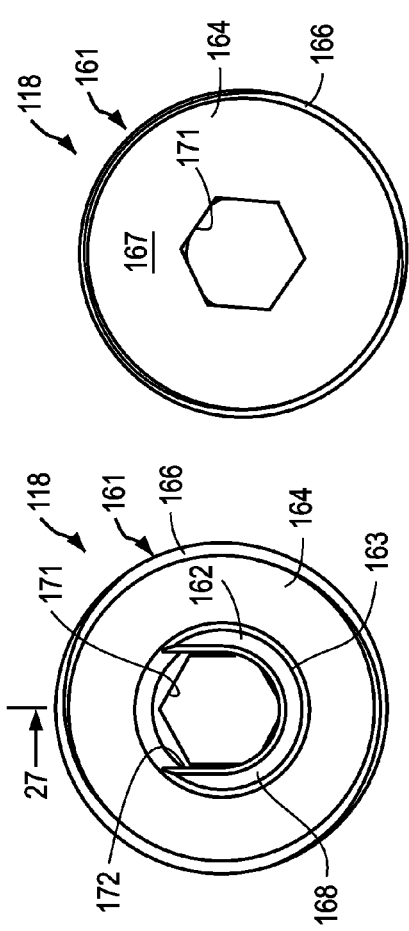

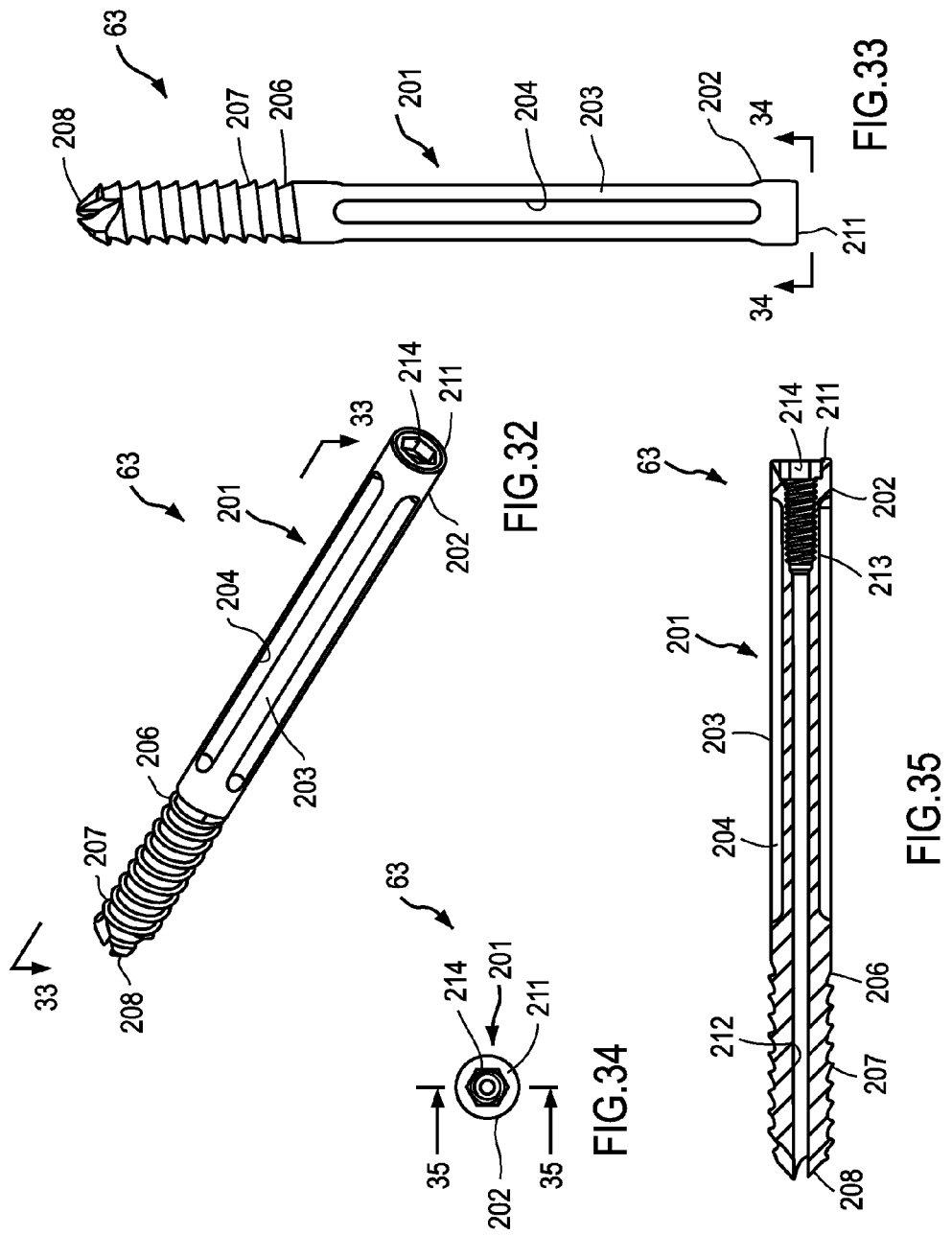

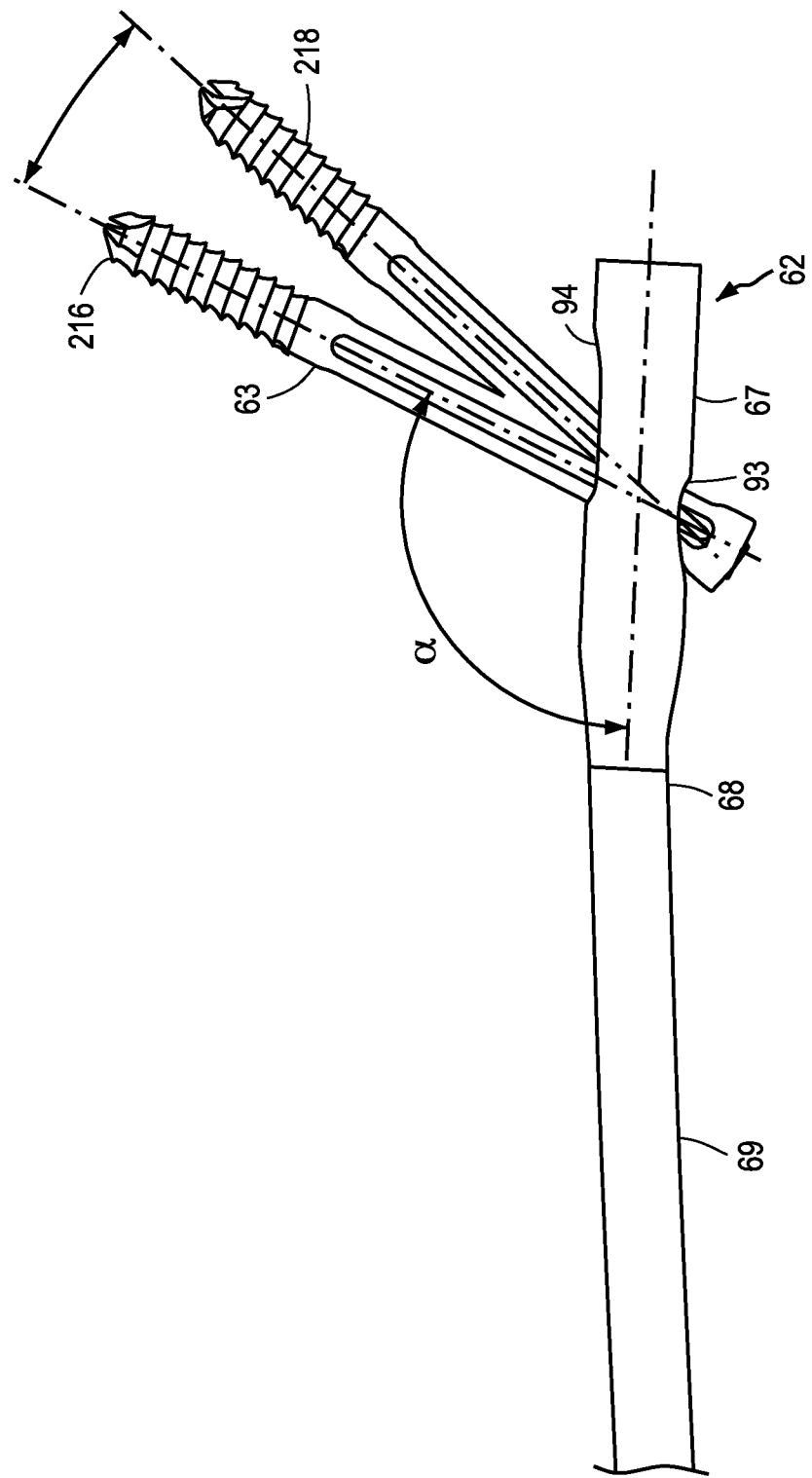

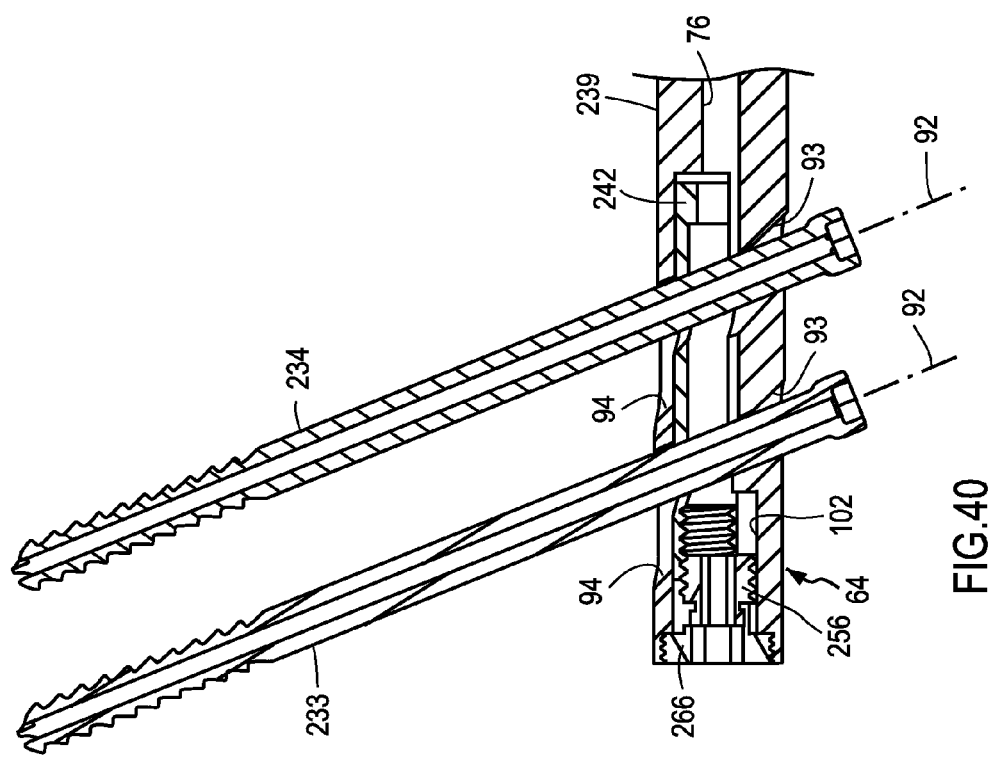

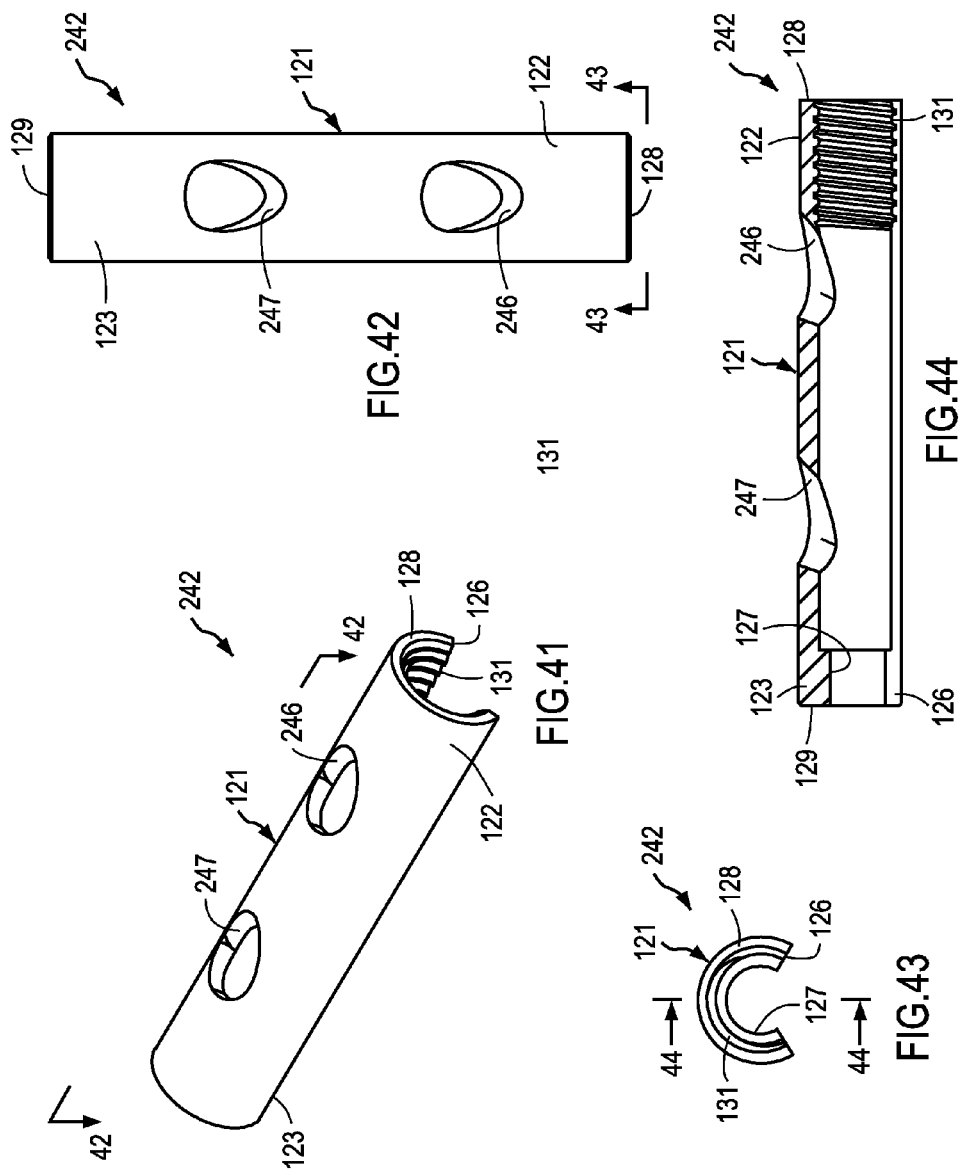

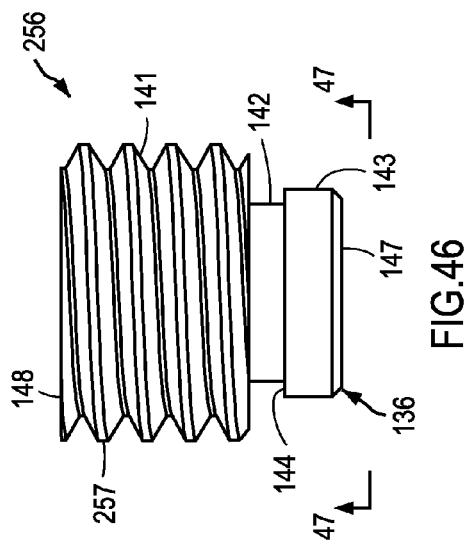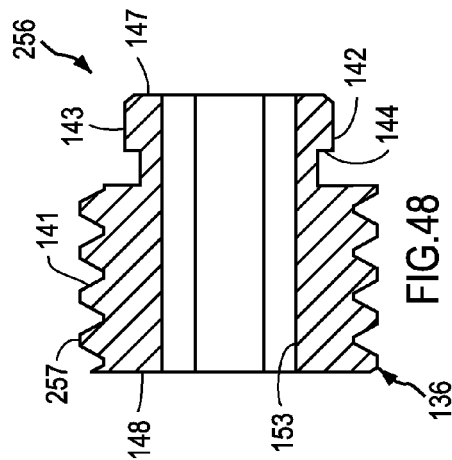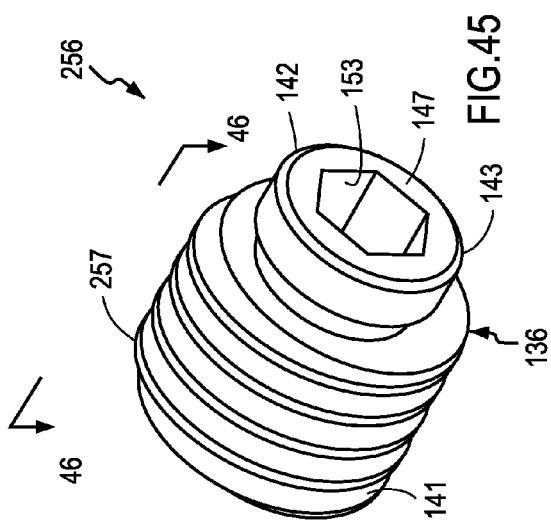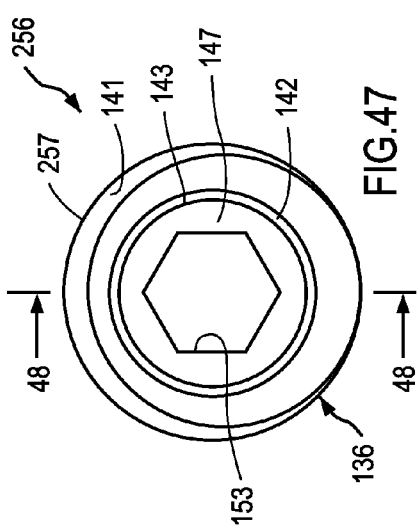

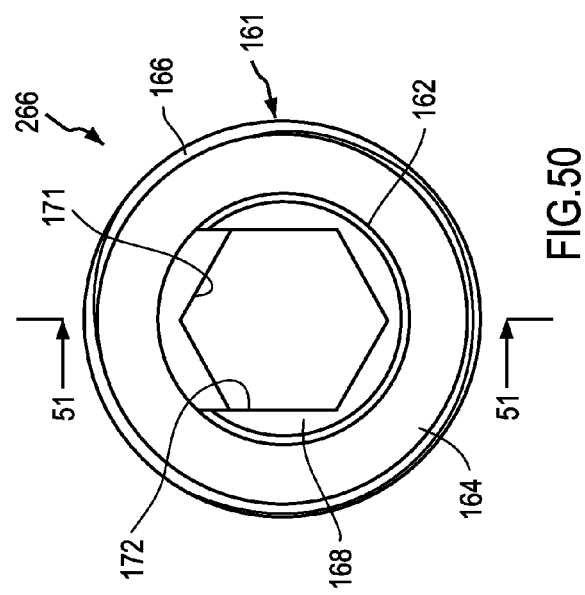
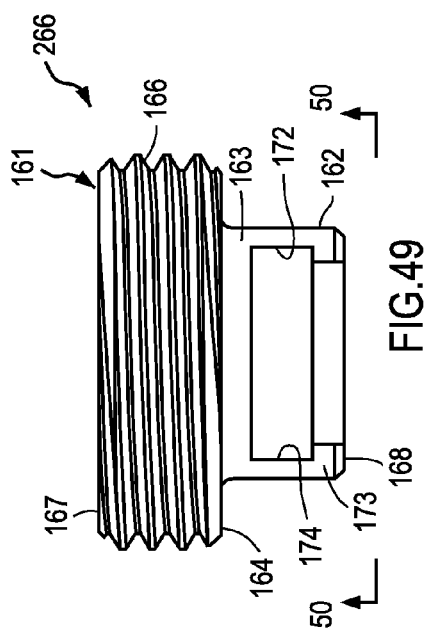
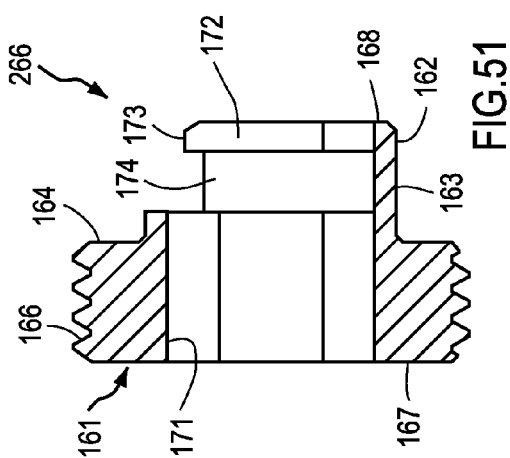

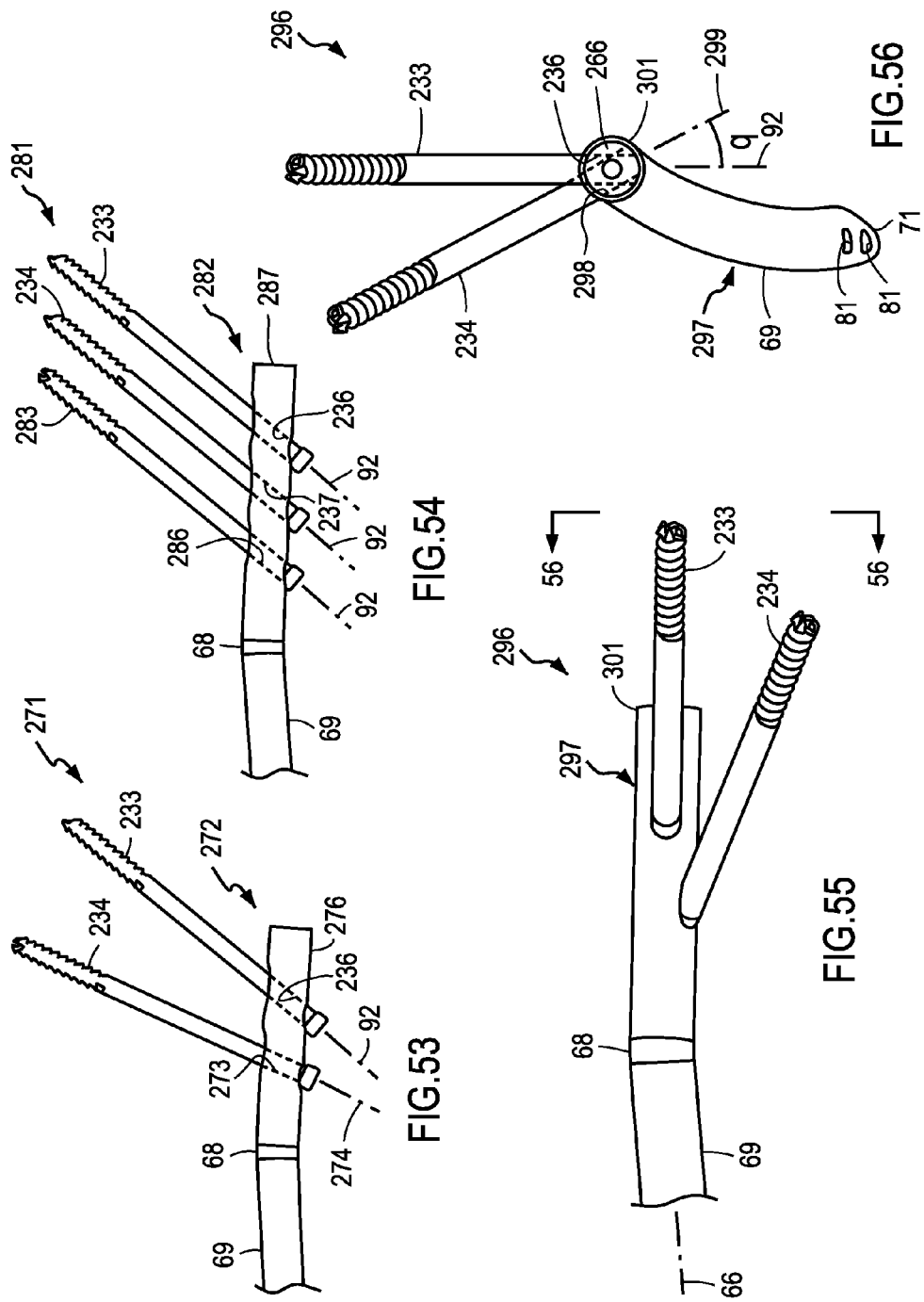

IMPLANTABLE DEVICE WITH PIVOTABLE FASTENER AND SELF-ADJUSTING SET SCREW

CROSS REFERENCE TO RELATED APPLICATION

This application claims priority to U.S. provisional patent application Ser. No. 61/800,921 filed Mar. 15, 2013, the entire content of which is incorporated herein by this reference.

FIELD OF THE INVENTION

The present invention relates to apparatus for affixing to bones and, more particularly, to an implantable devices with adjustable members for affixing to bones.

BACKGROUND OF THE INVENTION

There are a variety of devices for affixing to bones. Such devices can include, for example, spinal fasteners, bone plates and intramedullary rods used to treat femoral and other bone fractures. Peritrochanteric fractures of the femur, for example, have been treated with femoral rod assemblies that for example are inserted into the femoral canal to coapt the femur fractured parts. One or two angled cross-nails or locking screws are inserted through the femur and the proximal end of the intramedullary rod.

Currently available nails have been provided with static angled screws that transverse the femoral nail and then achieve adequate fixation strength in the head of the femur. They may also have slots in the nail that allow for dynamic controlled or uncontrolled compression of the fracture site in fractures of the subtrochanteric region and below, either with or without an over sleeve. Frequently, devices that treat femoral neck, intertrochanteric, and subtrochanteric fractures have varying static angles that necessitate an increased inventory to accommodate for varied static angles of the nail.

BRIEF DESCRIPTION OF THE DRAWINGS

The drawings described herein are for illustration purposes only and are not intended to limit the scope of the present disclosure in any way.

FIG. 5 is an exploded view of the head of the intramedullary rod with pivotable fastener of FIG. 1.

FIG. 6 is a side exploded view of the head of the intramedullary rod with pivotable fastener of FIG. 1 taken along the line 6-6 of FIG. 5.

FIG. 7 is a front view of the nail of the intramedullary rod with pivotable fastener of FIG. 1 with the components of the actuation mechanism removed.

FIG. 8 is a side view of the nail of FIG. 7 taken along the line 8-8 of FIG. 7.

FIG. 9 is a cross-sectional view of the nail of FIG. 7 taken along the line 9-9 of FIG. 7.

FIG. 10 is a cross-sectional view of the proximal portion of the nail of FIG. 7 taken along the line 10-10 of FIG. 8.

FIG. 11 is a side view of the head of the nail of FIG. 7 taken along the line 11-11 of FIG. 10.

FIG. 12 is a top end view of the nail of FIG. 7 taken along the line 12-12 of FIG. 11.

FIG. 13 is a cross-sectional view of the proximal portion of the nail of FIG. 7 taken along the line 13-13 of FIG. 12.

FIG. 14 is a perspective view of the insert of the intramedullary rod with pivotable fastener of FIG. 1.

FIG. 15 is a top view of the insert of FIG. 14 taken along the line 15-15 of FIG. 14.

FIG. 16 is an end view of the insert of FIG. 14 taken along the line 16-16 of FIG. 15.

FIG. 17 is a cross-sectional view of the insert of FIG. 14 taken along the line 17-17 of FIG. 16.

FIG. 18 is a perspective view of the end nut of the intramedullary rod with pivotable fastener of FIG. 1.

FIG. 19 is a side view of the end nut of FIG. 18 taken along the line 19-19 of FIG. 18.

FIG. 20 is bottom end view of the end nut of FIG. 18 taken along the line 20-20 of FIG. 18.

FIG. 21 is top end view of the end nut of FIG. 18 taken along the line 21-21 of FIG. 19.

FIG. 22 is a cross-sectional view of the end nut of FIG. 18 taken along the line 22-22 of FIG. 21.

FIG. 23 is a perspective view of the spindle of the intramedullary rod with pivotable fastener of FIG. 1.

FIG. 24 is a side view of the spindle of FIG. 23 taken along the line 24-24 of FIG. 23.

FIG. 25 is top end view of the spindle of FIG. 23 taken along the line 25-25 of FIG. 24.

FIG. 26 is bottom end view of the spindle of FIG. 23 taken along the line 26-26 of FIG. 24.

FIG. 27 is a cross-sectional view of the spindle of FIG. 23 taken along the line 27-27 of FIG. 25.

FIG. 32 is a perspective view of the fastener of the intramedullary rod with fastener of FIG. 1.

FIG. 33 is a side view of the fastener of FIG. 32 taken along the line 33-33 of FIG. 32.

FIG. 34 is an end view of the fastener of FIG. 32 taken along the line 34-34 of FIG. 33.

FIG. 35 is a cross-sectional view of the fastener of FIG. 32 taken along the line 35-35 of FIG. 34.

FIG. 36 is a front view of the proximal portion of the intramedullary rod with pivotable fastener of FIG. 1 showing the fastener in the first position of FIG. 1 relative to the intramedullary rod and the fastener in a second position relative pivoted counterclockwise to the intramedullary rod.

FIG. 40 is a cross-sectional view of the intramedullary rod with pivotable fasteners of FIG. 38 taken along the line 40-40 of FIG. 39.

FIG. 41 is a perspective view of the insert of the intramedullary rod with pivotable fasteners of FIG. 38.

FIG. 42 is a top view of the insert of FIG. 41 taken along the line 42-42 of FIG. 41.

FIG. 43 is an end view of the insert of FIG. 41 taken along the line 43-43 of FIG. 42.

FIG. 44 is a cross-sectional view of the insert of FIG. 41 taken along the line 44-44 of FIG. 43.

FIG. 45 is a perspective view of the spindle of the intramedullary rod with pivotable fasteners of FIG. 38.

FIG. 46 is a side view of the spindle of FIG. 45 taken along the line 46-46 of FIG. 45.

FIG. 47 is an end view of the spindle of FIG. 45 taken along the line 47-47 of FIG. 46.

FIG. 48 is a cross-sectional view of the spindle of FIG. 45 taken along the line 48-48 of FIG. 47.

FIG. 49 is a side view of the set screw of the intramedullary rod with pivotable fasteners of FIG. 38.

FIG. 50 is an end view of the set screw of FIG. 49 taken along the line 50-50 of FIG. 49.

FIG. 51 is a cross-sectional view of the set screw of FIG. 49 taken along the line 51-51 of FIG. 50.

FIG. 53 is a front view of a distal portion of a further embodiment of an intramedullary rod with pivotable fasteners of the present invention.

FIG. 54 is a front view of a distal portion of a yet another embodiment of an intramedullary rod with pivotable fasteners of the present invention.

FIG. 55 is a side view of a distal portion of a yet a further embodiment of an intramedullary rod with pivotable fasteners of the present invention.

FIG. 56 is an end view of the intramedullary rod with pivotable fastener of FIG. 55 taken along the line 56-56 of FIG. 55.

DETAILED DESCRIPTION OF THE INVENTION

In general, an apparatus or device is provided for treating fractures, nonunions or malunions of the femur or other bones of a mammalian body and includes an intramedullary rod or nail and at least one fastener carried by the rod. In addition to the foregoing, the apparatus or device can be used in any suitable procedure for fusing a joint or joints in a mammalian body, for example a fusion of the calcaneus to the talus and tibia and a fusion of the femur to the tibia. At least one opening is provided in the head of the apparatus for slidably receiving the one or more fasteners and permitting the fastener or fasteners to pivot relative to the head of the apparatus.

Figure 1:
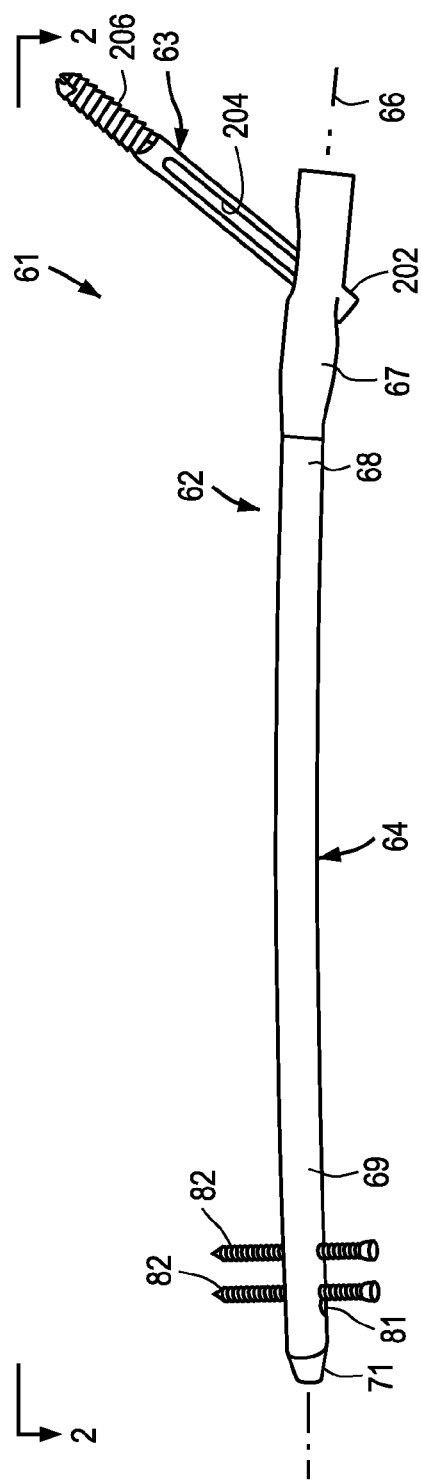
FIG. 1 is a front view of one embodiment of an intramedullary rod with pivotable fastener of the present invention.
Figure 2:
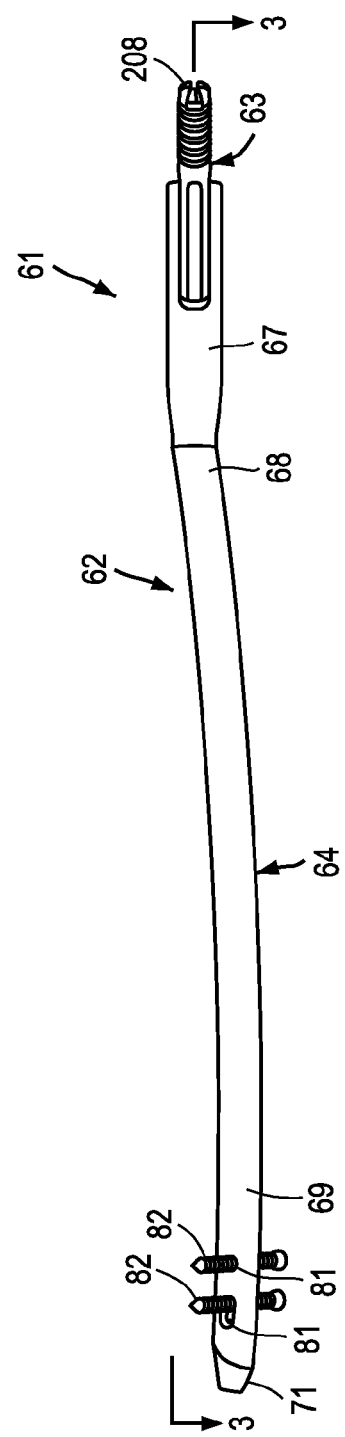
FIG. 2 is a side view of the intramedullary rod with pivotable fastener of FIG. 1 taken along the line 2-2 of FIG. 1.
Figure 3:
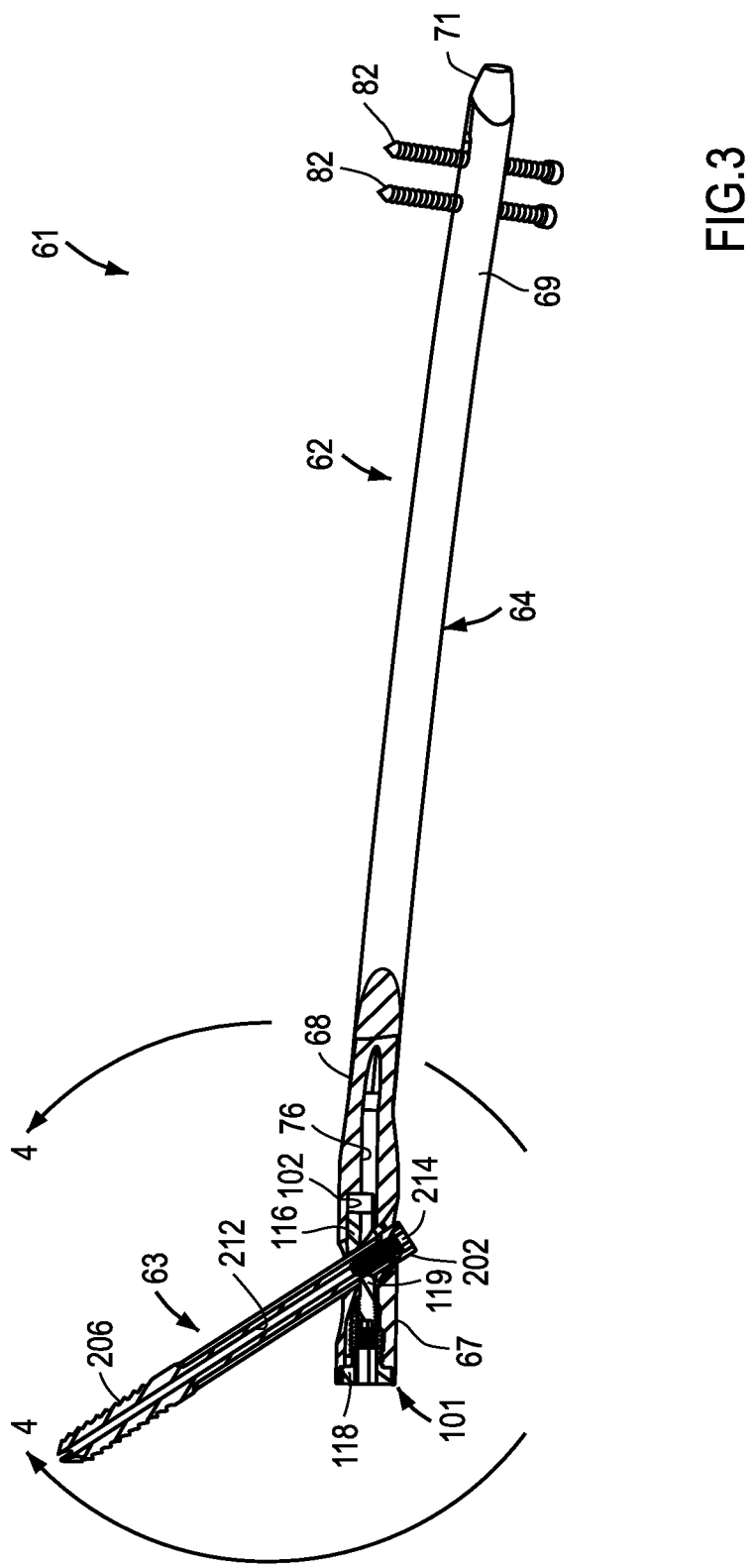
FIG. 3 is a rear view, partially sectioned, of the intramedullary rod with pivotable fastener of FIG. 1 taken along the line 3-3 of FIG. 2.

In one preferred embodiment, the apparatus 61 of the invention comprises an intramedullary rod 62 and a proximal fastener 63 pivotably carried by the proximal portion of the rod (see FIGS. 1-3). The proximal fastener 63 can be of any suitable type, including a fixation screw, a screw, a peg, a helical blade or any other fixation device, and for simplicity is referred to herein as a fixation screw. The femoral nail or rod 62 includes an elongate body 64 that extends along a longitudinal axis 66 and can have a proximal portion or head 67, a central portion or neck 68 and a distal portion or shaft 69 that terminates at a distal tip 71. The elongate body 64 may curve in at least one portion of the shaft or stem 69 to align the rod 62 along the length of the marrow canal of the femur when the rod is inserted in the femur. The elongate body 64 can be made from any suitable material such as stainless steel, titanium or another alloy and can have a length, dependent in part on the length in which the rod 62 is to be utilized, ranging from 180 to 500 centimeters. The head 67 of the nail 62 can have a length ranging from four to 15 centimeters and preferably ranging from eight to 12 centimeters and a diameter ranging from eight to 20 millimeters.

A longitudinally-extending passageway or bore 76, shown in part in FIGS. 3-4 and 9-10, can be provided and extends from a proximal opening 77 in the head 67 to an opening 78 in the tip of the stem for permitting the rod to slide along a guide wire during insertion of the rod into the femur. The curve of the longitudinal axis 66, and thus the curve of the stem 69 of the rod 62, can be through a single plane or through multiple planes. In the illustrated embodiment of nail 62, as shown in FIGS. 8, 10, 12 and 13, the curve of body 64 extends through multiple planes. At least one and in one embodiment first and second bores 81, which can extend perpendicular to the longitudinal axis 66, are provided in the distal end portion of the stem 69 adjacent the tapered tip 71 of the stem. The bores are sized to receive respective distal fasteners, such as fixation screws, screws, pegs, helical blades or any other suitable fixation devices, and in one embodiment such distal fasteners are in the form of fixation screws or screws 82 that can be fixed at an orthogonal angle relative to stem 69. In the illustrated embodiment and as shown in FIGS. 1-2 and 7-9, the distal-most bore 81 is elongated in its transverse direction, that is parallel to the longitudinal axis 66 of the stem 69, to permit the stem to be moved longitudinally relative to the respective distal fastener or fixation screw 82 before tightening of the fastener or screw to the underlying portion of the femur.

At least one transverse apertures or opening 91 is provided through the head 67 of the rod 62 and in one embodiment is angled toward the proximal end of the rod relative to longitudinal axis 66 for receiving the proximal fixation screw or fixation screw 63. More specifically, the one or more transverse apertures or holes 91 each pivotably receive a fixation screw 63 and allow for changing the angle made between the screw 63 and the nail 62. Each such aperture or first hole can extend through the head 67 in an angled direction relative to longitudinal axis 66 such that when the rod is in position within the marrow canal of the femur, axis 92 of the opening is directed toward the head of the femur (see FIG. 13). As can be seen from FIGS. 5, 6 and 10-13, the transverse aperture or aperture 92 in the head 67 can communicate with a first or lateral transverse opening 93, through which the respective fixation screw is inserted, and an opposite second or medial transverse opening 94, from which the distal portion of the screw extends. The medial transverse opening 94, as shown in FIGS. 5, 8, 11 and 13, can be elongate or oblong in a transverse direction that is parallel to longitudinal axis 66 of head 67 and body 64, so as to accommodate pivoting of the distal portion of the proximal fixation screw 63.

Figure 4:
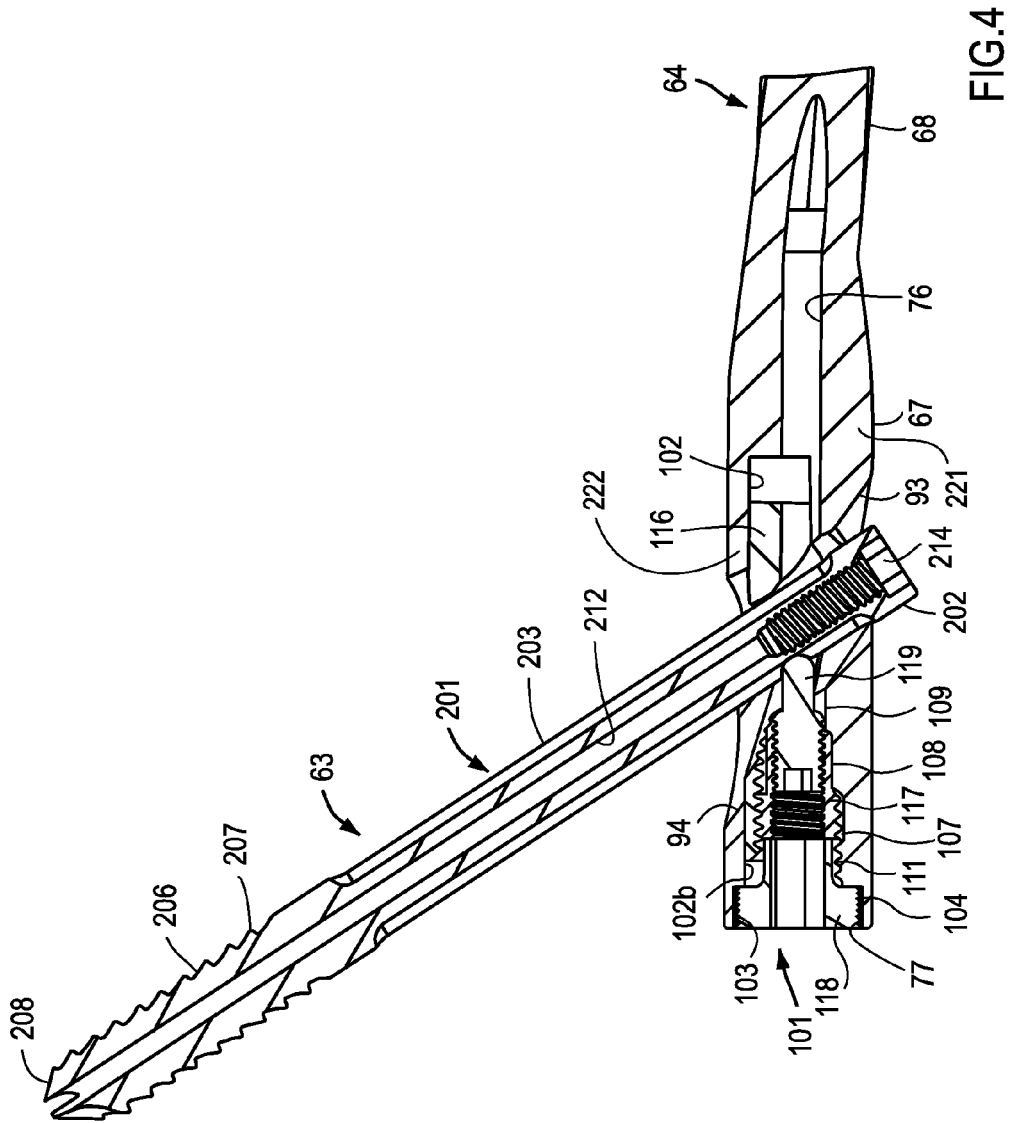
FIG. 4 is an enlarged cross sectional view of the intramedullary rod with pivotable fastener of FIG. 1 taken along the line 4-4 of FIG. 3.

The head 67 of rod 62 may include an actuation or adjustment mechanism or assembly 101 for selectively pivoting the proximal fixation screw 63 within the transverse aperture 91 (see FIGS. 4-31). In one embodiment, the actuation assembly 101 extends longitudinally of the head. In this regard, the proximal portion of the central passageway 76 of the nail 62 can be hollowed to form a longitudinally-extending proximal recess 102 in the head that communicates with a proximal opening 103 in the head. As illustrated in FIGS. 12 and 13, the recess 102 can have a proximal portion 102a, adjacent the proximal opening 103, and a segmented circular portion 102b that extends in cross section through any suitable angle preferably ranging from 180 to 240 degrees and illustrated in FIG. 12 as approximately 240 degrees, along the inside of the head 67 adjacent the medial transverse opening 94. Internal threads 104 can be provided in proximal portion 102a. The segmented circular portion or segmented portion 102b of recess 102 may be formed from an inner arcuate surface 105. The other side of the recess 102, that is the side opposite of segmented portion 102b, can be formed with a first shelf 107, a second shelf 108 and a third shelf 109 that can each extend further radially inwardly than the inner arcuate surface 105 of the segmented portion 102b and can have increasingly smaller radii relative to longitudinal axis 66 (see FIGS. 11-13). The proximal portion of the first shelf 107 can be optionally provided with internal threads 111, as shown in FIGS. 4, 9 and 10. A shoulder 112 can extend radially inwardly from first shelf 107 to second shelf 108 (see FIG. 13). The third shelf 109 may abut the lateral transverse opening 93, as shown in FIG. 11. Transversely aligned slots 110 may be provided on the proximal end of head 67 at proximal opening 103 for registering the nail 62 with an insertion jig, targeting device or other suitable device when placing or otherwise manipulating the nail within the targeted bone.

Although the actuation or adjustment mechanism 101 for pivoting the proximal fixation screw 63 can be of any suitable type, in one embodiment the mechanism 101 includes an insert or sleeve 116, a control element 117, an end or safety nut 118 and an alignment or set screw 119, as shown in the exploded views of FIGS. 5-6 and in the assembled view of FIG. 4. Each of these components can be made from any suitable material such as stainless steel.

Elongate insert or sleeve 116, as illustrated in FIGS. 14-17, may be formed from a tubular-like member 121 that can have a proximal portion 122 and a distal portion 123 and a longitudinally-extending opening 124 extending through one side. Sleeve 116 can have the shape of a cylinder with an elongate cutout 126 provided along one side thereof, opposite opening 124, that communicates with the longitudinal bore 127 extending therethrough from proximal or top end 128 and distal or bottom end 129. The planar top and bottom ends can extend parallel to each other. As such, sleeve 116 has a segmented circular or C shape when viewed from an end along its longitudinal axis, as shown in FIG. 16. Such transverse, cross-sectional configuration of sleeve 116 preferably approximates the cross-sectional configuration of the segmented circular portion 102b of the recess 102 in head 67 and can extend through an arc ranging from 100 to 360 degrees, preferably ranging from 180 to 240 degrees and illustrated in FIG. 16 as approximately 240 degrees. The elongate transverse opening 124 can be formed in the center of the insert. Such opening 124 may be oblong or elongate in shape and smaller than the medial transverse opening 94 provided in head 67 of the nail 62. The insert 116 may be provided with internal thread 131 extending through the bore 127 at the proximal portion 122 of the insert, such threads being adjacent the top or proximal end of the insert as shown in FIGS. 14 and 17. The insert can have a length ranging from 30 to 110 millimeters and can have an external radius sized to fit within head 67 of the nail 62. The distal portion of internal bore 127 that is the portion of the bore distal transverse opening 124, has a smaller internal diameter than the internal diameter of the proximal portion of the bore.

Control element 117 can be of any suitable type and in one embodiment includes a spindle or screw 117 formed from a cylindrical body 136 provided with a distal portion 137 of constant radius and can have a smooth outer cylindrical surface 138, a central portion 139 adjacent the distal portion and having external threads 141 extending radially outwardly relative to the distal portion and a proximal or neck portion 142 adjacent the central portion (see FIGS. 18-22). The neck portion can include a proximal flange 143 and an annular recess 144 disposed between the flange and the central portion 139 of the spindle or screw 117. The cylindrical body can further include a proximal or top end 147 and a distal or bottom end 148, as shown in FIG. 22. The planar ends 148 and 148 may extend parallel to each other. A central passageway or bore 151 can extend through the spindle. The distal portion of the central passageway may be provided with internal thread 152 and the proximal portion of the central passageway may be provided with any suitable cross-sectional configuration for serving as a drive socket 153. The spindle can have a length ranging from five to 50 millimeters and preferably approximately 15 millimeters.

End nut 118 can be formed from a cylindrical body 161 provided with a distal portion 162 of constant radius and a smooth outer surface 163 and a proximal portion 164 adjacent the distal portion and having external threads 166 extending radially outwardly relative to the distal portion (see FIGS. 23-27). The cylindrical body can further include a proximal or top end 167 and a distal or bottom end 168, as shown in FIG. 27. Planar ends 167 and 168 can extend parallel to each other. A central passageway or bore 171 can extend longitudinally through the end nut between ends 167 and 168 and at least the proximal portion of the bore 171 can be provided with any suitable cross-sectional configuration for serving as a drive socket. The distal end portion of the end nut may be provided with a recess or socket 172 that can be in communication with bore 171 and be side opening onto the outer cylindrical surface 163 of the distal portion 162. The socket 172 can be sized and configured for cooperatively receiving the neck portion 142 of the spindle 117 and may include a partial annular flange 173, shown most clearly in FIG. 24, extending radially inwardly for partially seating in the annular recess 144 of the spindle and a partial annular recess 174 extending radially outwardly relative to the flange for receiving part of the proximal, annular flange 143 of the spindle. The end nut can have a length ranging from five to 50 millimeters and preferably approximately 15 millimeters.

Figure 29:
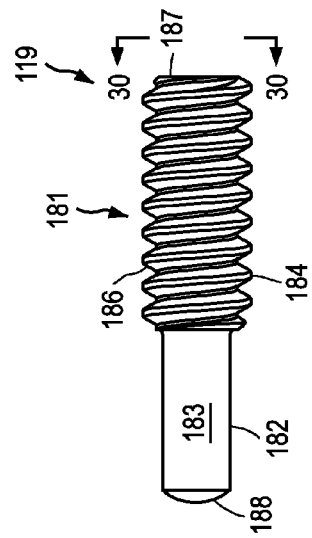
FIG. 29 is a side view of the set screw of FIG. 28 taken along the line 29-29 of FIG. 28.
Figure 31:
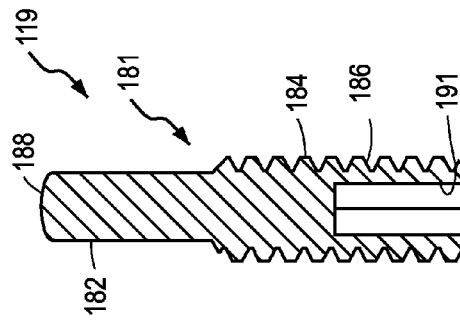
FIG. 31 is a cross-sectional view of the set screw of FIG. 28 taken along the line 31-31 of FIG. 30.
Figure 28:
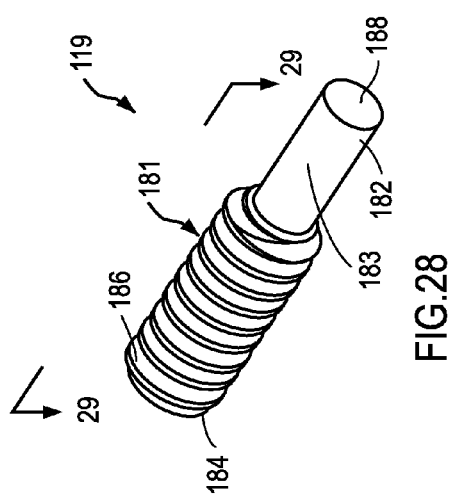
FIG. 28 is a perspective view of the set screw of the intramedullary rod with fastener of FIG. 1.
Figure 30:
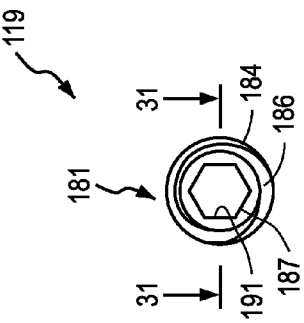
FIG. 30 is an end view of the set screw of FIG. 28 taken along the line 30-30 of FIG. 29.

Set screw 119 can be formed from a cylindrical body 181 provided with a distal portion 182 of constant radius and a smooth outer surface 183 and a proximal portion 184 adjacent the distal portion and having external threads 186 extending radially outwardly relative to the distal portion (see FIGS. 28-31). The cylindrical body 181 can further include a proximal or top end 187 and a distal or bottom end 188, as shown in FIG. 29. A drive socket 191 of any suitable cross-sectional configuration may extend longitudinally through at least a portion of the cylindrical body and open at the top end 187 of the body. The bottom end 188 of the body can be blunted. The set screw can have a length ranging from five to 60 millimeters and preferably approximately 20 millimeters.

Proximal fastener 63 for use in the head 67 of the intramedullary rod 62 can be of any suitable type and in one embodiment is made from an elongate cylindrical body 201 or spiral blade (not shown) having a length ranging from 40 to 200 millimeters and a diameter ranging from two to 20 millimeters (see FIGS. 32-35). In the illustrated embodiment, the fastener is a fixation screw formed from a body having a threaded portion and a smooth portion. The elongate body 201 can be formed from any suitable material such as stainless steel and include a proximal portion 202 having any outer cylindrical or irregular-shaped surface 203. The proximal portion 202 may be provided with a plurality and as shown four longitudinally-extending slots 204 extending through the surface 203 in circumferentially-spaced apart positions. Distal portion 206 of the body 201 may be provided with external threads 207 that extend to a sharpened distal end or tip 208 of the body. Alternatively, the distal portion 206 of the body 207 may be irregularly shaped or flat (not shown). The body can further have a proximal end 211 and be provided with a central bore 212 that extends longitudinally through the body from the proximal end 211 to the distal end 208 (see FIG. 35). The proximal end of the central bore 212 may be provided with internal threads 213 and be formed with a drive socket 214 of any suitable type for facilitating connection of the proximal fixation screw to a drive tool of any suitable type.

Actuation assembly or mechanism 101 loaded into the head 67 of the nail 62 in any suitable manner. In one method of assembly, insert or sleeve 116 is slidably inserted through the proximal opening 103 of the head and slidably seated in the segmented circular portion 102b of the recess 102 in the head so as to extend longitudinally of the head 67. The transverse opening 124 in the insert 116 is in general registration with the medial transverse opening 94 in the head 67. The proximal or neck portion 142 of spindle 117 is seated in the socket 172 formed in the distal portion 162 of end nut 118 so that the end nut and spindle are coaxial along the central longitudinal axes of the end nut and spindle. The combined spindle 117 and end nut 118 assembly are loaded into the head 67 by introducing the distal portion 137 of the spindle into the proximal opening 103 in the head. A suitable drive tool (not shown) can be used to engage the drive socket in the central bore 171 at the proximal portion 164 of the end nut to rotate the end nut within the internal threads 104 adjacent the proximal opening 103 in the head so as to move the end nut 118, and the spindle 117 captured thereby, longitudinally into the recess 102 of the head until the spindle seats is the distal portion of the first shelf 107 against shoulder 112 extending between the first shelf 107 and the second shelf 108. As spindle 117 is moved distally within the recess 102 of the head 67, the external threads 141 of the spindle engage the internal threads 131 on the proximal portion 122 of insert 116. The spindle can be moved longitudinally into threaded engagement with the insert by engagement of the drive socket 153 in the proximal or neck portion 142 of spindle 117 with a suitable drive tool and clockwise rotation of the spindle within the recess 102 of the head 67.

The set screw 119 can thereafter be introduced through central bore 171 of the end nut 118 and into central bore 151 of the spindle 117 until the external threads 186 provided on the proximal end portion 184 of the set screw engage the internal threads 152 provided within the distal portion 137 of the spindle. A suitable drive tool may be used to engage the drive socket 191 in the proximal portion 184 of the set screw 119 to move the set screw distally relative to the spindle 117 by the rotational engagement of the external threads 186 on the set screw with the internal threads 152 of the spindle.

The distal portion 182 of the set screw can thus be moved distally of the spindle 117 into the transverse aperture 91 in head 67 of the nail 62.

Figure 37:
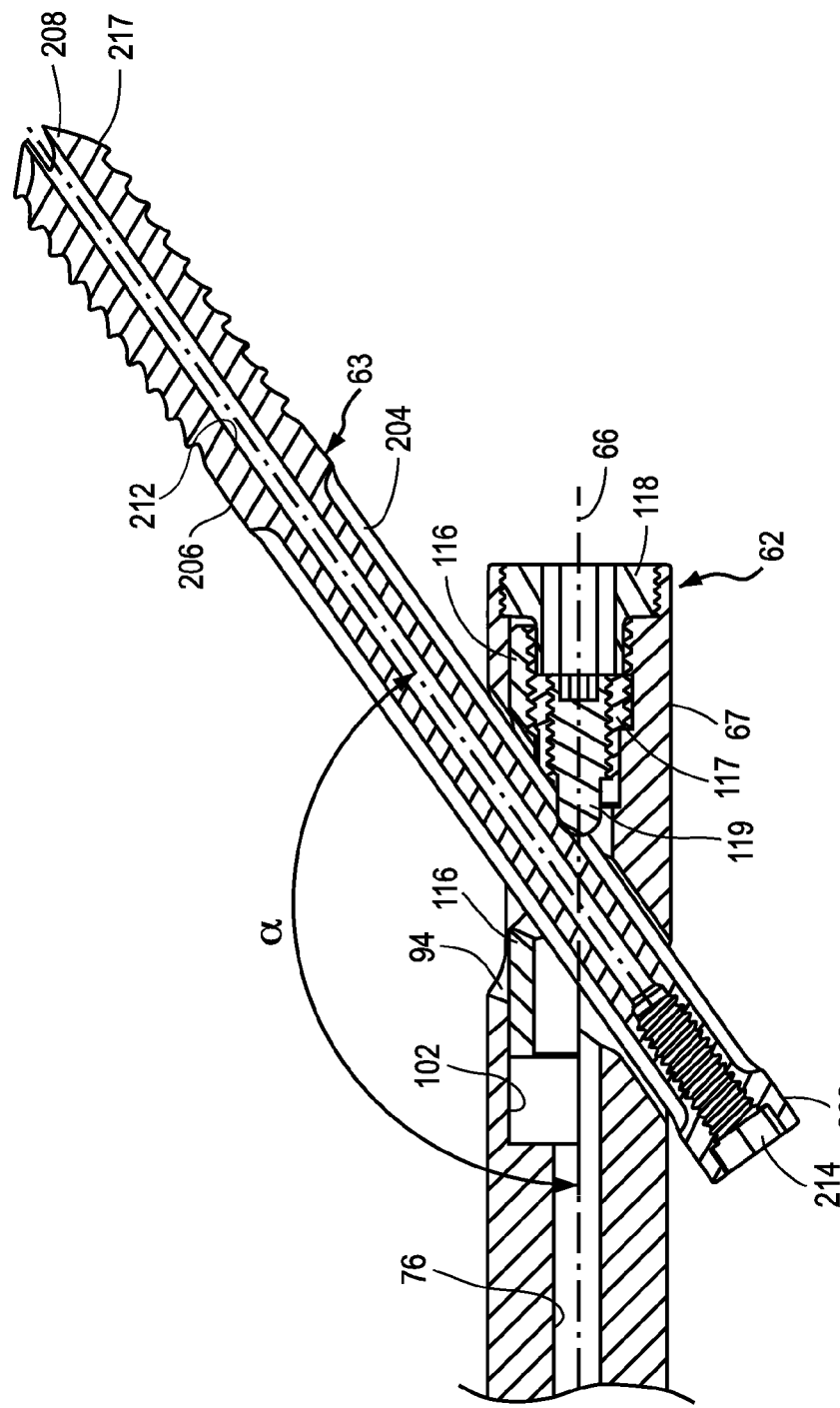
FIG. 37 is a cross-sectional view of the proximal portion of the intramedullary rod and pivotable fastener of FIG. 1 showing the fastener in a third position relative to the intramedullary rod.

Upon insertion of the proximal fixation screw 63 into the transverse aperture 91 of the head 67, and through the transverse opening 124 in the insert 116, the fixation screw can be pivoted about a transverse axis of the head through an angle of up to 70 degrees and preferably approximately 30 degrees relative to the nail 62. In one embodiment, illustrated in the figures, the fixation screw 63 is pivotable about a transverse axis defined the distal surface of first or lateral transverse opening 93 (see FIGS. 4 and 13) between a first position 216, extending at an angle α of approximately 115 degrees relative to the stem 69 of the nail and shown in FIG. 36, and a second position 217, extending at an angle α of approximately 145 degrees relative to the stem of the nail and shown in FIG. 37. The transverse or pivot axis of fixation screw 63, which in one embodiment is orthogonal to longitudinal or central axis 66 of the nail 62 and to transverse axis 92 of the aperture, is in a first side portion 221 of the head 67 relative to axis 66. Such first side portion 221 is on one side of the central axis 66. The fixation screw is shown in an intermediate position 218, extending at an angle α of approximately 130 degrees relative to the stem of the nail, in FIG. 36. To so pivot the fixation screw, in one procedure the physician rotates the spindle 117 within the head 67, for example by engaging the drive socket 153 in the neck portion 142 of the spindle with a suitable drive tool, so that the external threads 141 on the central portion 139 of the spindle that engage the internal threads 131 within the insert 116 cause the insert to move proximally within the head from a first or distal position in the segmented circular portion (not shown) to a second or proximal position in the segmented circular portion, illustrated in FIG. 37. The distal end of the transverse opening 124 in the insert 116 engages the fixation screw 63 in a second side portion 222 of the head relative to axis 66 during proximal movement of the insert within the head 67 to cause the fixation screw to pivot within the medial transverse opening 93 of the transverse aperture 91 of the head. Such second side portion 22 is on the opposite side of the central axis 66 from the first side portion 221. When in its operational position within the head 67, shown in FIG. 37, the spindle 117 can rotate freely relative to the head and the end cap 118. The set screw 119 can be rotated distally with the spindle 117 so that the blunted end 188 of the set screw seats within one of the longitudinal slots 294 formed in the proximal portion 202 of the fixation screw 63 so as to rotatably lock the fixation screw relative to the head 67 of the intramedullary rod 62 and thus inhibit undesirable further advancement or withdrawal of the screw 63 relative to the rod 62.

Although the actuation mechanism 101 of intramedullary rod 62 has been shown and described with a longitudinally movable insert or sleeve 116 disposed within the nail, it is appreciated that an insert or sleeve slidably disposed on the outside of the nail 62 can be provided for pivoting the fixation screw 62 relative to the nail.

It is further appreciated that other embodiments of the intramedullary rod of the present invention, for example with any plurality of pivotable fasteners can be provided. Another apparatus 231 is illustrated in FIGS. 38-52 and can include an intramedullary rod 232 substantially similar to rod 62. Like reference numerals have been utilized to describe like components of rods 62 and 232. The intramedullary rod 232 has any suitable first and second proximal fasteners, shown as first and second proximal fixation screws 233 and 234 that can each be substantially identical to proximal fixation screw 63, pivotably received within respective first and second transverse apertures 236 and 237 that can each be substantially identical to transverse aperture 91 and extend along respective axes 92. The first and second fasteners 233 and 234 extend parallel to each other, may or may not be of the same length and may or may not be of the same type of fastener. For example, the first fastener 233 may be a screw and the second fastener 234 may be a peg or blade. The apertures 236 and 237 are provided in a head 239, substantially similar to head 67, of the rod 232.

An actuation mechanism or assembly 241, substantially similar to actuation mechanism 101, can be provided with the head 239 of the rod 232. Actuation mechanism 241, shown in an assembled position in FIG. 40, can include an insert or sleeve 242 substantially similar to the insert 116 of mechanism 101 but having first and second transverse apertures 246 and 247 similar to transverse aperture 91 of the sleeve 116 and extending at an angle to the longitudinal axis of the nail for respectively receiving and pivoting the first and second fixation screws 233 and 234 (see FIGS. 41-44). The axes 92 of the first and second transverse apertures 246 and 247 can be parallel to each other but may also not be parallel to each other. The insert 242 can have a length ranging from 20 to 120 millimeters and an external radius sized to fit within head 239 of the nail 232. A spindle 256 can be provided that is substantially similar to the spindle 117 but formed without the distal portion 137 of spindle 117 (see FIGS. 45-48). Instead, spindle 256 of the dual fixation screw rod 232 of FIGS. 38-52 has a proximal or neck portion 142 and a distal portion 257 substantially similar to central portion 139 of the spindle 117. The spindle 256 can have a length ranging from five to 30 millimeters. An end cap or nut 266 substantially similar to end nut 118 but shorter in length can be further provided (see FIGS. 49-51). The end nut can have a length ranging from three to 30 millimeters. The proximal portion 142 of spindle 256 is shown as being captured or seated in socket 172 in the distal portion 162 of end nut 266 in FIG. 52 so that the spindle and end cap are coaxially aligned in their operational positions relative to each other.

The components of actuation assembly 241 can be loaded into head 239 of dual fixation screw rod 232, and operated therein with respect to first and second proximal fixation screws 233 and 234, in substantially the same manner as discussed above with respect to apparatus 61. Sleeve 242 is shown in FIG. 40 in its distal position. The inclusion in apparatus 241 of the second fixation screw 234 minimizes the need for a set screw, such as set screw 119, and preferably eliminates the need for such a set screw. In this regard, the second proximal fixation screw is included in the means or mechanism of the rod 232 for preventing rotation of the head of the femur relative to the first proximal fixation screw 233 during use of rod 232. It is appreciated that other means, such as a nail, peg, blade or bolt, can be included in an intramedullary rod of the present invention for inhibiting rotation of the head of the femur relative to the first fixation screw. The optional second aperture 237 and second proximal fixation screw 234 allow sliding compression so as to prevent rotation and to adapt the apparatus or device to a variety of applications.

A further embodiment of the intramedullary rod with pivotable fasteners of the present invention is illustrated in FIG. 53 wherein an apparatus 271 substantially similar to apparatus 61 and 231 is provided. Like reference numerals have been used to describe like components of apparatus 61, 231 and 271. Intramedullary rod or nail 272 of the apparatus 271 is substantially similar to rods 62 and 232 and has any suitable first and second proximal fasteners, shown as first and second proximal fixation screws 233 and 234. The first screw 233 is pivotably received within first transverse aperture 236 extending along axis 92. The second screw 234 is pivotably received within a second transverse aperture 273 extending along an axis 274. The aperture 273 can be substantially identical to transverse aperture 236 except that axis 274 of the second transverse aperture 273 is not parallel to the axis 92 of the first transverse aperture 236. The first and second fasteners 233 and 234 extend nonparallel to each other, may or may not be of the same length and may or may not be of the same type of fastener. The apertures 236 and 273 are provided in a head 276 of the rod 272 that is substantially similar to head 239 of rod 232. An actuation mechanism or assembly (not shown) substantially similar to actuation mechanism 241 but modified to provide for the nonparallel disposition of apertures 236 and 273 is provided.

Another embodiment in the form or apparatus 281 is illustrated in FIG. 54 and can include an intramedullary rod 282 substantially similar to rods 62 and 232. Like reference numerals have been utilized to describe like components of rods 62, 232 and 282. The intramedullary rod 282 has any suitable first, second and third proximal fasteners, shown as first, second and third proximal fixation screws 233, 234 and 283, pivotably received within respective first, second and third transverse apertures 236, 237 and 286. The third proximal fixation screw 283 can be identical to one or both of first and second proximal fixation screws 233 and 234, and the third transverse aperture 286 can be identical to one or both of first and second transverse apertures 236 and 237. The first, second and third fasteners 233, 234 and 283 may or may not extend parallel to each other, may or may not be of the same length and may or may not be of the same type of fastener. In the illustrated embodiment, the fasteners 233, 234 and 283 extend parallel to each other. The apertures 236, 237 and 286 are provided in a head 287 of the rod 282 that is substantially similar to head 239 of rod 232. An actuation mechanism or assembly (not shown) substantially similar to actuation mechanism 241 but modified to provide for the third transverse aperture 286 can be provided.

Figure 38:
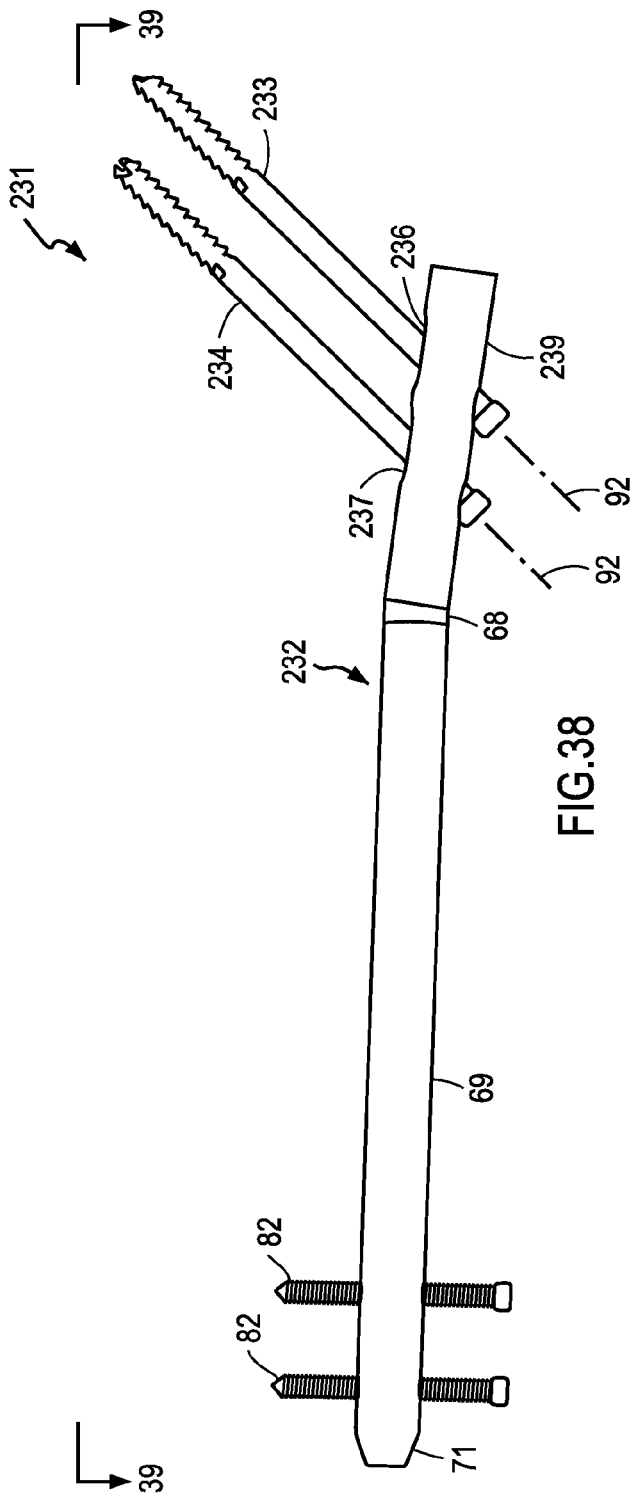
FIG. 38 is a front view of another embodiment of an intramedullary rod with pivotable fasteners of the present invention.
Figure 39:
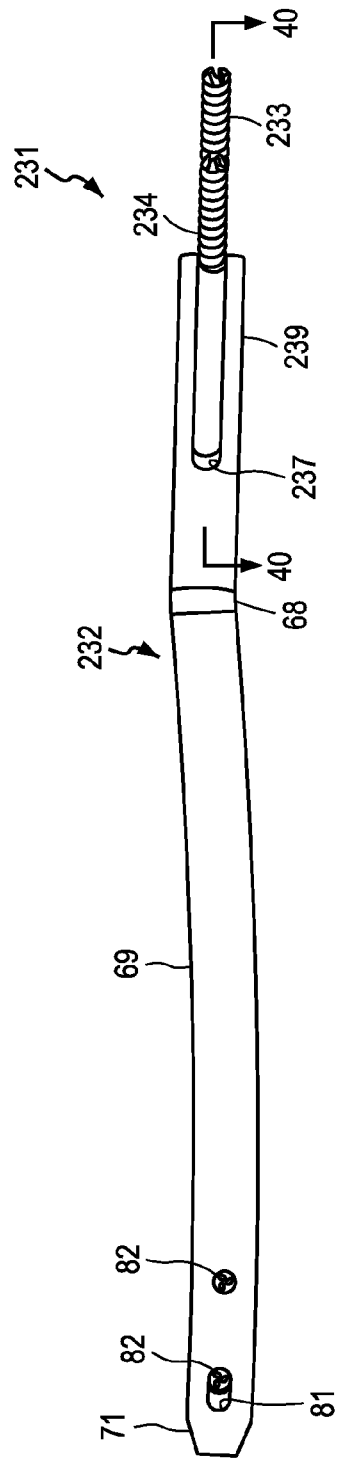
FIG. 39 is a side view of the intramedullary rod with pivotable fasteners of FIG. 38 taken along the line 39-39 of FIG. 38.
Figure 52:
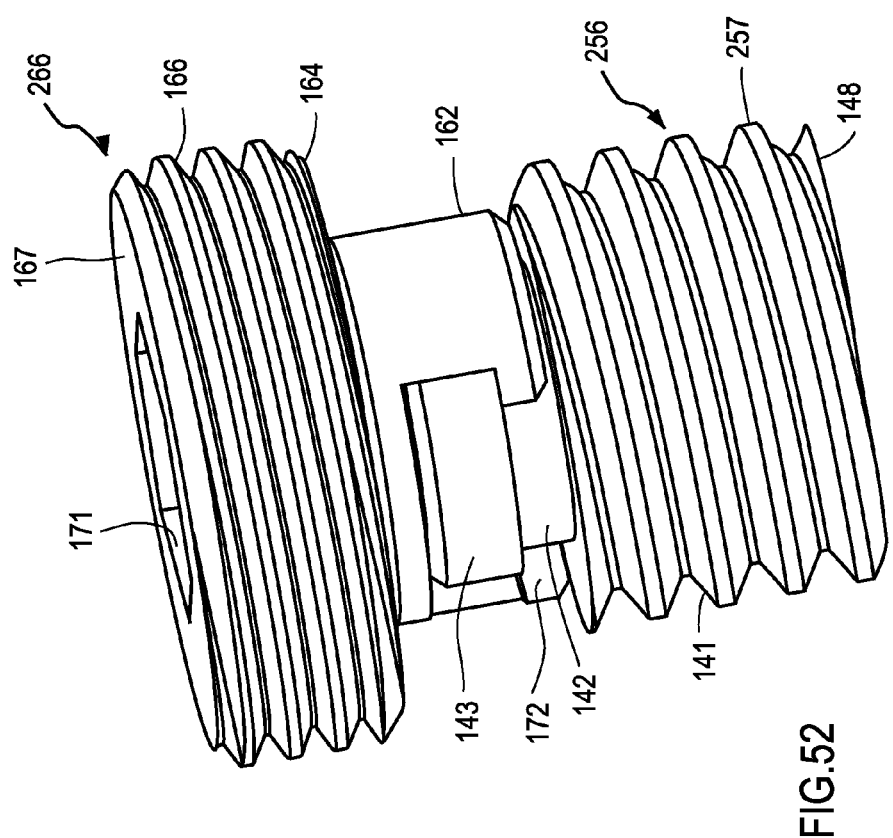
FIG. 52 is a perspective view of the set screw of FIG. 49 mounted on the spindle of FIG. 45.

Yet a further embodiment of the intramedullary rod with pivotable fasteners of the present invention is illustrated in FIGS. 55-56 wherein an apparatus 296 substantially similar to apparatus 61 and 231 is provided. Like reference numerals have been used to describe like components of apparatus 61, 231 and 296. Intramedullary rod or nail 297 of the apparatus 296 is substantially similar to rods 62 and 232 and has any suitable first and second proximal fasteners, shown as first and second proximal fixation screws 233 and 234. The first screw 233 is pivotably received within first transverse aperture 236 extending along axis 92. The second screw 234 is pivotably received within a second transverse aperture 298 extending along an axis 299. The second transverse aperture 298 can be substantially identical to the first transverse aperture 236 except that axis 299 of the second transverse aperture 298 is not parallel to the axis 92 of the first transverse aperture 236. More specifically, axis 299 is circumferentially angled about the longitudinal axis 66 of rod 297 relative to axis 92, as shown in FIG. 56 by angle θ. Angle θ can be any suitable number. Axes 92 and 299 can extend at the same angle relative to longitudinal axis 66, such as axes 92 of rod 232 as shown in FIG. 38, or can extend at different angles relative to longitudinal axis 66, such as axes 92 and 274 of rod 272 as shown in FIG. 53. The first and second fasteners 233 and 234 may or may not be of the same length and may or may not be of the same type of fastener. The apertures 236 and 298 are provided in a head 301 of the rod 297 that is substantially similar to head 239 of rod 232. An actuation mechanism or assembly (not shown) substantially similar to actuation mechanism 241 but modified to provide for the different circumferential alignment of apertures 236 and 298 is provided.

It can be seen from the foregoing various embodiments of the intramedullary rod with pivotable fasteners of the present invention that such fasteners can be of any suitable number. Where multiple fasteners are provided, the fasteners can extend parallel to each other or at various angles to each other relative to the longitudinal axis and about the longitudinal axis of the nail. Extrapolations of the illustrated apparatus can be provided, for example where three nonparallel fasteners are provided, where multiple fasteners are circumferentially aligned relative to each other about the longitudinal axis of the rod but spaced the same distance from the proximal end of the rod or where two or more first fasteners are circumferentially aligned relative to such longitudinal axis and one or more second fasteners are circumferentially spaced apart about such longitudinal axis relative to the first fasteners.

Although the apparatus of the invention has been illustrated as having a separate transverse aperture in the rod for each fastener, it is appreciated that multiple fasteners can pivotably extend through a single transverse aperture. In one such embodiment in which a single transverse aperture receives two fasteners, one or both of the aperture in the rod and the aperture in the actuation mechanism has a configuration that narrows between two end portions of such aperture such that the two fasteners extending through respective end portions of such aperture are separated from each other by the narrowed material of the rod and/or the actuation mechanism.

Figure 57:
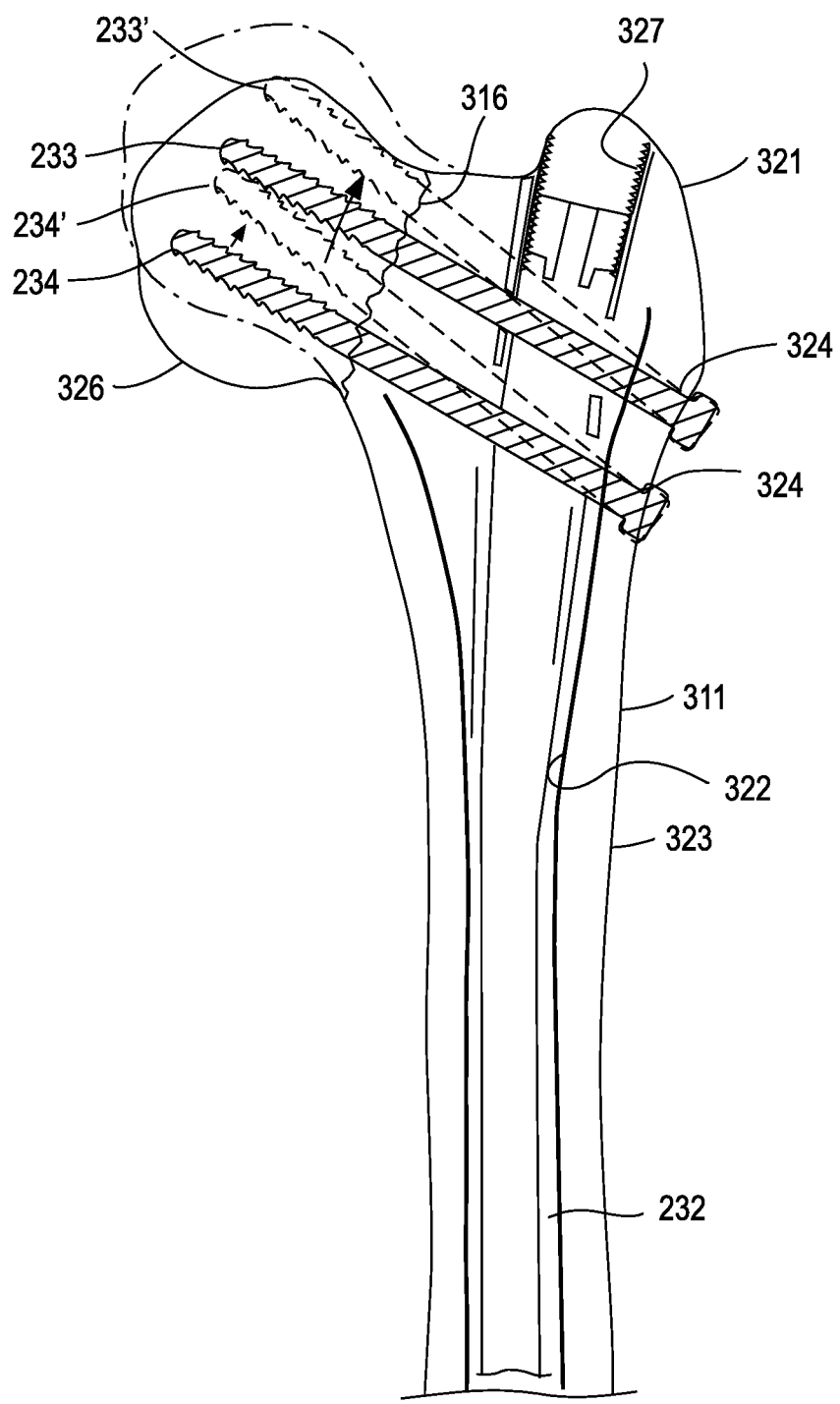
FIG. 57 is a schematic front view of the intramedullary rod with pivotable fasteners of FIG. 38 disposed in a femur to repair a femoral neck fracture.
Figure 58:
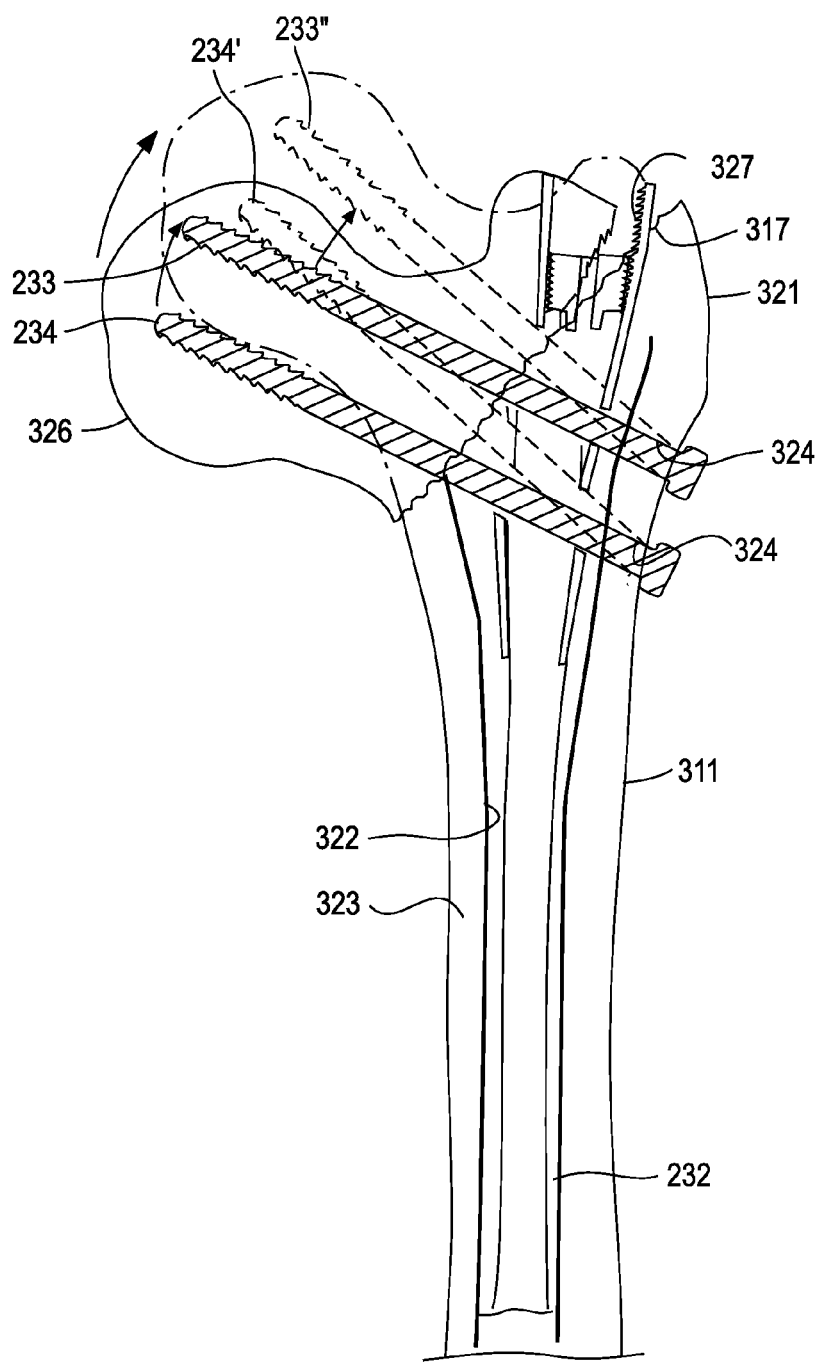
FIG. 58 is a schematic front view of the intramedullary rod with pivotable fasteners of FIG. 38 disposed in a femur to repair an intertrochanteric fracture.
Figure 59:
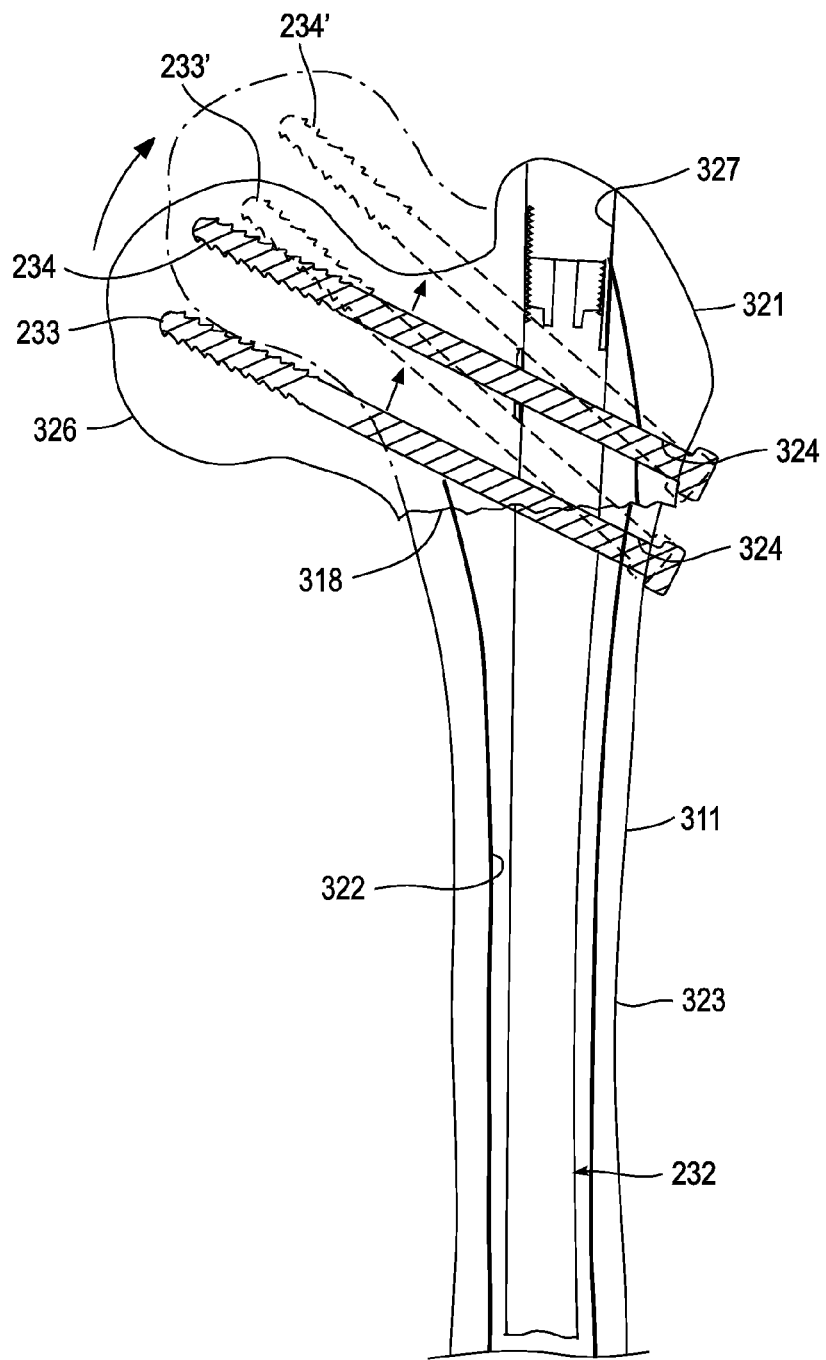
FIG. 59 is a schematic front view of the intramedullary rod with pivotable fasteners of FIG. 38 disposed in a femur to repair a subtrochanteric fracture.

Several procedures for utilizing the intramedullary rod with pivotable fixation screws of the present invention are illustrated in FIGS. 57-59, where apparatus 231 with dual fixation screw rod 232 is shown in use to repair peritrochanteric fractures of a femur 311. More specifically, 232 rod is shown repairing a femoral neck fracture 316, an intertrochanteric fracture 317 and a subtrochanteric fracture 318, respectively, in FIGS. 57-59. Previous to the procedure of the invention, the rod 233 was introduced through the greater trochanter 321 into the medullary canal 322 in the shaft 323 of the femur. Suitable holes 324 were made in the side of the greater trochanter to allow insertion of the first and second fixation screws 233 and 234 into the lateral transverse openings 93 of the respective first and second transverse apertures 236 and 237 in the head 239 of the rod. The fixation screws were thereafter screwed into the head 326 of the femur 311. In each instance, however, further adjustment of the head of the femur may be required either because the fracture is malreduced, the entry point for the rod in the greater trochanter was too lateral or a combination of the foregoing. In one procedure of the invention, a suitable drive (not shown) element is introduced through the entry point 327 in the femur into the proximal opening 103 in the head 239 of the nail 232 and through the end nut 266 so as to seat within the drive socket 153 in the neck portion 142 of the spindle 256. The spindle 256 is rotated by the drive element, for example in a clockwise direction, so that the external threads 141 on the spindle engaged with the internal threads 131 on the proximal portion 122 of the insert or sleeve 242 and cause the insert 242 to slide or move proximally within the head 239 and thus cause each of the first and second proximal fixation screws 233 and 234 to pivot upwardly toward the head 239 of the rod, that is in a clockwise direction in FIGS. 57-59, until the fracture is reduced and the head 326 of the femur 311 is brought out of varus and thus properly positioned relative to the remainder of the femur, as shown in phantom lines in FIGS. 57-59. The first and second proximal fixation screws are identified as 233' and 234' in FIGS. 57-59 when in their second position in which they have been pivoted upwardly toward the head 239 of the rod 232.

The capture of the neck portion 142 of the spindle 256 in the socket 172 of the end nut 266 inhibits movement of the spindle 256 from its coaxial position with the longitudinal axis of the head 239 and thus inhibits undesirable movement of the insert 242, and the first and second fixation screws 233 and 234 retained in position by the insert, that may result from such misalignment of the spindle 256 in the head 239 of the rod. The second fixation screw 234 inhibits, if not prevents, rotation of the femoral head 326 relative to the first fixation screw 233.

It is appreciated that the apparatus of the invention can include more than two proximal fasteners to fixate head 326 of the femur, or a portion of any other suitable bone, and be within the scope of the present invention.

Figure 61:
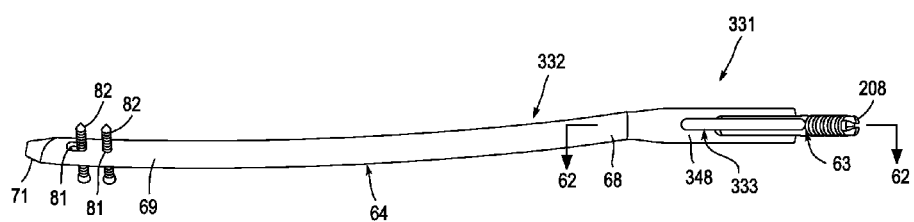
FIG. 61 is a side view of the intramedullary rod with pivotable and fixed fasteners of FIG. 60 taken along the line 61-61 of FIG. 60.
Figure 62:
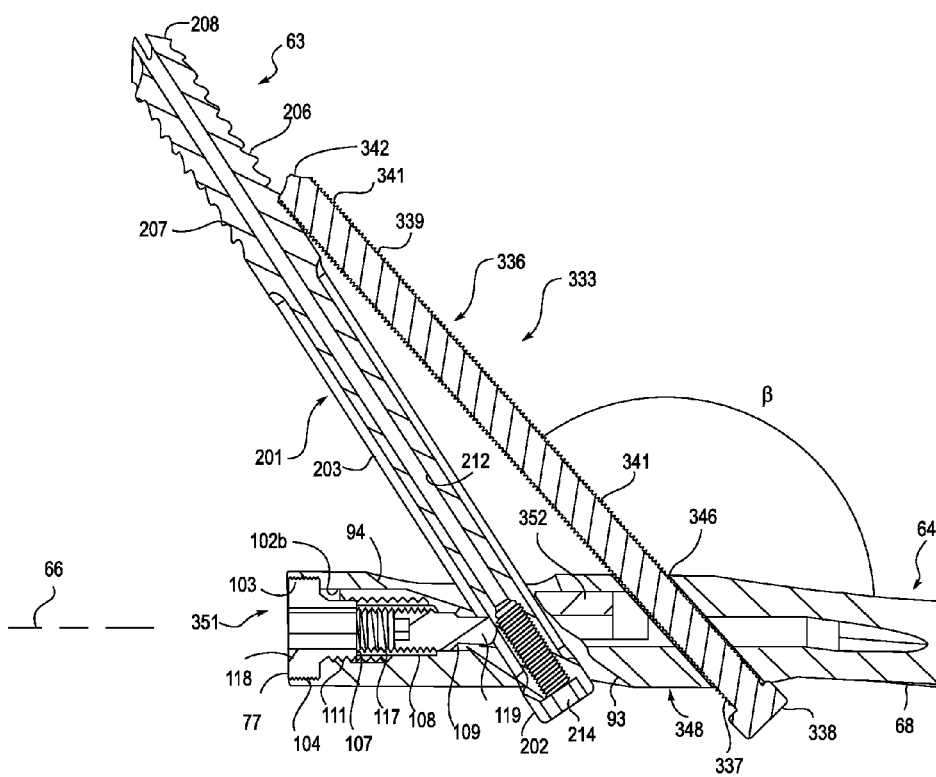
FIG. 62 is an enlarged cross sectional view of the intramedullary rod with pivotable and fixed fasteners of FIG. 60 taken along the line 62-62 of FIG. 61 and including another embodiment of the fixed fastener.
Figure 63:
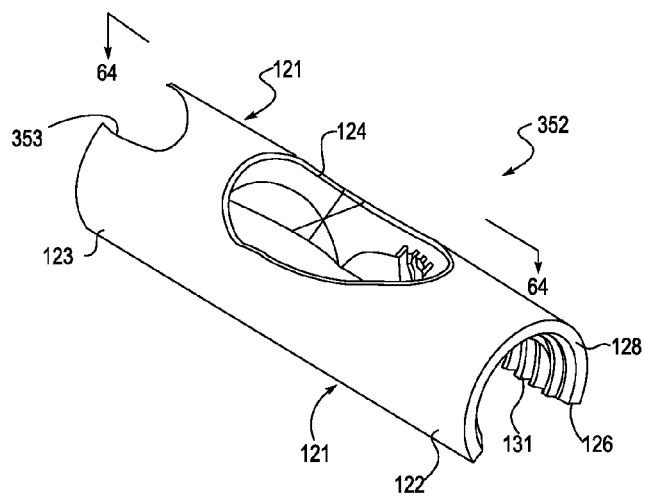
FIG. 63 is a top view, similar to FIG. 15, of the insert of the intramedullary rod with pivotable and fixed fasteners of FIG. 60.

Other embodiments of the intramedullary rod of the present invention, for example with one or more pivotable fasteners and one or more fixed fasteners carried by the proximal portion of the rod, can be provided. Apparatus 331, illustrated in FIGS. 60-64, includes an intramedullary rod 332 substantially similar to rod 62 and like reference numerals have been utilized to describe like components of rods 62 and 332. The intramedullary rod 332 has first and second proximal fasteners 63 and 333 that can be of any suitable type, including a fixation screw, a screw, a peg, a helical blade or any other fixation device. The fasteners 63 and 333 can be solid, as shown in FIG. 62 with respect to second fastener 333, or fenestrated, as shown in FIG. 62 with respect to first fastener 63. The first and second fasteners 63 and 333 may or may not be of the same length and may or may not be of the same type of fastener. For example, the first fastener 63 may be a screw and the second fastener 333 may be a peg or blade. For simplicity, the proximal fasteners are referred to herein and illustrated as first and second proximal fixation screws 63 and 333.

Second screw 333 is formed from an elongate body 336 having a length ranging from 30 to 200 millimeters and a diameter ranging from two to 20 millimeters. The elongate body 336 can be formed from any suitable material such as stainless steel and includes a proximal portion 337 having a drive head 338 and a distal portion 339 that may be provided with external threads 341 extending to a sharpened distal end or tip 342. In the embodiment of the second screw 333 illustrated in FIG. 62, external threads are provided along the entire length of the elongate body 336. It is appreciated that a screw 333 having external threads 341 at other locations, for example at both the proximal portion 337 and the distal portion 339 but not in the central portion, or at solely the proximal portion 337, can be provided.

First proximal fixation screw 63 is pivotably received within first aperture 91 and extends along first axis 92. Second proximal fixation screw 333 is nonpivotably received within a second aperture 346 and extends along a second axis 347. The apertures 91 and 346 are provided in a head 348, substantially similar to head 67, of the rod 332. In one embodiment, an actuation mechanism or assembly 351, substantially similar to actuation mechanism 101, can be provided within the head 348 for pivoting the first proximal fixation screw 63. Actuation mechanism 351, shown assembled in FIG. 62, can include an insert or sleeve 352 substantially similar to the insert 116 of mechanism 101.

Second aperture 346 can optionally be internally threaded, as illustrated in FIG. 62. In embodiments where both the proximal portion 337 of the second proximal fixation screw 333 and the second aperture 346 are threaded, and thus threadedly engage each other, an actuation mechanism 101 need not be provided for pivoting the first proximal or dynamic fixation screw 63 as the second screw 333 can be utilized for the pivoting of the first screw 63.

Figure 64:
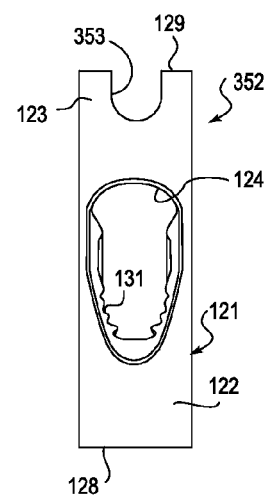
FIG. 64 is an end view of the insert of FIG. 63 taken along the line 64-64 of FIG. 63.
Figure 66:
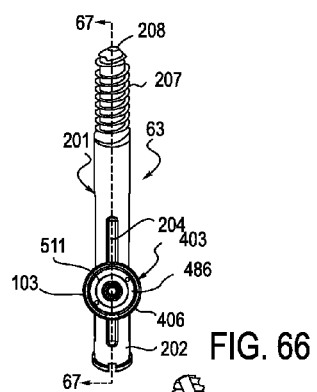
FIG. 66 is a top end view of the intramedullary rod with pivotable fastener of FIG. 65 taken along the line 66-66 of FIG. 65.

Second fixation screw 333 and thus second aperture 341 can be proximal or distal or first aperture 91 and is shown as being distal of the first aperture 91. It is appreciated that a second or fixed fixation screw can be provided both proximally and distally of the one or more pivotable fixation screws of the present invention, between the pivotable fixation screws or any combination of the foregoing. In one embodiment, the second aperture 341 is located distally of the first aperture a distance ranging from two to 30 millimeters side to side and in another embodiment a distance of approximately seven millimeters side to side. Sleeve 352 is provided with a notch or cutout 353 at bottom end 129 for receiving the portion of elongate body 336 extending through head 348 and in the path of the sleeve 352 when the sleeve is moved distally within the head (see FIGS. 63-64). In one embodiment, the first and second proximal fixation screws 63 and 333 extend in the same plane, as can be seen in FIG. 61, although it is appreciated that the fixed screw 333 need not be in the pivot plane of the pivotable screw 63. When the screws 63 and 333 are disposed in the same plane, the center of cutout 353 is circumferentially aligned with the center of transverse opening 124 as shown in FIG. 64.

Figure 60:
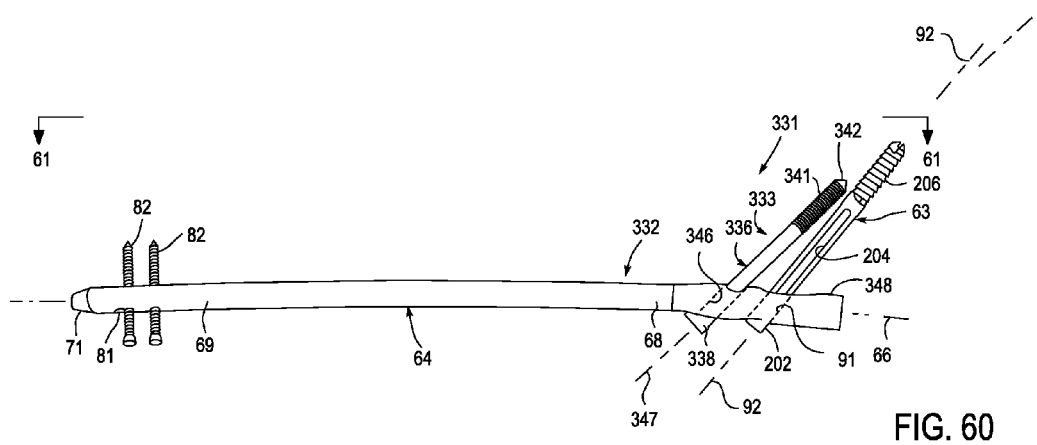
FIG. 60 is a front view an embodiment of an intramedullary rod with pivotable and fixed fasteners of the present invention.

The second proximal fixation screw 333 can be disposed at any suitable angle β relative to longitudinal axis 66 of the elongate body 64. For example, the screw 333 can be inclined proximally, as shown in FIGS. 60-62, be inclined distally (not shown) or be orthogonal to the axis 66. In one embodiment, the screw 333 is inclined relative to axis 66 at an angle β ranging from 90° to 170° and in another embodiment at an angle β ranging from 120° to 140° (see FIG. 62). In one embodiment, the distal portion 339 of the second fixation screw 333 is inclined relative to the pivotable fixation screw 63 so as to contact or abut the first fixation screw 63, and preferably contact or abut the first fixation screw 63 between the proximal portion 202 and distal portion 206 of the screw 63 (see FIG. 62).

Apparatus 31 can be used in any suitable procedure for repairing a bone of a mammalian body, for example a femur in a leg. In one procedure utilizing apparatus 31, for example in one of the procedures illustrated in FIGS. 57-59 and discussed above, rod 332 is introduced through the greater trochanter 321 into the medullary canal 332 in the shaft 323 of the femur 311. Suitable holes 324 are made in the side of the greater trochanter to allow insertion of the first and second fixation screws 63 and 333 into respective first and second apertures 91 and 346 of the rod 332. First screw 63 can be initially introduced through rod 332 and screwed into the head 326 of the femur 311. If necessary, the first screw 63 is pivoted relative to longitudinal axis 66 of rod 332 in the manner discussed above. Thereafter, the second screw 333 is introduced through rod 332 and screwed into the femur head 326. The nonpivotable or fixed second screw can extend parallel or at an inclination to the first screw 63 and in either case serves to enhance the mechanical strength of apparatus by sharing the torque and other forces being experienced by the first screw 63 and the actuation assembly 351 supporting the first screw 63.

The nonpivotable or fixed screw 333 can be sized and introduced a sufficient distance so as to engage the side of the first screw, for example at a distance proximal of the distal tip 208 of the first screw 63. When the second or fixed screw 333 is so disposed relative to the first screw 63, the fixed screw serves to buttress or statically support the inferior or bottom of the first screw and thus minimize undesirable pivoting of the first screw relative to the rod 332 after final placement of the apparatus 331 within the femur 311. The buttressing and support of the first or dynamic screw 63 by the second or static screw 333 can be enhanced when the proximal portion 337 of the screw 333 and the second aperture 346 threadedly engage each other so that the second screw is nonslidably engaged with the head 348.

In a further aspect of the invention, and after the fixed screw 333 is abutting the side of the first screw 63, the fixed screw 333 can be further advanced relative to the head 348 of the rod 332 so as to cause the first screw 63 to pivot relative to the head 348, for example to pivot the first screw 63 toward proximal opening 77 of the rod 332. Such pivoting of the first screw 63 may be desirable when fine adjustments to the first screw 63 are desired, and can be accomplished when the proximal portion 337 of the screw 333 and the second aperture 346 are not threaded, in which case screw 333 is advanced by its threaded engagement with the head 326 of the femur 311, or when the proximal portion 337 and the second aperture 346 are both threaded, in which case the screw 333 is advanced solely or additionally by its threaded engagement with the head 348 or the rod 332. The length of the static screw 333 can be selected to choose the amount by which the dynamic screw 63 is pivoted relative to head 348. In this regard, in the illustrated embodiment the greater the length of the static screw 333 the greater the amount by which the dynamic screw 63 is pivoted relative to head 348.

It is appreciated that an actuation mechanism 351 need not be provided when the fixed screw 333 is used solely as the means for pivoting the dynamic screw 63. In one such embodiment, the dynamic screw pivots freely relative to head 348 and is supported in its desired position by static screw 333, either solely or in combination with another suitable securement mechanism (not shown). It is also appreciated that other means can be provided for pivoting the dynamic screw 63 and be within the scope of the present invention.

In another aspect of the invention, a locking mechanism is provided for use with an implantable medical device. The locking mechanism can be utilized with any medical device having a rotatable, control, moveable or other element on the outside or inside thereof. In one embodiment, the locking mechanism can be used with a threaded element, for example an internal or external threaded element of a medical device. In one embodiment the element can be an element for controlling another moveable element of a medical device, for example a control element coupled to a longitudinally moveable or slidable element of the medical device. In one embodiment described and illustrated herein, the medical device is an implantable intramedullary rod.

One embodiment of an implantable medical device having a locking mechanism of the type discussed above is apparatus 401 illustrated in FIGS. 65-81. Apparatus 41 is similar to apparatus 61 and includes an intramedullary rod or nail 402 substantially similar to nail 62. Like reference numbers have been used to describe liked components of nails 402 and 62. Although the rod 402 can be used in any bone of a mammalian body, in one embodiment rod 402 is for use in a femur and may thus be called a femoral nail 402. Nail 402 includes an elongate body 403, which can be similar to elongate body 64 of nail 62 that extends along a longitudinal or central axis 404 and can have a proximal portion or head 406, a central portion or neck 407 and a distal portion or shaft 408 that terminates at a distal tip 71. The nail 402 is illustrated schematically in the figures, where head 406, neck 407 and shaft 408 are not necessary drawn to scale. Like elongate body 64, body 403 may curve in at least one portion of shaft or stem 408 to align the rod 402 along the length of the marrow canal of the femur or other bone in which the rod is to be inserted. Elongate body 403, including tubular head or head 406, neck 407 and shaft 408, can have a size, shape and construction similar to body 64, for example as such parts of body 64 are discussed above. In this regard, for example, elongate body 403 can be provided with a longitudinally-extending passageway or bore 76 of the type discussed above for permitting the rod to slide along a guide wire (not shown) during insertion of the rod into the femur or other bone of the mammalian body. Furthermore at least one bore 81 can be provided in the distal end portion of stem 408 adjacent tapered tip 71 for receiving at least one distal fastener of the type discussed above and including screw 82.

Figure 68:
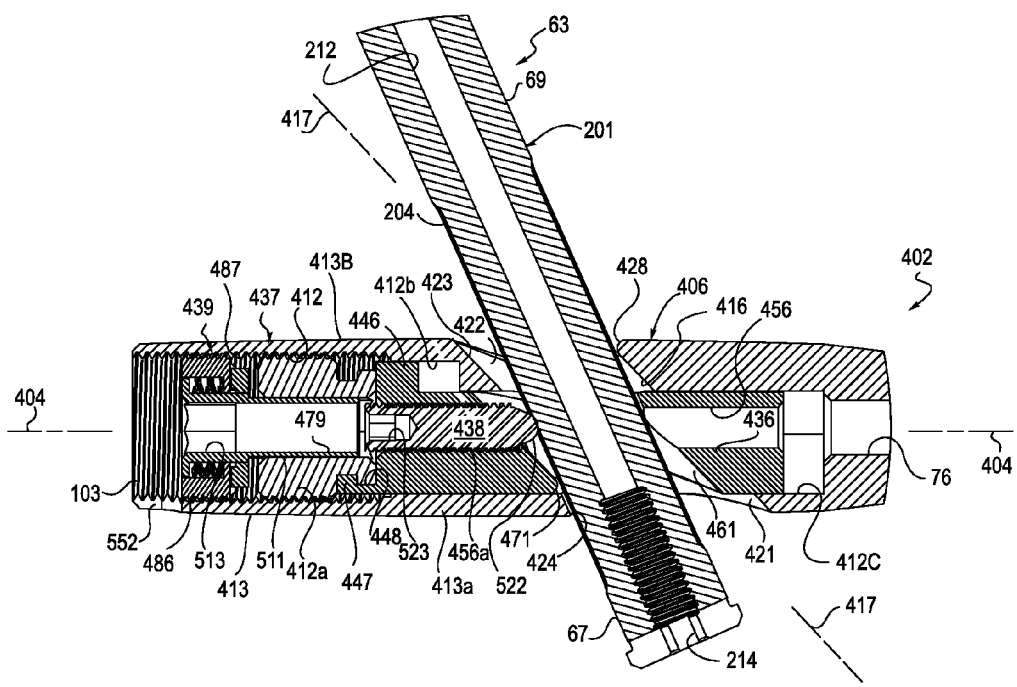
FIG. 68 is an enlarged cross sectional view of the intramedullary rod with pivotable fastener of FIG. 65 taken along the line 68-68 of FIG. 67.
Figure 69:
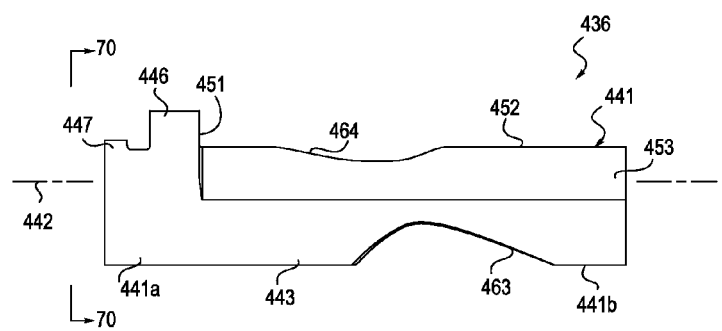
FIG. 69 is a side view of the insert of the intramedullary rod with pivotable fastener of FIG. 65.
Figure 70:
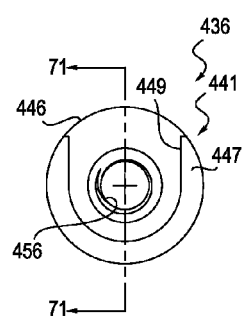
FIG. 70 is a top end view of the insert of FIG. 69 taken along the line 70-70 of FIG. 69.
Figure 71:
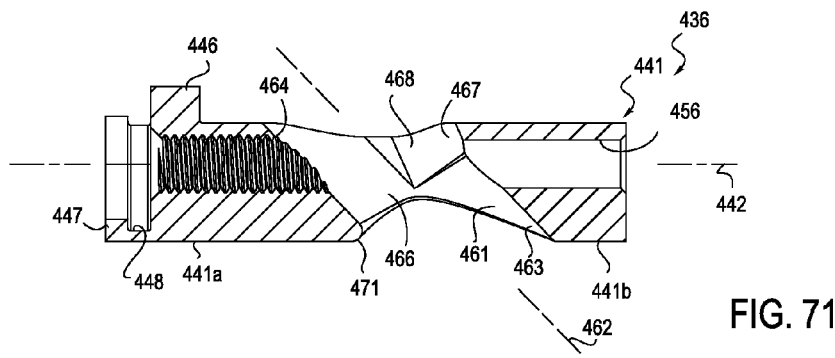
FIG. 71 is a cross-sectional view of the insert of FIG. 69 taken along the line 71-71 of FIG. 70.
Figure 72:
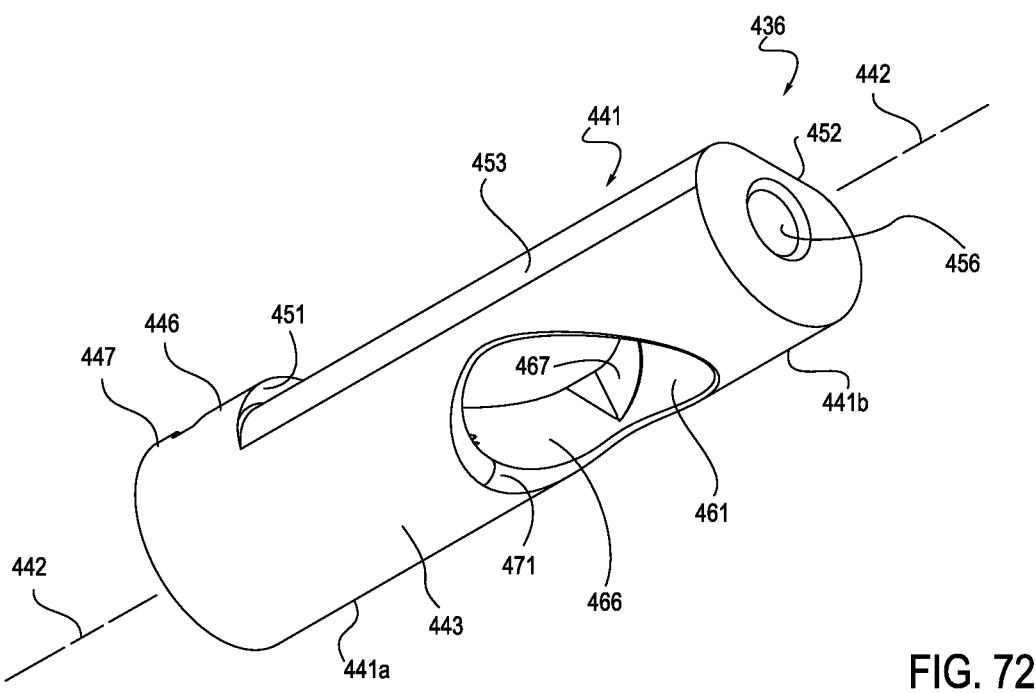
FIG. 72 is a perspective view of the insert of FIG. 69.
Figure 73:
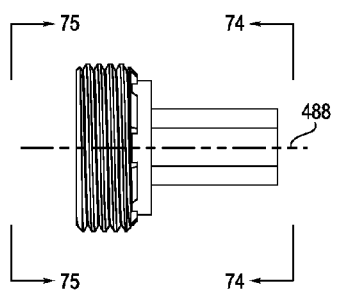
FIG. 73 is a side view of the locking mechanism of the intramedullary rod with pivotable fastener of FIG. 65.
Figure 74:
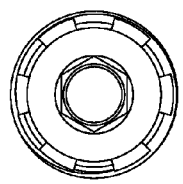
FIG. 74 is a bottom end view of the locking mechanism of FIG. 73 taken along the line 74-74 of FIG. 73.
Figure 75:
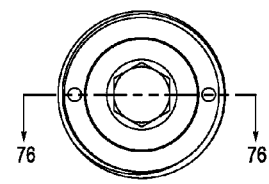
FIG. 75 is a top end view of the locking mechanism of FIG. 73 taken along the line 75-75 of FIG. 73.
Figure 76:
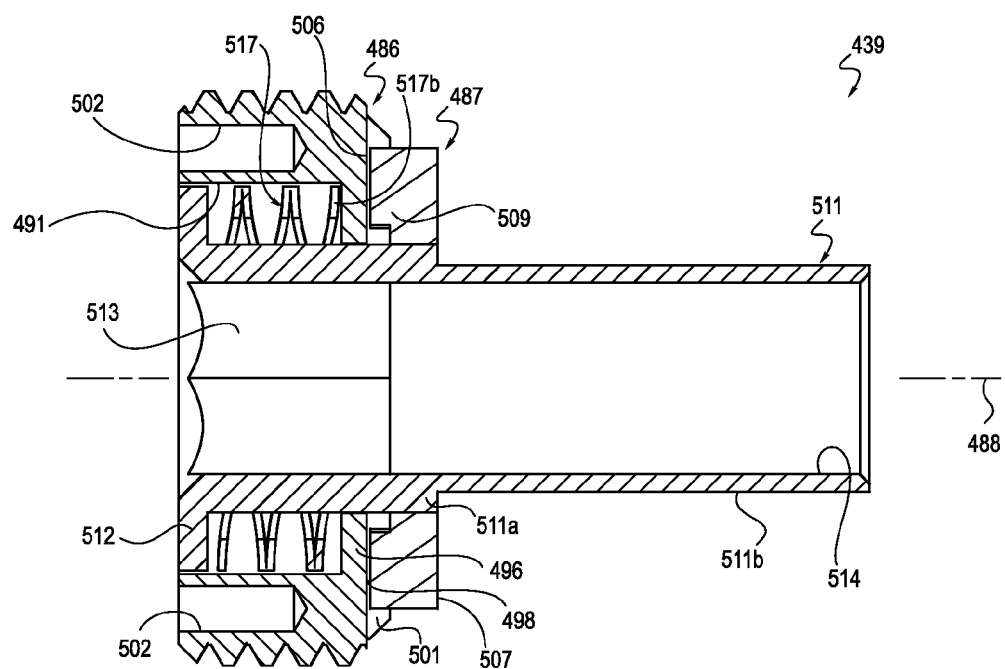
FIG. 76 is a cross-sectional view of the locking mechanism of FIG. 73 taken along the line 76-76 of FIG. 75.
Figure 77:
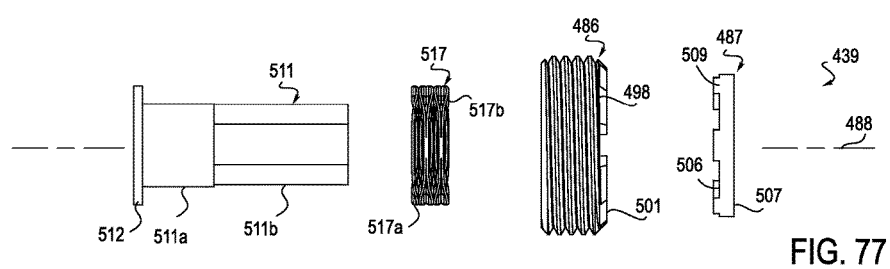
FIG. 77 is a side exploded view of the locking mechanism of FIG. 73.
Figure 78:
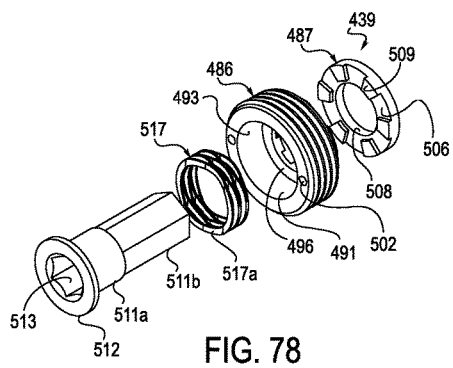
FIG. 78 is a first perspective view of the exploded locking mechanism of FIG. 73.
Figure 79:
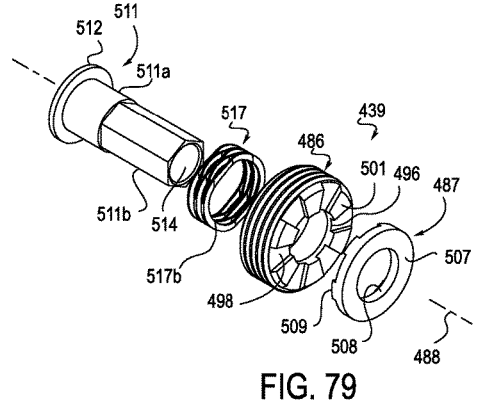
FIG. 79 is a second perspective view of the exploded locking mechanism of FIG. 73.

Head 406 of rod 402 is configured to permit pivoting of proximal fixation screw 63 relative to the head 406 and may include an actuation or adjustment mechanism or assembly 411, which can be similar to adjustment mechanism or assembly 101 described above, for selectively pivoting proximal fixation screw 63 from a first angled position relative to the nail head 406 to a second angled position relative to the nail head. In one embodiment, the actuation assembly 411 extends longitudinally of the head 406. As illustrated in FIGS. 78 and 68, the proximal portion central passageway 76 of the nail 402 can be hallowed to form a longitudinally-extending proximal recess 412, which can be substantially similar to recess 102 discussed above, that communications with proximal opening 103 in the proximal end of the head 406. As illustrated in FIG. 68, proximal recess 412 can have a proximal or threaded portion 412a adjacent proximal opening 103, a circular central portion 412b and a distal portion 412c that in one embodiment, discussed and illustrated herein, is noncircular in cross section and sometimes referred to herein as the segmented circular portion or segmented portion 412c. Tubular head 406 is formed by an outer wall 413, which is substantially annular in shape and formed by the proximal recess 412, having a first side portion 413a and an opposite second side portion 413b relative to central longitudinal axis 404.

Figure 65:
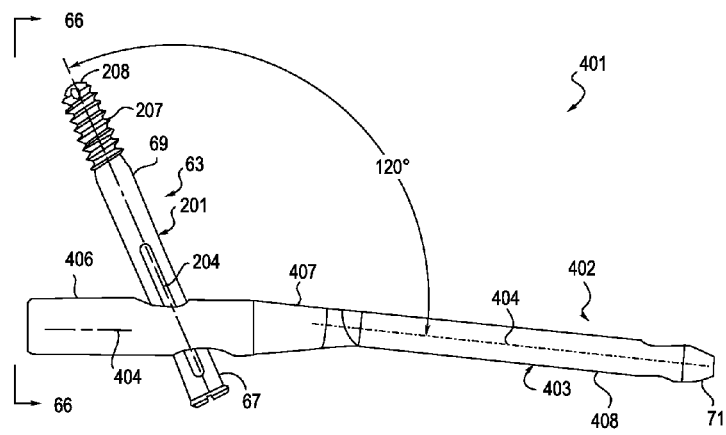
FIG. 65 is a rear view of a further embodiment of an intramedullary rod with pivotable fastener of the present invention.
Figure 67:
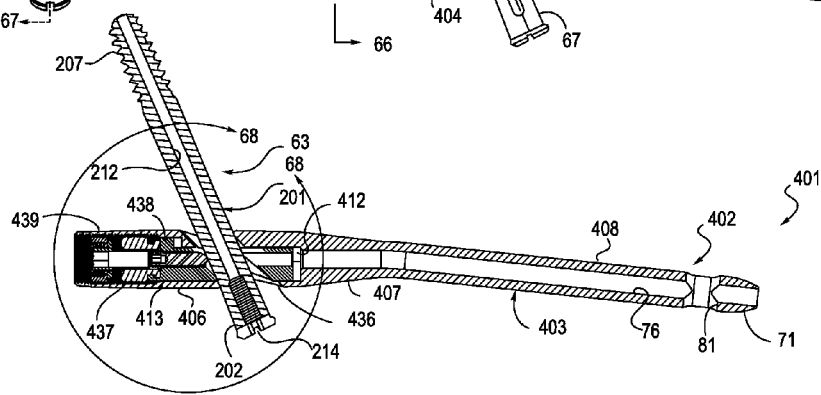
FIG. 67 is a cross-sectional view of the intramedullary rod with pivotable fastener of FIG. 65 taken along the line 67-67 of FIG. 66.

Head 406 is provided with at least one aperture 416 extending along a transverse axis 417 inclined at an angle to longitudinal axis 404. Head 406 is adapted to receive fastener or screw 63 in aperture 416, which is distinct from proximal recess 412 of elongate passageway 76, but formed in part by the proximal recess 412. In one embodiment, head 406 is provided with a single aperture 416. More specially, the aperture 416 is formed by first and second spaced apart openings extending respectfully through the outer, opposite side portions of wall 413 of the head 406. In this regard, a first or lateral transverse opening 421 is provided on one side of wall 413 or first side portion 413a of the wall and a second or medial transverse opening 422 is provided on the other side of the wall 413 or second side portion 413b of the wall. At least one of the openings 421 and 422 can be elongate or oblong in a direction parallel to longitudinally axis 404 so as to facilitate pivoting of the fixation screw 63 relative to head 406 about a pivot axis (not shown) extending orthogonally to longitudinally axis 404 and aperture axis 417. In one embodiment, as illustrated in FIGS. 65, 67 and 68, the lateral transverse opening 421 is so elongate or oblong. Axis 417 is centered on aperture 416 and can extend relative to longitudinal axis 404 at an angle and in one embodiment at an angle of approximately 140 degrees measured from the portion of head 406 distal of head aperture 416.

Aperture 416 is formed by an inner circular surface 423 centered on axis 417. A cutout 424 formed by a cutout semicircular surface 426 is provided in the portion of outer wall 413 that opens onto and forms the proximal portion of lateral transverse opening 421. Cutout surface 426 is centered on an axis (not shown) within the angular range of axis 417 relative to longitudinal axis 404 disclosed above and in one embodiment on an axis extending at an angle of approximately 120 degrees measured from the portion of head 406 distal of aperture 416. In one embodiment, the diameter of inner circular surface 423 and cutout surface 426 are each approximately equal to the diameter of fixation screw 63 such that when the fixation screw is extending at an angle of approximately 140 degrees relative to the head 406 and axis 404 the cylindrical body 201 of the screw 63 is seated flush with the inner circular surface 423 (see FIG. 81), and when the fixation screw is extending in an angle of approximately 120 degrees relative to the head 406 and axis 404 the cylindrical body 201 of the screw 63 is seated flush with the cutout semicircular surface 426 (see FIG. 68). The distal portion of medial transverse opening 422 in wall second side portion 413b is provided with a convex variable radius or rounded contact surface 428 at the radial outside of outer wall 413. In one embodiment of the invention, contact surface 428, which is on second side portion 413b of head 406, defines the pivot axis of screw 63.

Although the actuation or adjustment mechanism 411 for pivoting the proximal fixation screw 63 can be of any suitable type, in one embodiment mechanism 411 includes an insert, element or sleeve 436, a threaded element or control element 437, an alignment or set screw 438 and a locking mechanism 439, illustrated as assembled in FIG. 68 and separately in FIGS. 69-79. Unless otherwise indicated, each of these components can be made any suitable material such as stainless steel.

Sleeve 436, which in one embodiment is one example of the broad categories of elongate elements or movable elements, can be formed from elongate tubular element or member 441 having a proximal portion or end portion 441a and a distal portion or end portion 441b and extending along a longitudinal or central axis 442. Elongate member 441 is formed with a bottom surface 443 which is semicircular in cross section and extends the entire length of the elongate member. Proximal portion 441a includes a circular annulus or ring 446 and a lip 447 spaced proximally from annulus 446 by an annular or recess 448 Annulus forms the periphery of the proximal portion 441a,and of the elongate member 441, and is substantially circular in shape. Lip 447 extends around the periphery of the proximal portion 441a,but is provided with an opening or cutout 449 at the top thereof such that the lip 447 does not extend around the top of elongate member 441. Elongate member 441 is provided with an elongate cutout 451 extending distally of annulus 446, and the cutout 451 is formed by a flat 452 which is planar and parallel to central axis 442. A concave arcuate surface 453 extends from each side of the flat 452 to bottom surface 443. As such, distal portion 441b of the sleeve 436 is noncircular in cross section and in one embodiment its segmented circular cross section, as described above, corresponds generally with the cross section of segmented portion 412c of the head proximal recess 412. Distal portion 441b of the elongate member 441 is sized and shaped to slidably move longitudinally within segmented circular portion 412c of the proximal recess 412 of the head 406 Annulus 446 of the sleeve of 436 is externally sized and shaped to slidably move longitudinally move within central portion 412b of the head proximal recess 412. A passageway or bore 456 extends the length of elongate member 441 from a proximal opening in annulus 446 to a distal opening at the distal end of the member 441. In one embodiment, bore 456 is internally threaded at its proximal portion 456a and has an internal diameter less than the inner diameter of lip 447.

Sleeve 436 is provided with at least one aperture 461 extending along an axis 462 inclined at an angle to central axis 442 and adapted to receive fastener or fixation screw 63. Aperture 461 is distinct from bore 456, and the bore 456 extends through the aperture 461. In one embodiment, sleeve 436 is provided with a single aperture 461, which opens onto bottom surface 443 at a first or lateral transverse opening 463 and opens onto flat 452 and arcuate surface 453 at a second or medial transverse opening 464. At least one of the openings 463 and 464 can be elongate or oblong in a direction parallel to central axis 442 so as to facilitate pivoting of the fixation screw 63 relative to head 406 and sleeve 436 about an axis (not shown) extending orthogonally to sleeve central axis 442 and aperture axis 462. In one embodiment, medial transverse opening 464 is so provided with a cutout at its distal portion so as to be elongate or oblong. Axis 462 can be centered on aperture 461 and can extend relative to central axis 442 at an angle and in one embodiment at the same angle that axis 417 extends relative to longitudinal axis 404. The aperture 461 can be formed by an inner circular surface 406, shown most clearly in FIG. 71, which is centered on aperture axis 462. Aperture 461 can further include a cutout 467 along its distal end adjacent medial transverse opening 464 that is formed by a semicircular cutout surface 468 which can be centered on an axis (not shown) within the angular range of aperture axis 462 relative to central axis 442 and in one embodiment on an axis extending at an angle of approximately 120 degrees measured from the portion of sleeve 436 distal of sleeve aperture 461. The proximal portion of lateral transverse opening 463 is provided with a convex variable radius or rounded contact surface 471, which is on the first side portion 413a of the head 406. The internally-threaded proximal portion 456a of sleeve bore 456 can extend distally to transverse aperture 461. In one embodiment, the sleeve 436 extends longitudinally of the head.

Rotatable control element 437, which in one embodiment is one example of the broad categories of elements which include control elements, movable elements and threaded elements, is carried by head 406 and accessible at proximal opening 103 for causing the adjustment mechanism 411 to pivot fixation screw 63 relative to the head 406. The control element can be of any suitable type and in one embodiment includes a spindle, screw or worm gear 437 formed from a cylindrical body 476 (see FIGS. 68, 80 and 81) extending along a central or longitudinal axis (not shown). Cylindrical body 476 includes a first or proximal portion 476a that can have an externally threaded outer surface diametrically sized for threaded engagement with threaded portion 412a of proximal recess 412 of the head 406. Second or distal portion 476b of the cylindrical body 476 can include an annular flange 477 spaced from externally-threaded proximal portion 476a by an annular recess 478. The annular flange 477 is diametrically sized and shaped to snugly seat within recess 448 of the sleeve 436. Similarly, annular recess 478 of the cylindrical body 476 is diametrically sized and shaped to snugly receive lip 447 of the sleeve 436. Annular flange 477 can be so coupled to sleeve 436 by sliding the flange 477 transversely relative to sleeve 436 though cutout 449 into the recess 448. When worm gear 437 is coupled or connected to sleeve 436 in this manner, the central axis of the worm gear is coincident with central axis 442 of the sleeve 436 and the worm gear is longitudinally fixed or locked relative to the sleeve 436 Annular flange 477 and annular recess 478 are configured and sized, however, to permit worm gear 437 to rotate relative to sleeve 436 when such elements are so coupled together.

Worm gear 437 controls the longitudinal position and movement of sleeve 436 when such elements are disposed within head 406. In this regard, cylindrical body 476 can be tubular in conformation and be provided with a central passageway or drive socket 479 extending longitudinally through the body 476. Socket 476 has a noncircular cross section of any suitable type or shape and in one embodiment the cross section is hexagonal in shape. When sleeve 436 and worm gear 437 are so disposed within nail head 406, a suitable drive element seated within drive socket 479 of the worm gear 437 can serve to screw or rotate the worm gear 437 proximally or distally within the internally-threaded portion 412a of head proximal recess 412. Such advancement or withdrawal of the worm gear 437 within head 406 simultaneously causes sleeve 436 to advance or withdraw, in a one-to-one manner with the longitudinal movement of the worm gear 437, in central portion 412b and segmented portion 412c of the head proximal recess 412. In one embodiment, for example, worm gear 437 can be rotated in a clockwise direction from proximal opening 103 so as to cause sleeve 436 to move distally within the head 406, and rotated in a counter-clockwise direction from proximal opening 103 so as to cause the sleeve 436 to move proximally within the head 406. In one embodiment, the diameter of drive socket 479 is larger than the diameter of the internally-threaded proximal portion of longitudinal bore 456 of the sleeve 439 and is preferably coaxially aligned with sleeve bore 456.

Locking mechanism, assembly or device 439 is coupled to worm gear 437 and configured to preclude rotation of the worm gear relative to head 406 when the locking mechanism is in a first position and permit rotation of the worm gear 437 relative to the head 406 when the locking mechanism is in a second position. Although it is appreciated that locking mechanism 439 can have any suitable configuration and construction for rotatably locking and unlocking worm gear 437 within head 406, in one embodiment the locking mechanism includes a first locking element 486 and a second locking element 487 centered on a central or longitudinal axis 488 of the locking mechanism 439. The second locking element 487 is moveable longitudinally between a first position in which the second locking element 487 engages the first locking element 486 so as to be rotatably locked with the first locking element and a second position in which the second locking element 487 is disengaged from the first locking element 486 so as to be rotatable relative to the first locking element.

In one embodiment, the first locking element is annular in shape and can be an annular element. In one embodiment the first element 486 can be in the form of a nut that can be externally treaded and diametrically sized so as to threadably engage threaded portion 412a of proximal recess 412 in head 406. Annular nut 486 can include a circular inner surface 491 centered on central axis 488 for forming a bore 493 extending along the axis 488 through a portion of the nut 486. A flange 496 extends radially inwardly from the distal end of inner circular surface 491 and terminates at annular or circular surface which is coaxial with inner circular surface 491. Nut 486 has a distal surface 498 which includes flange 496 and in one embodiment the surface 498 is planar and orthogonal to central axis 488. A plurality of locking or engagement means or elements are provided on distal surface 498 and can be of any suitable type, including a plurality of recesses, protuberances or a combination of recesses and protuberances. In one embodiment, such locking means includes a plurality of first upstanding protuberances or dogs 501 extending longitudinally outwardly from the distal surface 498. In one embodiment, a plurality of first dogs 501 are spaced circumferentially around surface 498 and in one embodiment the first dogs 501 are circumferentially spaced equally apart around the distal surface 498. A suitable means is included within nut 486 for rotating the nut within threaded portion 412a of head proximal recess 412 and can include spaced-apart first and second bores 502 extending longitudinally inwardly from the proximal end of the nut. In one embodiment, bores 502 are diametrically opposed on opposite sides of bore 493 and are sized to receive a suitable drive tool for so rotating the nut 486 with nail head 406.

In one embodiment, the second drive element 487 is annular in shape and can be an annular element. In one embodiment, the second drive element can be in the form of a washer having opposite first and second planar surfaces 506, 507 extending parallel to each other and a bore 508 extending between the surfaces 506 and 507. The washer 487 has an outer diameter smaller than the inner diameter of threaded portion 412a of the head proximal recess 412. Similar to distal surface 498 of nut 486, first surface 506 of the washer is provided with a plurality of locking or engagement means or elements of any suitable type, including a plurality of recesses, protuberances or a combination of recesses and protuberances. In one embodiment, such locking means include a plurality of second upstanding protuberances or dogs 509 extending longitudinally outwardly from the first surface 506. In one embodiment, the plurality of second protuberances 509 are spaced circumferentially around the first surface 506 and in one embodiment the second dogs circumferentially spaced apart so as to register with or engage first dogs 501 and thus preclude relative to rotation between washer 47 and nut 46 when the washer 487 and second dogs 509 are in the first position. In this manner, second dogs 509 cooperatively engage first dogs 501 when washer 487 is in the first position.

Locking mechanism 439 can further include a driver element or driver 511 having a proximal portion 511a with a circular outer surface and a distal portion or drive head 511b with an outer surface that is non-circular in cross section. The diameter or at least the distal portion of the circular outer surface approximates the diameter of the inner circular surface of nut flange 496. The cross-sectional shape of distal end or drive head 511b can be, for example, triangular, square, hexagonal or octagonal, and preferably corresponds in size and configuration and cooperates with drive socket 479 of the worm gear 437. A flange 512 extends radially outwardly from proximal portion 511a at the proximal end of driver 511. Flange 512 has an outer circular surface with a diameter that approximates the diameter of the inner circular surface 491 of nut 486. A drive socket 513 extends longitudinally inwardly from the proximal end of driver 511 and preferably has a cross section which is non-circular in shape, for example similar to the cross-sectional shape of drive head 511b discussed above, so that when the socket 513 is engaged by a suitable tool it can serve to cause rotation of the driver 511. A longitudinally-extending bore 514 extends distally from drive socket 513 through the remainder of the driver 511.

For assembly, driver 511 extends through nut 486 and washer 487. More specially, the driver 511 extends through bore 493 and flange 496 of the nut 486 until the nut flange 496 is in close proximity to driver proximal portion 511a and driver flange 512 is seated within bore 493 and in one embodiment flush with the proximal end of nut 486. In one embodiment, flange 496 of the nut engages the outer circular periphery of proximal portion 511a of the driver 511. Washer 487 extends around distal portion or end of driver proximal portion 511a distal of nut 46 so that when locking mechanism 439 is in its first or rest position second dogs 509 of washer 487 are cooperatively engaged and locked with first dogs 501 of nut 486. The washer 487 is secured to proximal portion 511a of the driver by any suitable means such as welding. Nut 486 is not secured to driver 511 and thus longitudinally moveable relative to the driver.

Means is included with locking mechanism 439 for urging washer 487 towards its first or locking position relative to nut 486 in which first and second dogs 501, 509 are cooperatively engaged and thus rotatably locked relative to each other. In this regard, an annular recess 516 is provided between nut 46 and driver 511. Recess 516 is formed at its outer periphery by inner circular surface 491 of nut 486, at its inner periphery by the outer circular surface of driver proximal portion 511a, at its proximal extremity by flange 512 of driver 511 and its distal extremity by flange 496 of nut 486. A suitable spring, for example an annular wave spring 517, is disposed in recessed 516 and extends around driver 511. The spring 571 has a proximal end portion 517a engaging flange 512 of driver 511 and a distal end portion 517b engaging flange 496 of the nut 486.

Locking mechanism 439 is movable between a first position in which driver 511 can rotate freely relative to nut 486 and a second position in which the driver 511 is rotatably locked with the nut 486. Spring 517 urges locking mechanism 439 towards its first or rest position, illustrated in FIGS. 76 and 82, in which the springs 517 urges flange 512 of the driver 511 longitudinally away from flange 496 of nut 486 so that second dogs 509 on first surface 506 of washer 487 register and rotatably lock with first dogs 501 on distal surface 498 of the nut 46. When driver 511 is urged longitudinally in a distal direction, for example by insertion of a suitable drive tool in drive socket 513 of the driver 511 and exertion of a longitudinal force in the distal direction on the tool and thus the driver 511, washer 487 that is rigidly secured proximal portion driver 511a of the driver is moved longitudinally against the force of spring 517 away from distal surface 498 of nut 486 so that the second dogs 509 of the washer 487 separate and disengage from first dogs 501 of the nut 46 to a second or disengaged position, illustrated in FIG. 83, in which the combined driver 511 and washer 487 unit can be rotated relative to nut 486. As such, washer 487 is spaced longitudinally from nut 486 when the washer is in its second position.

Set screw 438 can be of any suitable type and similar to set screw 119 discussed above. In one embodiment, set screw 438 is cylindrical in conformation and externally threaded. The set screw 438 can include a rounded distal end 522 and a suitable drive socket 523 provided at its proximal end. Such set screw is diametrically sized so as to be capable of being passed longitudinally through drive socket 513 and bore 514 of drive 511 and into bore 456 of the sleeve 436 to threadably engage the threaded proximal portion 45ba of the sleeve bore 456.

The internal components of head 406 can be loaded in proximal recess 412 of the head in any suitable manner. In one such method of assembly, sleeve 436 is introduced through threaded portion of 412a so that distal portion 441b of the sleeve is seated within segmented portion 412c of the recess 412 and annulus 446 of the sleeve is seated within central portion 412b of the recess 412. As discussed above, distal portion 441b has an external cross section similar to the internal cross section of segmented portion 412c so that sleeve 436 is rotatably locked but longitudinally movable or slidable in nail 402 relative to axis 404 of the nail. Aperture 461 of sleeve 436 is generally registered with aperture 416 of head 406 in the operational longitudinally positions of sleeve 436 within the nail head 406.

Worm gear 437 is coupled to proximal portion of sleeve 436, in the manner discussed above, prior to the full insertion of the sleeve elongate member 441 within head recess 412. The externally-threaded proximal portion 476a of the worm gear 437 threadably engages threaded portion 412a of the nail head 406 during longitudinal insertion of sleeve 436 and worm gear 437 through proximal opening 403 of the head 406. Drive head 511b of locking mechanism 439 can be inserted into drive socket of 479 of worm gear 437, so as to couple the locking mechanism 439 to the worm gear 437, before the worm gear 437 is entirely threaded into head recess 412 and properly positioned longitudinally relative to the worm gear 437 before being threaded into threaded portion 412a of the proximal recess 412. When locking mechanism 439 is in its first position, a suitable drive tool can be inserted into drive socket 523 so as to rotate both the locking mechanism 439 and worm gear 437 during the introduction of the components of adjustment mechanism 411 into the head.

Once sleeve 436, worm gear 437 and locking mechanism 439 have been properly positioned longitudinally within proximal recess 412, and longitudinally positioned relative to each other, nut 486 of the locking mechanism is secured to the head 406 and in one embodiment locked or secured against both rotatable and longitudinally movement within the head 406. In one embodiment, the engaged invisible internal threads of threaded portion 412a of the head 406 and external threads at the proximal end of nut 486 are punched at one or more positions, for example at a plurality of circumferentially-spaced apart positions, by a suitable punching tool so as to preclude nut 46 from being rotatably moved in a proximal direction, and thus withdrawn, from threaded portion 412a of recess 412.

Nail 402 can be placed within a bone in any suitable manner and for example as discussed above and as discussed below. In one method of inserting the nail 402 into a bone of a mammalian body, a guide wire is first introduced into the bone and the nail is then threaded over the proximal end of the guide wire for proper placement and positioning in the bone. In this regard, the proximal end of the guide wire can be inserted through passageway 76 of the elongate body 403, though adjustment mechanism 411 by means of bore 456 of sleeve 436 and drive socket 479 of worm gear 437, and through locking mechanism 439 by means of bore 514 and drive socket 513 of driver 511. After the nail 402 has been properly positioned within the bone, the guide wire is removed from the nail 402 through proximal opening 103.

A suitable fastener such fixation screw 63 can be introduced through head 406 by means of lateral transverse opening 421, aperture 461 of sleeve 436 and medial transverse opening 422 and properly positioned within the bone. In this regard, lateral transverse opening 421 in first side portion 413a of wall 413 receives the proximal portion or head 67 of the fastener and medial transverse opening 422 in second side portion 413b of wall 413 receives the distal portion or shaft 69 of the fastener 63. Similar to the manner discussed above, fixation screw 63 can be pivoted relative to head 406 and central axis 404 through a range of angles by means of adjustment mechanism 411. In this regard, control element or worm gear 437 can be accessed through proximal opening 103 at the proximal end of head 406, for example by insertion of a suitable drive tool (not shown) through opening 103 and into proximal recess 412 and then into drive socket 513 of driver 511. In order to rotatably unlock locking mechanism 439 and worm gear 437 that rotates one-to-one with driver 511 of the locking mechanism, so as to permit longitudinal movement of sleeve 437 within head 406, the drive tool is urged distally in drive socket 513 relative to head 406 so as to cause the driver 511 to move longitudinally along axis 404 and thus cause washer second dogs 509 to longitudinally separate and disengage from nut first dogs 501 in the manner discussed above. Once the combined driver 511 and washer 487 unit have been moved to a second position of locking mechanism 439, the drive tool can be used to rotate driver 511 freely of nut 486 and head 406 so as to rotate worm gear 437 and thus cause the worm gear and sleeve 436 coupled to the worm gear to move longitudinally within recess 412. In this regard, since the portion of the fixation screw 63 extending through aperture 461 of the elongate member 441 is constrained by sleeve 436, longitudinal movement of the sleeve relative to head 406 causes the fixation screw to pivot about medial transverse opening 422 of the head 406.

Figure 80:
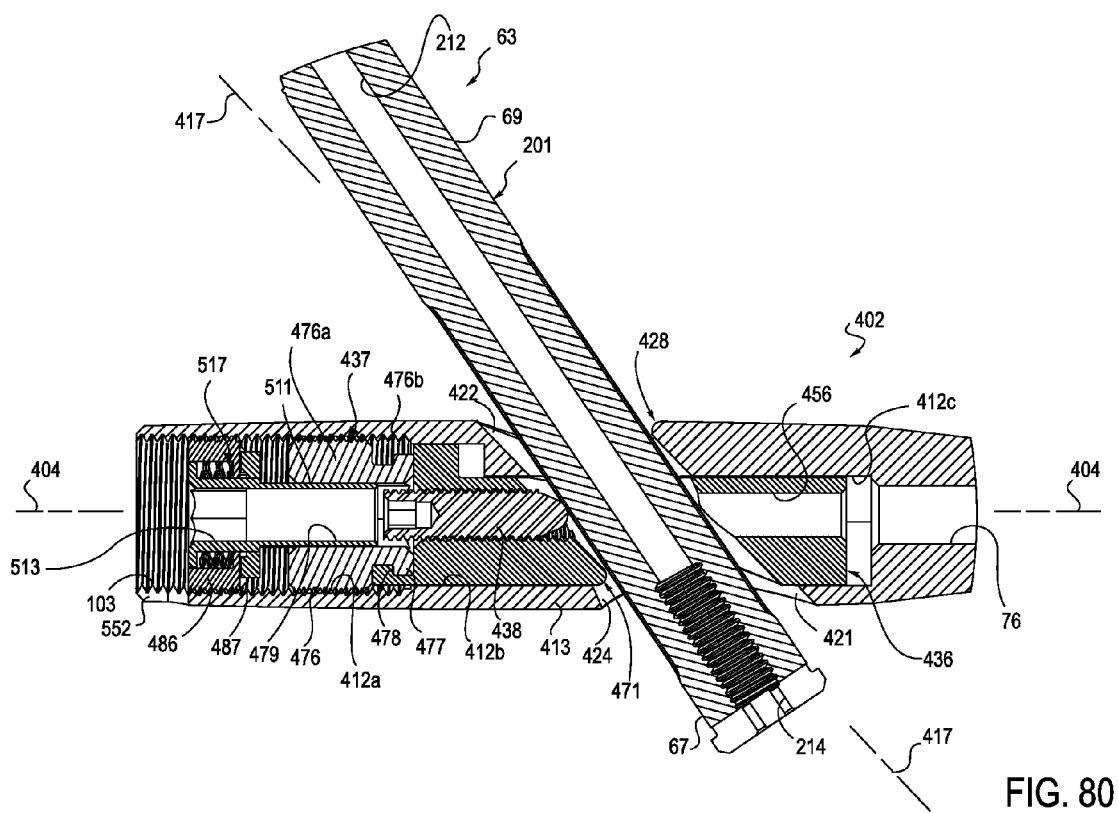
FIG. 80 is an enlarged cross sectional view, similar to FIG. 68, of the intramedullary rod of FIG. 65 with the pivotable fastener in a second position.
Figure 81:
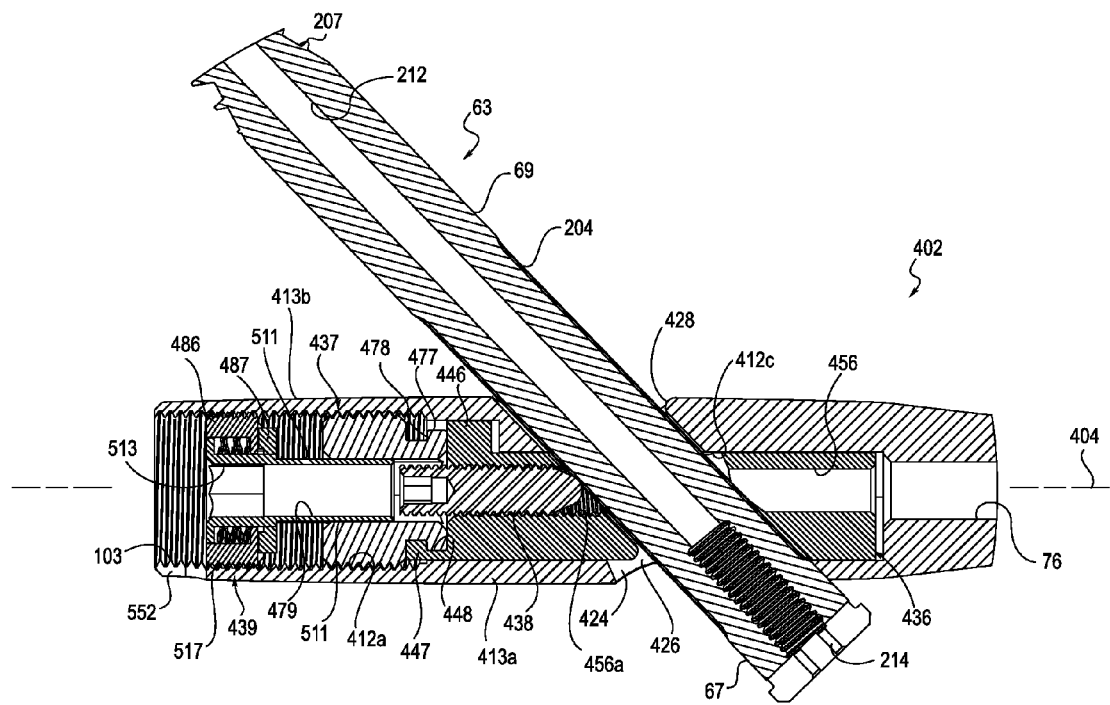
FIG. 81 is an enlarged cross sectional view, similar to FIG. 68, of the intramedullary rod of FIG. 65 with the pivotable fastener in a third position.

The construction of head 406 and sleeve 436 provides a particularly robust structure for pivoting the fixation screw 63 in a counter-clockwise direction in FIGS. 68, 80 and 81, which for example correlates to reducing a fracture and moving the head 326 of a femur 311 out of varus as shown in FIGS. 57-59 and described above. Such structure also enhances retention of the fixation screw 63 in the desired angular position relative to nail head 406, for example after completion of the insertion and positioning of the nail 402 within a bone of a mammalian body and the head 326 of the bone is placed under load when the mammalian body is standing or walking so as to be urging head 326 of the bone into varus and thus exerting a moment on screw 63 in a clockwise direction in FIGS. 67, 68, 80 and 81. In this regard, rounded contact or support surface 428 of nail head 406 engages one side of the shaft 69 of screw 63, on the first side portion 413a of the head 406, and rounded contact surface 471 of sleeve 436 engages the other side of the head 67 of screw 63, on the second side portion 413b of the head, in longitudinally spaced apart positions along the length of the screw 63. The location of rounded contact surface 471 relatively close to the other side of nail head 406, and outer wall 413 of the head 406, from nail contact surface 428 provides a relatively large pivot arm for reducing the force exerted on each of surfaces 428 and 471. Further, the rounded configuration of surfaces 428 and 471, each of which contours closely to the cylindrical contour of the fixation screw 63, provides a relatively large surface area at each surface 428 and 471 for disbursing such forces and minimizing large point loads on both of the nail head 406 and the sleeve 436. For example, when nail 402 is placed within a femur 311 of human, the relatively large loads placed on head 326 of the femur, and thus fixation screw 63, while the human is upright or walking can be more easily supported by the relatively large moment arm and contact surfaces 428 and 471 acting on fixation screw 63 by nail 402.

In one embodiment, fixation screw 63 can be pivoted from a first angled or first extreme position, for example at an angle of approximately 120 degrees relative to head 406 of the nail 402 as shown in FIG. 68, to an intermediate or angled position, for example at an angle of approximately 130 degrees relative to head 406 as shown in FIG. 80, to a second angled or second extreme position, for example at an angle of 140 degrees relative to head as shown in FIG. 81. When in its first extreme position of 120 degrees as shown in FIG. 68, fixation screw 63 is further supported during loading by the engagement of cutout surface 426 with screw 63 adjacent rounded contact surface 471 of sleeve 436. When in its second extreme position of 140 degrees shown in FIG. 81, screw 63 is extensively supported by the relatively flush engagement of the screw 63, now in relative alignment with aperture axis 417 of nail 402 and aperture axis 462 of sleeve 436, by nail circular inner surface 423 forming nail aperture 416 and by sleeve circular inner surface 466 forming sleeve aperture 461.

Once the fixation screw 63 has been desirable angled relative to nail 402, set screw 438 can be inserted through the driver 511 into the internally threaded proximal portion 456a of sleeve bore 456 and advanced distally until the rounded end 522 of the set screw engages the fixation screw 63 to lock the fixation screw in its desired angled position and inhibit further pivoting or rotation of the screw 63 within apertures 416 and 461. In one embodiment, rounded end 522 of the set screw 438 seats within one of the longitudinal slots 204 of the fixation screw 63 for enhancing the rotatable locking of the screw 63 within nail head 406.

In one method of using the implantable devices of the present invention, for example apparatus 401 and nail 402, the head of the device can be secured to a targeting assembly or targeting device for inserting the implantable device into a mammalian body. For example, when the implantable device is an intramedullary rod or nail, such as nail 402, the rod or nail can be secured to a distal portion of a targeting assembly or jig and then directed or placed into the mammalian body with such targeting assembly. In one embodiment, the targeting assembly is provided with a handle portion and an arm portion extending from the handle portion with a threaded element or bolt provided at the distal end of the arm for threading into threaded portion 412a of proximal recess 412 in head 406 of the nail 402.

Figure 82:
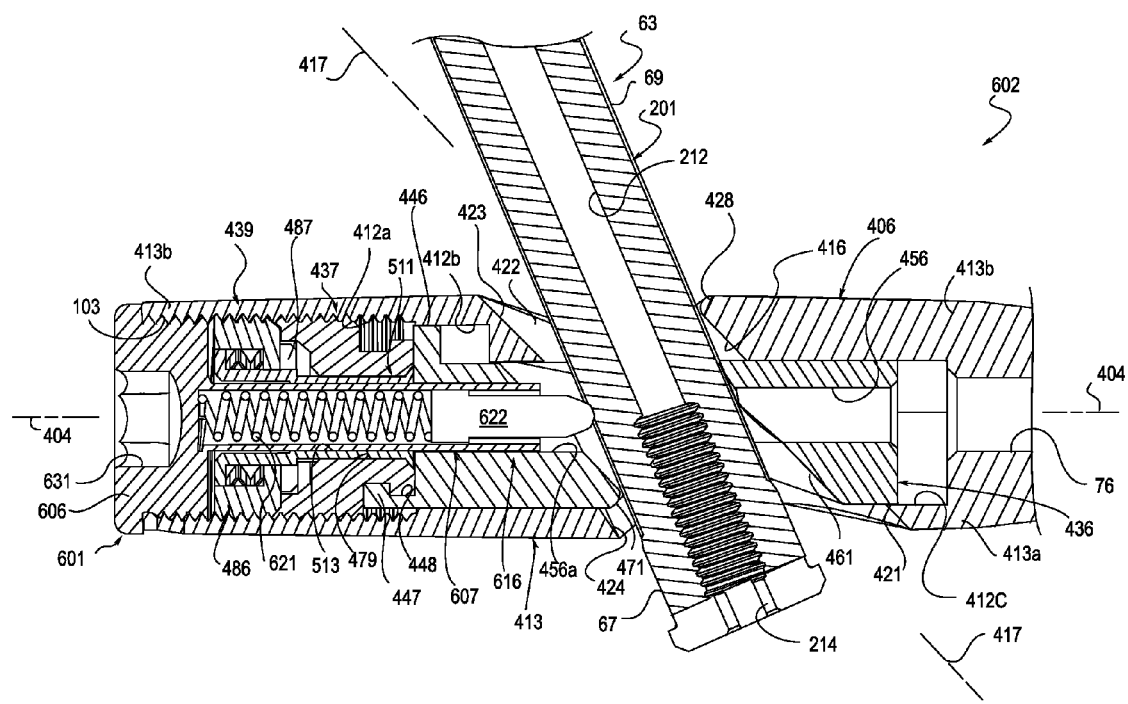
FIG. 82 is an enlarged cross-sectional view of a portion of intramedullary rod of FIG. 68 with a self-adjusting set screw of the present invention.
Figure 83:
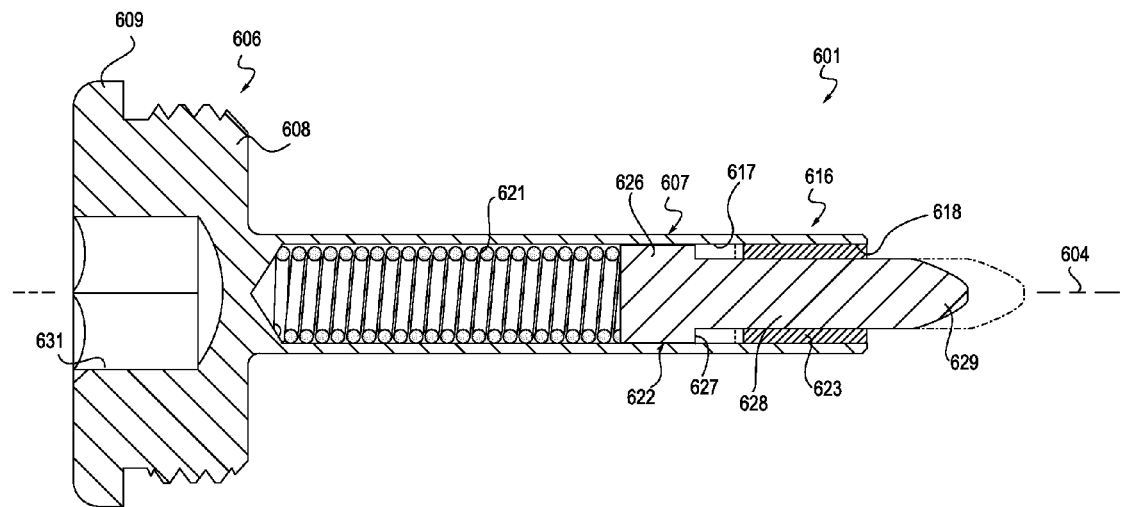
FIG. 83 is an enlarged cross-sectional view of the self-adjusting set screw of FIG. 82.

In another embodiment of the invention, a single apparatus can be provided for closing or sealing proximal recess 412 and locking fixation screw 63 once the screw has been angled relative to nail head 406 to a desired position. An embodiment of such apparatus 601 is illustrated in FIGS. 82-83 with respect to nail 602, which is substantially similar to nail 402 but excludes set screw 438 of the nail 402. Like reference numbers have been used to describe liked components of nails 602 and 402.

Apparatus 601, as illustrated apart from nail 602 in FIG. 83, includes a cylindrical body 603 made from any suitable material such as stainless steel that extends longitudinally along a longitudinal or central axis 604, which can be coincident with the longitudinal axis 404 of the nail 602. Body 603 has a proximal portion or cap 606 and a distal portion or shaft 607 extending from cap 606. Cap 606 and shaft 607 are unitarily formed by the body 603. The cap 606 has a portion 608 for lockably seating within proximal recess 412 of head 406, and in one embodiment such portion 608 is an externally-threaded or threaded portion 608 for threaded insertion into the internally-threaded portion 412a of the nail head 406. The cap is additionally provided with a flange or lip 609 at is proximal end, which extends radially outwardly from the threaded portion 608.

Tubular shaft 607 is included within the set screw 616 of apparatus 601. The shaft has an external diameter that approximates but is slightly less than the internal diameter of proximal bore 456a of sleeve 436. Unlike in nail 402, the proximal bore 456a of the sleeve 436 is not internally-threaded, and instead is circular and smooth so as to be capable of slidably-receiving shaft 607 of the apparatus 601 with a relatively snug fit so as to inhibit radial movement of the shaft 607 within the sleeve 436. The shaft 607 is provided with a longitudinally-extending bore 617 that can extend from the threaded portion 608 of cap 606 to a distal opening 618 provided in the shaft. Set screw 616 further includes a suitable spring such as coil spring 621 and a plunger 622 that are loaded into bore 617, and a collar or sleeve 623 for retaining the plunger and coil spring within the bore. The cylindrical plunger 622 can be made from any suitable material such as stainless steel and includes an enlarged proximal portion or head 626 terminating at a distal shoulder 627 and an extension 628 extending distally of the head 626 and concentric with the head. The extension terminates at a distal end 629, which can be rounded and slidably protrudes from distal opening 618 of the set screw 616. The distal end 629 of the plunger 622 serves as the distal end of the set screw 616. Tubular collar 623, which can be made from stainless steel or any other suitable material, can be press fit into distal opening 618 after the coil spring 621 and then the plunger 622 have been loaded into bore 617 and laser welded or otherwise suitably secured to the shaft 607 for retaining the coil spring and plunger within the bore. In one embodiment, the collar is seated in the bore 617 flush with the distal opening 618. The collar 623 is provided with a central bore 631 extending longitudinally therethrough for slidably receiving extension 628 of the plunger 622. The extension has an external diameter that approximates but is slightly less than the internal diameter of the collar so as to permit such slidable movement of the extension within the collar yet inhibit radial movement of the extension 628 within the collar 623.

The plunger 622 and its distal end 629 are movable relative to the proximal end or cap 606 of apparatus 601 between first and second positions. In one embodiment, such distal end 629 of the set screw 616 is movable between a first or proximal longitudinal position, shown in solid lines in FIG. 83 where the extension 628 is partially recessed within bore 617, and a second or distal longitudinal position, shown is phantom lines in FIG. 83 and in solid lines in FIG. 82 where the extension and its distal end 629 are further extended from the bore 617 and shaft 607 than when in the first position. The engagement of the shoulder 627 of the head 626 with collar 623 limits the distal travel of the distal end 629 relative to the proximal end of the set screw 616, and in one embodiment the second position of the distal end is proximal of an extreme distal position of the plunger 622 where shoulder 627 abuts collar 623. Spring 621 urges the plunger 622 and its distal end 629 in a distal direction or extended position relative to the shaft 607 and the proximal end of the set screw.

Apparatus 601 includes a suitable drive socket or recess 631 that extends distally into cap 606 for rotating the apparatus during placement in nail 602.

One or both of set screw 616 and apparatus 601 can be centered on longitudinal axis 404, although it is appreciated that embodiments can be provided where one or both of set screw 616 and apparatus 601 are not be centered on longitudinal axis 404.

Nail 602 can be placed within a bone in any suitable manner such as discussed herein. In one method of inserting the nail 602 into a bone of a mammalian body, the nail head 406 is connected to a suitable targeting assembly and placed in the appropriate bone of a body in a suitable manner, for example by means of a guide wire as discussed above. The targeting assembly can then be utilized to introduce a suitable fastener such fixation screw 63 through head 406 by means of lateral transverse opening 421, aperture 461 of sleeve 436 and medial transverse opening 422 so as to be positioned within the bone. Similar to the manner discussed above, fixation screw 63 can be pivoted relative to head 406 and central axis 404 through a range of angles by means of adjustment mechanism 411. In this regard, control element or worm gear 437 can be accessed through proximal opening 103 at the proximal end of head 406, for example by insertion of a suitable drive tool (not shown) through opening 103 and into proximal recess 412 and then into drive socket 513 of driver 511. The drive tool can then be utilized to unlocking locking mechanism 439 in the manner discussed, and then the drive tool can be used to rotate the driver 511 so as to rotate worm gear 437 and thus cause the worm gear and sleeve 436 coupled to the worm gear to move longitudinally within recess 412. As discussed above, longitudinal movement of the sleeve relative to head 406 causes the fixation screw to pivot about medial transverse opening 422 of the head 406.

Once the fixation screw has been pivoted to the desired angular position relative to head 406 and secured into the bone, apparatus 601 can be inserted through proximal opening 103 of the head and into proximal recess 412 of the head (see FIG. 82). In this regard, shaft 607 has a suitable external radius to permit the shaft to slide through drive socket 513 and bore 514 of drive 511 and then into proximal bore portion 456a of sleeve 436. The distal end of a suitable drive tool can be seated in drive socket 631 of cap 606 for rotatably securing the cap within the threaded portion 412a of proximal recess 412 of the head 406. Lip 609 seats on the proximal end of the head 406 for limiting the distal travel of the cap 606 and set screw 616 into the head 406. Lip 609 has an external diameter approximating the external diameter of the head 406 so as to seat flush on the proximal end of the head.

Apparatus 601 and set screw 616 are longitudinally sized so that the distal end 629 of the set screw lockably engages the fixation screw 63, regardless of the angular position of the set screw 63 relative to the head 406, and inhibits, retards, suppresses or restrains movement of the screw 63 relative to nail head 406. Such inhibited, retarded, suppressed or restrained movement of the screw 63 can include rotational or torsional movement of the screw 63 about its longitudinal axis, medial or lateral movement of the screw 63 relative to head 406 and sliding of the screw 63 relative to the head 406. Such inhibited movement can be partial, for example limited, or total, for example prohibited. Thus, when the fixation screw 63 is in a first extreme angled position relative to the head 406, for example as shown in FIGS. 82 and 68, distal end 629 of the set screw 616 is in its second longitudinal position, for example as shown in FIG. 82. When the fixation screw 63 is in a second extreme angled position relative to the head 406, for example as shown in FIG. 81, the distal end 629 of the set screw is in its first longitudinal position, for example as shown in FIG. 83. When the distal end 629 of the set screw 616 is in each of its extreme longitudinal positions relative to cap 606, coil spring 621 provides a sufficient longitudinal force on the distal end 629 to cause the set screw 616 to lockably engage the fixation screw, and thus inhibit undesirable rotation of screw 63 about its central axis, inhibit the screw from undesirably moving medially or laterally relative to head 406 and inhibit undesirable sliding of the screw 63 along its central axis.

Cap 606 desirably keeps the bone from growing into the nail 602 for easier nail removal. The cap further allows easier access to the nail 602 later for extraction, particularly if the nail is in very deep in a bone or in a large person. Cap 606 can be provided in different sizes to accommodate a variety of implantable devices such as nails.

The combination of cap 606 and set screw 616 into one piece is advantageous. In this regard, for example, because apparatus 601 piece is larger and longer then a regular set screw or cap independently, it is easier to insert into the nail 602 or other implantable device. As discussed above, set screw 616 is configured to engage the fixation screw 63 regardless of the angular position of the set screw 63 relative to the nail 602 because distal end 629 of the set screw can move between various operational positions relative to shaft 607 and the proximal end or cap 606. Hence, an apparatus 601 of one length works for all angles of the fixation or lag screw 63 relative to the nail 602. So, having the spring in there allows the set screw to engage the lag screw at any nail-lag screw angle and still limit rotation and control sliding of the set screw within the nail. Accordingly, the manufacturing of apparatus 601 can be relatively inexpensive.

As can be seen from the foregoing, an apparatus has been provided for treating fractures of the femur that marries the fixation attributes of an intramedullary nail with the benefits of a sliding compression screw. The apparatus provides a single device for treating a variety of femoral or other bone fractures, which heretofore have required more than one device. The device can be used to treat a variety of femoral fractures and femoral osteotomies and permits hospitals and manufacturers to reduce the variety of inventories of orthopedic surgical devices and thereby reduce costs. The device allows physicians to move the fracture or osteotomy to a more favorable position after implantation, and for example allows sliding compression of a femoral neck or intertrochanteric fracture. The apparatus permits the physician to vary the angle of one or more proximal fixation screws extending into the head of the femur or other bone, which can be done before insertion or after insertion of the femoral rod into the femoral intramedullary canal. The apparatus can further include one or more additional proximal fixation screws that are nonpivotable relative to the nail and can serve to increase the overall mechanical strength of the apparatus. One or more of such nonpivotable screws can abut one or more of the pivotable fixation screws for inhibiting undesirable post-fixation movement of such pivotable screws and can be further utilized to cause pivoting of such pivotable screws. The device can include a locking mechanism for inhibiting the fixation screw from undesirably pivoting relative to the rod or nail after completion of the procedure.

We claim:

1. An intramedullary device for use with a fastener to repair a bone in a mammalian body, comprising an elongate nail extending along a longitudinal axis and having a stem and a head, the head being provided with a transverse aperture that is adapted to receive the fastener, and an adjustment mechanism carried by the head for pivoting the fastener from a first angled position relative to the head to a second angled position relative to the head, a self-adjusting set screw carried by the head and having a proximal end and a distal end, the proximal end being accessible from the head and configured for driving the set screw into the head and the distal end being configured for lockably engaging the fastener so as to inhibit movement of the fastener relative to the head, the distal end of the set screw being movable relative to the proximal end of the set screw from a first position for lockably engaging the fastener in the first angled position to a second position for lockably engaging the fastener in the second angled position.

2. The intramedullary device of claim 1, wherein the distal end of the set screw is movable between first and second longitudinal positions relative to the proximal end of the set screw, the set screw including a spring for urging the distal end of the set screw to the second position.

3. The intramedullary device of claim 1 wherein the set screw is centered on the longitudinal axis.

4. The intramedullary device of claim 1, wherein the head includes a proximal end and the adjustment mechanism includes a rotatable control element carried by the head and accessible at the proximal end for causing the adjustment mechanism to pivot the fastener, the adjustment mechanism including a locking mechanism which precludes rotation of the control element when in a first position and permits rotation of the control element when in a second position.

5. The intramedullary device of claim 1, wherein the adjustment mechanism is disposed in the head and includes a sleeve that is slidable longitudinally relative to the head.

6. The intramedullary device of claim 5, wherein the sleeve is provided with an opening for receiving the fastener.

7. The intramedullary device of claim 1, wherein the adjustment mechanism includes a screw.

8. An intramedullary device for use with a fastener to repair a bone in a mammalian body, comprising an elongate nail extending along a longitudinal axis and having a stem and a head, the head being provided with a transverse aperture that is adapted to receive the fastener, the head being configured to permit pivoting of the fastener from a first angled position relative to the head to a second angled position relative to the head, a self-adjusting set screw carried by the head and having a proximal end and a distal end for lockably engaging the fastener so as to inhibit movement of the fastener relative to the head, the distal end of the set screw being slidably carried by the proximal end of the set screw for longitudinal movement from a first position for lockably engaging the fastener in the first angled position to a second position for lockably engaging the fastener in the second angled position.

9. The intramedullary device of claim 8, further comprising an adjustment mechanism carried by the head for pivoting the fastener from the first angled position to the second angled position.

10. The intramedullary device of claim 9, further comprising a spring for urging the distal end of the set screw to the second position.

11. The intramedullary device of claim 9, wherein the aperture has opposite first and second side portions relative to the longitudinal axis and wherein the adjustment mechanism pivots the fastener about a pivot axis in the first side portion extending perpendicular to the longitudinal axis.

12. An intramedullary device for repairing a bone in a mammalian body, comprising an elongate nail extending along a longitudinal axis and having a stem and a head, the head being provided with a transverse aperture that is adapted to receive the fastener, the head being configured to permit pivoting of the fastener from a first angled position relative to the head to a second angled position relative to the head, a self-adjusting set screw carried by the head and having a proximal end and a distal end for lockably engaging the fastener so as to inhibit movement of the fastener relative to the head, the distal end of the set screw being movable relative to the proximal end of the set screw from a first position for lockably engaging the fastener in the first angled position to a second position for lockably engaging the fastener in the second angled position, and a swing for urging the distal end of the set screw to the second position.

13. The intramedullary device of claim 12, wherein the distal end of the set screw is movable longitudinally relative to the proximal end of the set screw.

14. The intramedullary device of claim 13, wherein the distal end of the set screw is movable between first and second longitudinal positions relative to the proximal end of the set screw, the distal end of the set screw being urged to the second longitudinal position by the spring.

15. The intramedullary device of claim 12, wherein the set screw is centered on the longitudinal axis.

16. The intramedullary device of claim 12, wherein the head is provided with a proximal recess that is internally threaded and the set screw is externally threaded so as to threadably engage the proximal recess.

17. A self-adjusting set screw for use with an intramedullary device having a head provided with a transverse aperture for receiving a fastener and a proximal threaded recess and a stem extending distally from the head, comprising a longitudinally-extending body having an externally-threaded portion adapted for threaded insertion into the threaded recess of the head, the body being provided with a longitudinal bore extending to a distal opening, a plunger slidably disposed in the bore and having a proximal end portion and a distal end portion extending from the distal opening, and a spring disposed in the bore and engaging the proximal end portion of the plunger for urging the distal end portion of the plunger against the fastener when the body is disposed in the head of the intramedullary device.

18. The apparatus of claim 17, further comprising a collar disposed in the bore at the distal opening for retaining the plunger within the bore.

19. An intramedullary device for use with a fastener to repair a bone in a mammalian body, comprising an elongate nail extending along a longitudinal axis and having a stem and a head, the head being provided with a transverse aperture that is adapted to receive the fastener, the head being configured to permit pivoting of the fastener about a pivot axis extending perpendicular to the longitudinal axis from a first angled position relative to the head to a second angled position relative to the head, and a self-adjusting set screw carried by the head and having a proximal end and a distal end, the proximal end being accessible from the head and configured for driving the set screw into the head and the distal end being configured for lockably engaging the fastener, the distal end of the set screw being movable relative to the proximal end of the set screw from a first position for lockably engaging the fastener in the first angled position to a second position for lockably engaging the fastener in the second angled position.

20. The intramedullary device of claim 19, further comprising an adjustment mechanism carried by the head for pivoting the fastener from the first angled position to the second angled position.

21. The intramedullary device of claim 20 wherein the aperture has opposite first and second side portions relative to the central longitudinal axis and wherein the adjustment mechanism engages the fastener in the second side portion of the aperture.

22. The intramedullary device of claim 21, wherein the adjustment mechanism extends longitudinally of the head.

* * * * *